United States Patent
Liu et al.

(10) Patent No.: US 10,669,238 B2
(45) Date of Patent: Jun. 2, 2020

(54) IRREVERSIBLE BRUTON'S TYROSINE KINASE INHIBITOR

(71) Applicant: HEFEI INSTITUTES OF PHYSICAL SCIENCE, CHINESE ACADEMY OF SCIENCES, Hefei, Anhui (CN)

(72) Inventors: Jing Liu, Anhui (CN); Qingsong Liu, Anhui (CN); Qianmao Liang, Anhui (CN); Yongfei Chen, Anhui (CN); Cheng Chen, Anhui (CN); Aoli Wang, Anhui (CN); Hong Wu, Anhui (CN); Kailin Yu, Anhui (CN); Wei Wang, Anhui (CN); Chen Hu, Anhui (CN); Wenchao Wang, Anhui (CN); Shuang Qi, Anhui (CN); Beilei Wang, Anhui (CN); Li Wang, Anhui (CN)

(73) Assignee: HEFEI INSTITUTES OF PHYSICAL SCIENCE, CHINESE ACADEMY OF SCIENCES, Hefei, Anhui (CN)

( * ) Notice: Subject to any disclaimer, the term of this patent is extended or adjusted under 35 U.S.C. 154(b) by 0 days.

(21) Appl. No.: 16/074,970

(22) PCT Filed: Dec. 22, 2016

(86) PCT No.: PCT/CN2016/111442
§ 371 (c)(1),
(2) Date: Aug. 2, 2018

(87) PCT Pub. No.: WO2017/133341
PCT Pub. Date: Aug. 10, 2017

(65) Prior Publication Data
US 2019/0040013 A1 Feb. 7, 2019

(30) Foreign Application Priority Data
Feb. 4, 2016 (CN) .......................... 2016 1 0084082

(51) Int. Cl.
| | |
|---|---|
| *C07D 213/74* | (2006.01) |
| *C07D 401/12* | (2006.01) |
| *C07D 405/12* | (2006.01) |
| *C07D 409/12* | (2006.01) |
| *A61P 35/02* | (2006.01) |
| *A61P 35/00* | (2006.01) |

(52) U.S. Cl.
CPC ............ *C07D 213/74* (2013.01); *A61P 35/00* (2018.01); *A61P 35/02* (2018.01); *C07D 401/12* (2013.01); *C07D 405/12* (2013.01); *C07D 409/12* (2013.01); *Y02P 20/55* (2015.11)

(58) Field of Classification Search
CPC .. C07D 213/74; C07D 401/12; C07D 405/12; C07D 409/12
See application file for complete search history.

(56) References Cited

U.S. PATENT DOCUMENTS 5,565,469 A * 10/1996 Mihm ................ C07D 235/18
514/300
2006/0229337 A1 10/2006 Brittelli et al.

FOREIGN PATENT DOCUMENTS

| CN | 101223141 A | 7/2008 |
|---|---|---|
| CN | 101835755 A | 9/2010 |
| CN | 101861307 A | 10/2010 |
| WO | WO 2006/099075 * 9/2006 |
| WO | WO 2009/137596 A1 | 11/2009 |

OTHER PUBLICATIONS

Fura, A. DDT, 2006, 11, pp. 133-142.*
Anari et al. DDT, 2005, 10, pp. 711-717.*
Neddernnan, A.N.R. Biopham, Drug Dispos., 2009, 30, pp. 152-162.*
Liang Q. et al., "Discovery of N-(3-(5-((3-Acrylamido-4-(Morpholine-4-Carbonyl)Phenyl)Amino)-1-Methyl-6-Oxo-1,6-Dihydropyridin-3-YI)-2-Methylphenyl)-4-(Tert-Butyl)Benzamide (CHMFL-BTK-01) as a Highly Selective Irreversible Bruton's Tyrosine Kinase (BTK) Inhibitor", European Journal of Medicinal Chemistry 131:107-125 (2017).
Lou Y. et al., "Structure-Based Drug Design of RN486, a Potent and Selective Bruton's Tyrosine Kinase (BTK) Inhibitor, for the Treatment of Rheumatoid Arthritis", Journal of Medicinal Chemistry 58:512-516 (2015).
Extended Supplementary European Search Report dated Jul. 29, 2019 received in European Application No. 16 88 9147.1.
International Search Report dated Mar. 27, 2017 issued in PCT/CN2016/111442.

(Continued)

*Primary Examiner* — Rebecca L Anderson
(74) *Attorney, Agent, or Firm* — Scully, Scott, Murphy & Presser, P.C.

(57) ABSTRACT

The present invention provides an inhibitor of Bruton's tyrosine kinase, which is a compound of formula (I), or its pharmaceutically acceptable salt, solvate, ester, acid, metabolite or prodrug. The present invention also provides a pharmaceutical composition comprising the compound. The present invention also provides a method for inhibiting the activity of tyrosine kinase activity or for treating a disease, disorder, or condition, which would benefit from the inhibition of Bruton's tyrosine kinase(s), by using the Bruton's tyrosine kinase inhibitor, as well application of the Bruton's tyrosine kinase inhibitor for the same.

formula (I)

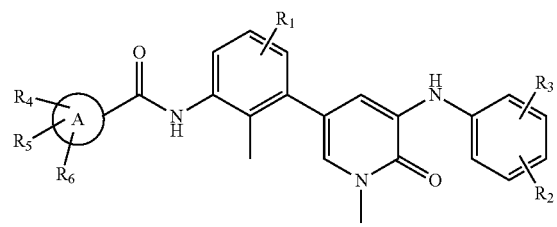

21 Claims, 9 Drawing Sheets
Specification includes a Sequence Listing.

(56) References Cited

OTHER PUBLICATIONS

GenBank Accession No. AAB47246.1 (2 pages) (Aug. 9, 2000).
GenBank Accession No. NP_000052.1 (5 pages) (Jul. 15, 2018).
GenBank Accession No. NP_979564 (2 pages) (Dec. 17, 2014).
GenBank Accession No. NP_001007799.1 (3 pages) (Oct. 1, 2017).
GenBank Accession No. XP_549139.2 (2 pages) (Sep. 5, 2017).
GenBank Accession No. XP_698117.2 (1 page) (Feb. 16, 2007).
Jeffries, Caroline A. et al.., "Bruton's Tyrosine Kinase Is a Toll/Interleukin-1 Receptor Domain-binding Protein That Participates in Nuclear Factor kB Activation by Toll-like Receptor 4*", The Journal of Biological Chemistry (Jul. 11, 2003), vol. 278, No. 28, pp. 26258-26264.
Kurosaki, Tomohiro, "Functional dissection of BCR signaling pathways", Curr Op Imm (2000), pp. 276-281.
Schaeffer, Edward M., "Tec family kinases in lymphocyte signaling and function", Curr Op Imm (2000), pp. 282-288.
Vassilev, Alexei et al., "Bruton's Tyrosine Kinase as an Inhibitor of the Fas/CD95 Death-inducing Signaling Complex*", The Journal of Biological Chemistry (Jan. 15, 1999), vol. 274, No. 3, pp. 1646-1656.
Quek, L.S.et al., "A role for Bruton's tyrosine kinase (Btk) in platelet activation by collagen", Current Biology (1998), vol. 8, No. 20, pp. 1137-1140.

\* cited by examiner

BTK WT:EC50=4.7nM

BTK C481S:EC50=185.1nM

BTK WT:EC50 = 16 nM

BTK C481S:EC50=186 nM

IRREVERSIBLE BRUTON'S TYROSINE KINASE INHIBITOR

INCORPORATION BY REFERENCE OF SEQUENCE LISTING

The Sequence Listing in the ASCII text file, named as 36367_SequenceListing.txt of 4 KB, created on Dec. 10, 2019, and submitted to the United States Patent and Trademark Office via EFS-Web, is incorporated herein by reference.

TECHNICAL FIELD

The present application relates to a compound acting as an inhibitor against Bruton's tyrosine kinase (Btk), a pharmaceutical composition comprising the compound, and a method of inhibiting activity of Bruton's tyrosine kinase by using said compound or composition, as well as the use thereof.

BACKGROUND OF THE INVENTION

Bruton's tyrosine kinase is a member of the Tec family of non-receptor tyrosine kinases. It consists of five parts: a PH domain, a TH domain, a SH3 domain, a SH2 domain, and a catalytic domain. Btk is involved in a variety of signaling pathways, it plays an important role in regulation of cell proliferation, differentiation and apoptosis, and it is a key signal enzyme expressed in all hematopoietic cell types except T lymphocytes and natural killer cells. Moreover, Btk plays a critical role in B cell signaling pathways that associates cell-surface B-cell receptor (BCR) stimulation with downstream intracellular responses.

Btk is a key regulator for B cell development, activation, signaling, and survival (Kurosaki, *Curr Op Imm*, 2000, 276-281; Schaeffer and Schwartzberg, *Curr Op Imm*, 2000, 282-288). In addition, Btk plays a role in a number of other hematopoietic cell signaling pathways, such as Toll like receptor (TLR) and cytokine receptor-mediated TNF-α production in macrophages, IgE receptor (FcεRI) signaling in Mast cells, signaling for inhibiting Fas/APO-1 cell apoptosis in B-lineage lymphoid cells and collagen-stimulated platelet aggregation. See, e.g., C. A. Jeffries, et al., (2003), *Journal of Biological Chemistry* 278: 26258-26264; Vassilev et al. (1999), *Journal of Biological Chemistry* 274(3): 1646-1656; and Quek et al. (1998), *Current Biology* 8(20): 1137-1140.

SUMMARY OF THE INVENTION

The present invention relates to a Bruton's tyrosine kinase inhibitor. Specifically, the compounds of the present invention comprises the compounds of formula (I), or pharmaceutically acceptable salts, solvates, isomers, esters, acids, metabolites or prodrugs thereof:

formula (I)

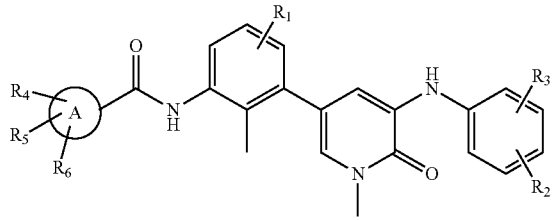

wherein,
ring A represents any monocyclic or fused-ring group selected from the group consisting of phenyl, thienyl, benzothiophenyl and tetrahydrobenzothiophenyl;

each of $R_1$ and $R_2$ is independently selected from the group consisting of hydrogen,

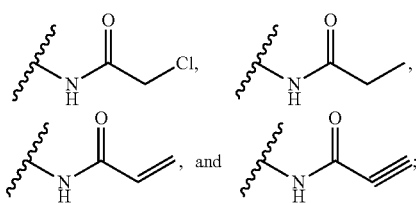

$R_3$ is selected from the group consisting of hydrogen, C1-C8 alkyl, halo, hydroxy, nitro, cyano, C1-C8 haloalkyl, amino, C1-C8 alkylamino, —(CO)—$R_7$, heterocycloalkyl optionally substituted with $R_8$, and heteroaryl optionally substituted with $R_8$;

each of $R_4$, $R_5$ and $R_6$ is independently selected from the group consisting of hydrogen, halo, hydroxy, amino, nitro, cyano, C1-C8 alkyl, C3-C8 cycloalkyl, C1-C8 haloalkyl, C1-C8 alkoxy, C1-C8 alkylamino, heterocycloalkyl, aryl and heteroaryl, or any adjacent two of $R_4$, $R_5$ and $R_6$ together form C3-C8 cycloalkyl or heterocycloalkyl;

$R_7$ is selected from the group consisting of C1-C8 alkoxy, C1-C8 alkylamino, C3-C8 cycloalkylamino, C2-C8 heteroalkylamino, C3-C8 heterocycloalkylamino, and heterocycloalkyl optionally substituted with halo, hydroxy, amino, nitro, cyano, C1-C8 alkyl, C1-C8 alkoxy, or amino protecting group;

$R_8$ is selected from the group consisting of C1-C8 alkyl, C1-C8 alkoxy, C1-C8 alkylamino or C2-C8 alkanoyl.

In another aspect, the compound of the present invention comprises a compound of formula (Ia), or a pharmaceutically acceptable salt, solvate, ester, acid, metabolite or prodrug thereof:

formula (Ia)

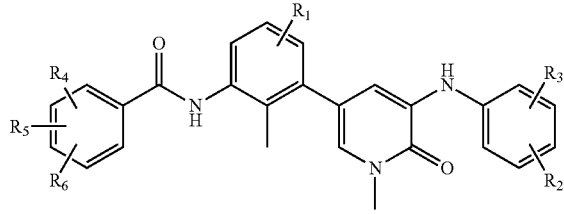

wherein, $R_1$, $R_2$, $R_3$, $R_4$, $R_5$ and $R_6$ are defined as above.

In a further preferred embodiment, the compound of the present invention comprises a compound of formula (IIa), or a pharmaceutically acceptable salt, solvate, ester, acid, metabolite or prodrug thereof:

formula (IIa)

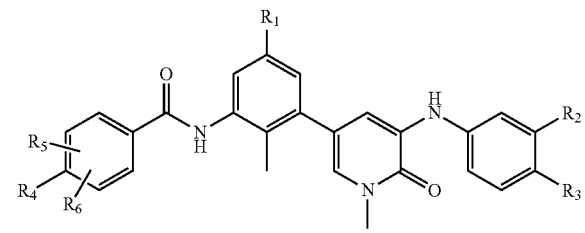

wherein, $R_1$, $R_2$, $R_3$, $R_4$, $R_5$ and $R_6$ are defined as above.

In another aspect, the compound of the present invention comprises a compound of formula (Ib), or a pharmaceutically acceptable salt, solvate, ester, acid, metabolite or prodrug thereof:

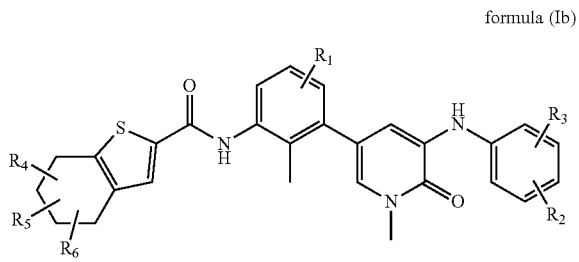

formula (Ib)

wherein, $R_1$, $R_2$, $R_3$, $R_4$, $R_5$ and $R_6$ are defined as above.

In a further preferred embodiment, the compound of the present invention comprises a compound of formula (IIb), or a pharmaceutically acceptable salt, solvate, ester, acid, metabolite or prodrug thereof:

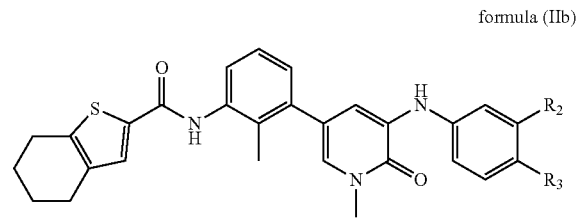

formula (IIb)

wherein, $R_2$ and $R_3$ are defined as above.

In other aspects, the compound of the present invention comprises a compound of formula (Ic), or a pharmaceutically acceptable salt, solvate, ester, acid, metabolite or prodrug thereof:

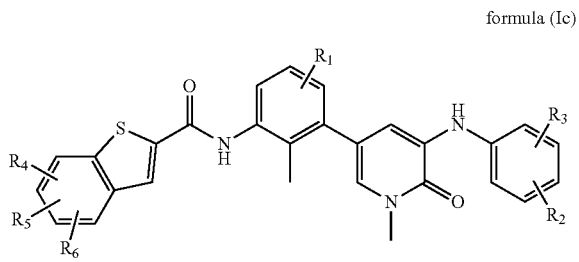

formula (Ic)

wherein, $R_1$, $R_2$, $R_3$, $R_4$, $R_5$ and $R_6$ are defined as above.

In a further preferred embodiment, the compound of the present invention comprises a compound of formula (IIc), or a pharmaceutically acceptable salt, solvate, ester, acid, metabolite or prodrug thereof:

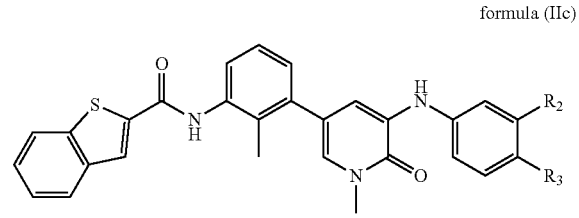

formula (IIc)

Wherein, $R_2$ and $R_3$ are defined as above.

In other aspects, the compound of the present invention comprises the compound of formula (Id), or a pharmaceutically acceptable salt, solvate, ester, acid, metabolite or prodrug thereof:

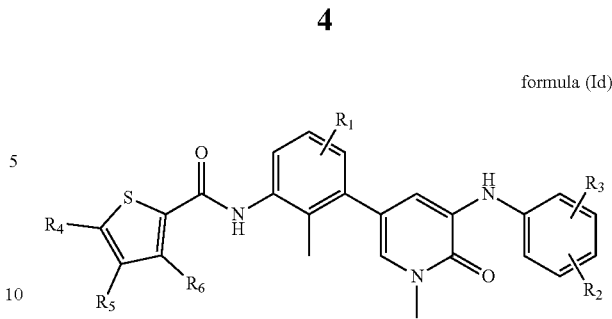

formula (Id)

wherein, $R_1$, $R_2$, $R_3$, $R_4$, $R_5$ and $R_6$ are defined as above.

In a further preferred embodiment, the compound of the present invention comprises the compound of formula (IId), or a pharmaceutically acceptable salt, solvate, ester, acid, metabolite or prodrug thereof:

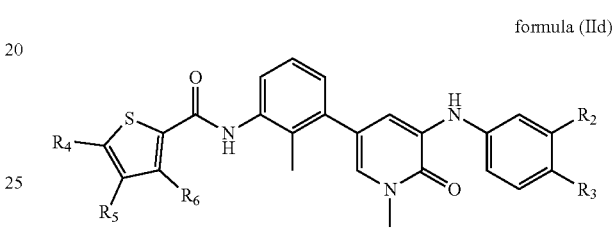

formula (IId)

wherein, $R_2$, $R_3$, $R_4$, $R_5$ and $R_6$ are defined as above.

In another aspect, the present application provides a pharmaceutical composition, which comprises a therapeutically effective amount of at least one of the compounds provided herein or a pharmaceutically acceptable salt, solvate, ester, acid, metabolite or prodrug thereof, and a pharmaceutically acceptable carrier or excipient, as well as optionally other therapeutic agent(s).

The above pharmaceutical composition is used for administration via suitable routes and ways, said pharmaceutical composition containing an effective concentration of one or more compounds provided herein, or a pharmaceutically acceptable salt, solvate, ester, acid, metabolite or prodrug thereof, that can release amounts effective for the treatment, prevention or amelioration of one or more symptoms of diseases, disorders or conditions that are modulated or otherwise affected by tyrosine kinase activity, or in which tyrosine kinase activity is implicated. The effective amounts and concentrations are effective for ameliorating the symptoms of any of the diseases, disorders or conditions disclosed herein.

In another aspect, the present application provides a method for treating a patient by administering a compound or a pharmaceutical composition provided herein. In some embodiments, provided herein is a method for inhibiting the activity of Bruton's tyrosine kinase (Btk), or for treating a disease, disorder, or condition, which would benefit from the inhibition of Bruton's tyrosine kinase (Btk) activity, which includes administering to the patient a therapeutically effective amount of at least one of any of the compounds provided herein, or pharmaceutically acceptable salts, solvates, esters, acids, metabolites or prodrugs thereof, or pharmaceutical compositions.

In a further aspect, the above diseases, disorders or conditions that are modulated or otherwise affected by tyrosine kinase activity, or in which tyrosine kinase activity is implicated comprises cancer, such as initiation or progression of solid tumor, sarcoma, lymphoma (such as B-cell lymphoma), leukemia, adenocarcinoma (such as breast ductal carcinoma, lobular carcinoma), melanoma, or the like, or the combination thereof. In one embodiment, the cancer is B-cell proliferative disease, such as diffuse large B-cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma or lymphomatoid granulomatosis, or the like, or the combination thereof. In some embodiments, the present invention is particularly preferred for the treatment of acute myeloid leukemia (AML), chronic lymphocytic leukemia (CLL), and other B-cell proliferative disease such as chronic lymphocytic lymphoma, diffuse large B-cell lymphoma (DLBCL), follicular lymphoma, or the like, and the combination thereof.

In some embodiments, the invention relates to the treatment of a subject in need who is suffering from an autoimmune disease, e.g., arthritis, rheumatic arthritis, osteoarthritis, lupus, rheumatoid arthritis, inflammatory bowel disease, psoriatic arthritis, osteoarthritis, Still's disease, juvenile arthritis, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myodonus syndrome, ankylosing spondylosis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia.

In another aspect, the tyrosine kinase that is inhibited as mentioned above comprises Bruton's tyrosine kinase, Bruton's tyrosine kinase homologs or Btk tyrosine kinase cysteine homologs thereof, which are covalently bound with the inhibitor of the invention. In a specific embodiment, the inhibitor is covalently bound to the cysteine residue of a tyrosine kinase.

In a further aspect, the present application provides a method for treating diseases, disorders or conditions that are modulated or otherwise affected by Bruton's tyrosine kinase activity, or in which tyrosine kinase activity is implicated (such as cancer), by administering to a subject in need thereof a composition containing a therapeutically effective amount of a compound of the present invention that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase or Bruton's tyrosine kinase homolog. In one embodiment, the compound selectively and irreversibly binds to BTK. In another embodiment, the compound selectively and irreversibly binds to tyrosine kinase JAK3 (Janus Kinase 3). In another embodiment, the compound selectively and irreversibly binds to bone marrow tyrosine kinase in chromosome X (bone marrow X kinase, BMX). In another embodiment, the compound selectively and irreversibly binds to epidermal growth factor receptor (EGFR).

In another aspect, the present application relates to a method for modulating, including irreversibly inhibiting, the activity of Btk or of other tyrosine kinases, wherein the other tyrosine kinases share homology with Btk by having a cysteine residue (including a Cys 481 residue) that can form a covalent bond with at least one irreversible inhibitor described herein, in a mammal, comprising administering to the mammal an effective amount of at least one compound of formula (I), (Ia), (IIa), (Ib), (IIb), (Ic), (IIc), (Id) or (IId) or its pharmaceutically acceptable salt, solvate, ester, acid, metabolite or prodrug, or a pharmaceutical composition comprising the compound of formula (I), (Ia), (IIa), (Ib), (IIb), (Ic), (IIc), (Id) or (IId) at least once.

In another aspect, the present application relates to the use of a compound of formula (I), (Ia), (IIa), (Ib), (IIb), (Ic), (IIc), (Id) or (IId) or the pharmaceutically acceptable salts, solvates, esters, acids, metabolites or prodrugs thereof in the manufacture of a madicament for the treatment of the above mentioned diseases, disorders or conditions. The present application further relates to the use of a compound of formula (I), (Ia), (IIa), (Ib), (IIb), (Ic), (IIc), (Id) or (IId) or the pharmaceutically acceptable salts, solvates, esters, acids, metabolites or prodrugs thereof in the manufacture of a medicament for modulating, including irreversibly inhibiting, activity of Btk or of other tyrosine kinase in a mammal.

In further or alternative embodiments, the compound of formula (I), (Ia), (IIa), (Ib), (Ib), (Ic), (IIc), (Id) or (IId), or a pharmaceutically acceptable salt, solvate, ester, acid, metabolite or prodrug thereof is an irreversible inhibitor of Bruton's tyrosine kinase (Btk). In still further or alternative embodiments, such irreversible inhibitors are selective for Btk. In even further or alternative embodiments, such inhibitors have an $EC_{50}$ below 10 µM in a Btk enzyme assay. In one embodiment, a Btk irreversible inhibitor has an EC50 of less than 1 µM, and in another embodiment, less than 0.3 µM.

In further or alternative embodiments, the compounds of formula (I), (Ia), (IIa), (Ib), (IIb), (Ic), (IIc), (Id) or (IId) are selective irreversible inhibitors for Btk over Itk (Interleukin 2 (IL-2) inducible T-cell kinase, also named Emt or Tsk). In further or alternative embodiments, the compounds of formula (I), (Ia), (IIa), (Ib), (IIb), (Ic), (IIc), (Id) or (IId) are selective irreversible inhibitors for Btk over Lck (lymphocyte-specific protein tyrosine kinase). In further or alternative embodiments, the compounds of formula (I), (Ia), (IIa), (Ib), (IIb), (Ic), (IIc), (Id) or (IId) are selective irreversible inhibitors for Btk over ABL (Abelson tyrosine-protein kinase 1, Abelson non-receptor tyrosine kinase). In further or alternative embodiments, the compounds of formula (I), (Ia), (IIa), (Ib), (IIb), (Ic), (IIc), (Id) or (IId) are selective irreversible inhibitors for Btk over CMET (also referred to as Hepatocyte growth factor receptor, HGFR, which is human Hepatocyte growth factor receptor). In further or alternative embodiments, the compounds of formula (I), (Ia), (IIa), (Ib), (IIb), (Ic), (IIc), (Id) or (IId) are selective irreversible inhibitors for Btk over EGFR. In further or alternative embodiments, the compounds of formula (I), (Ia), (IIa), (Ib), (IIb), (Ic), (IIc), (Id) or (IId) are selective irreversible inhibitors for Btk over Lyn (V-yes-1 Yamaguchi sarcoma viral related oncogene homolog, Lyn kinase).

In further or alternative embodiments, the irreversible Btk inhibitors are also inhibitors of JAK3.

In further or alternative embodiments, the irreversible Btk inhibitors are also inhibitors of EGFR.

In further or alternative embodiments, the irreversible Btk inhibitors are also inhibitors of BMX.

Other objects, features and advantages of the compounds, compositions, methods and uses described herein will become apparent from the following detailed description. It should be understood that the specific embodiments are given by way of illustration only, and various changes and modifications within the spirit and scope of the present disclosure will become apparent to those skilled in the art from this detailed description. All documents, or portions of documents, cited in the application including, but not limited to, patents, patent applications, articles, books, manuals, and treatises are hereby expressly incorporated by reference in their entirety for any purpose.

DESCRIPTION OF THE FIGURES

FIG. 2 illustrates the effects of compounds 1 and 35 on BTK Y223 and its downstream signaling pathway proteins in various cells, wherein

FIG. 3 illustrates the verification results of the irreversible inhibitory effects of compound 1 on Btk in various cells, wherein

DETAILED DESCRIPTION OF THE INVENTION

Terminology

Figure 1A:
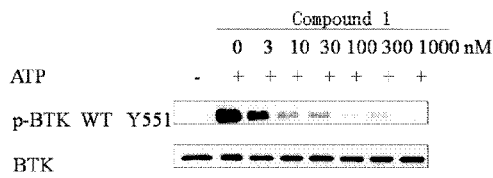
FIG. 1 illustrates the study on activity and irreversibility of in-vitro Btk inhibition of compounds 1, 6 and 35, wherein FIG. 1a and FIG. 1b respectively illustrate the inhibitory effects of compound 1 on BTK WT and BTK C481S.
FIG. 1c illustrates the inhibitory effects of compound 6 on the above two kinases.
FIG. 1d and FIG. 1e illustrate the inhibitory effects of compound 35 on BTK WT and BTK C481S.
Figure 1A:
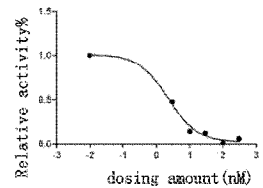
Figure 1B:
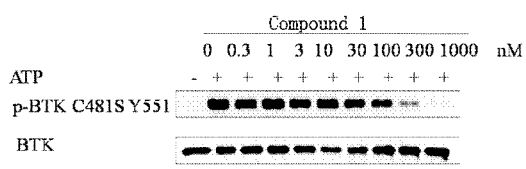
Figure 1B:
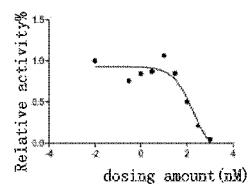
Figure 1C:
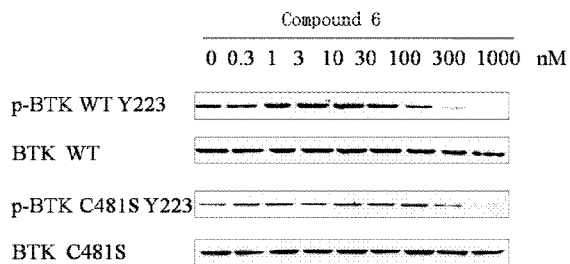
Figure 1D:
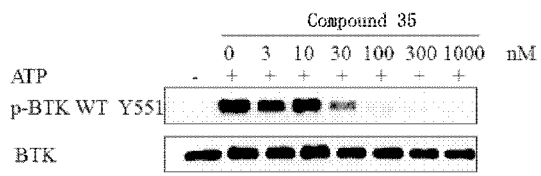
Figure 1D:
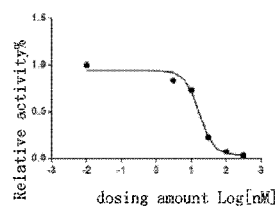
Figure 1E:
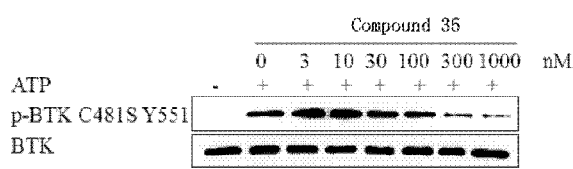
Figure 1E:
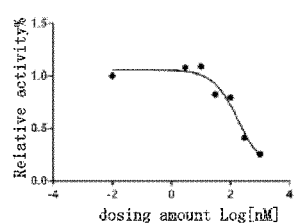
Figure 2A:
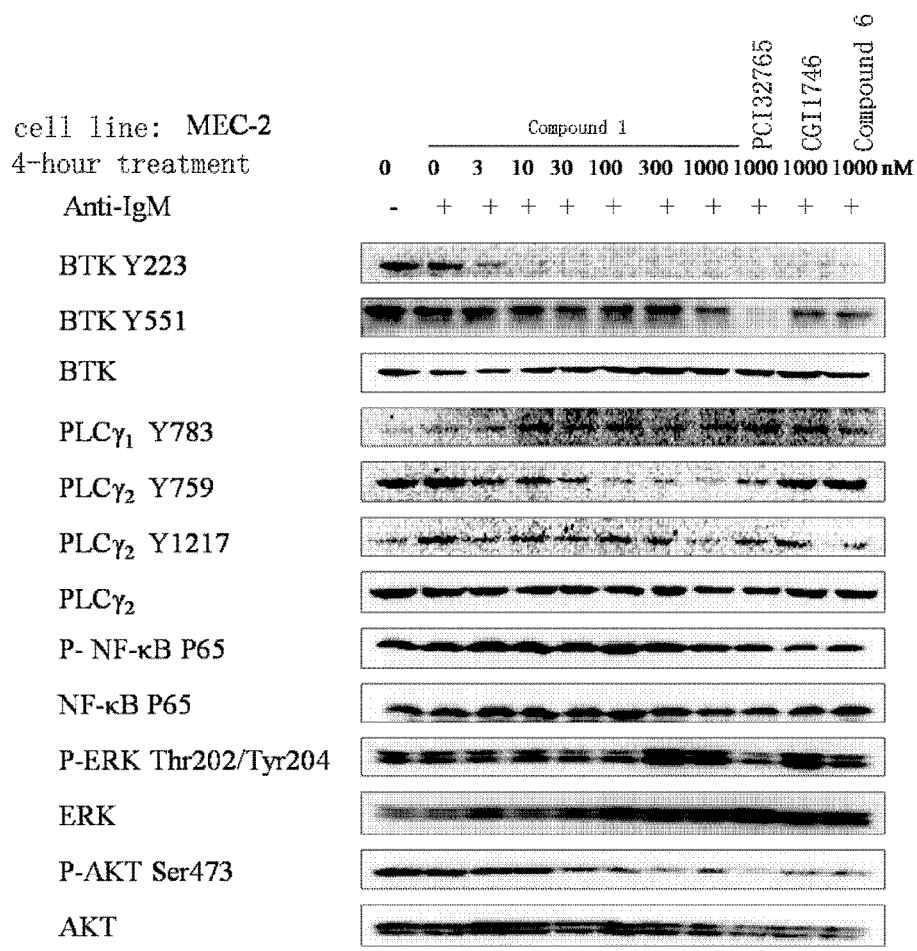
FIG. 2a illustrates the result of the compound 1 in MEC-2 cell line.
Figure 2B:
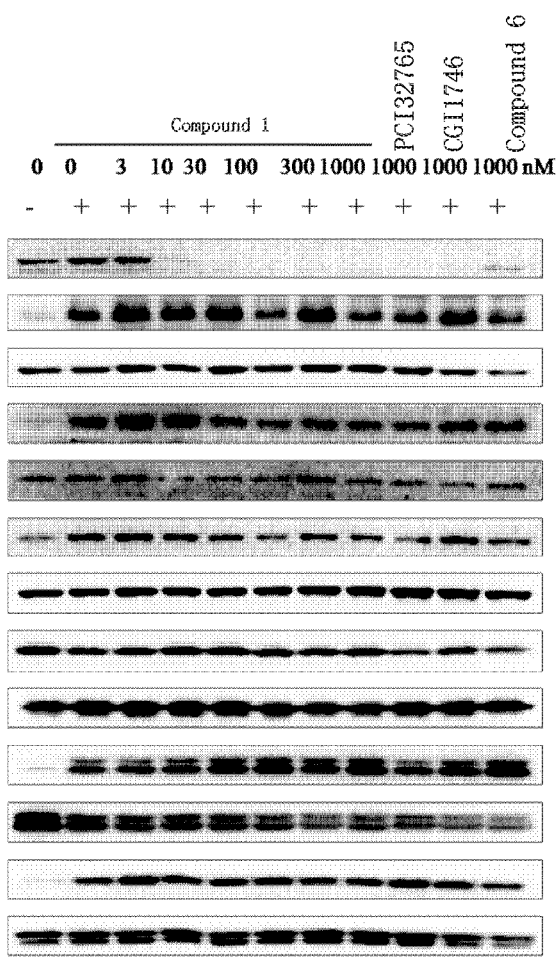
FIG. 2b illustrates the result of compound 1 in Pfeiffer cell line.
Figure 2C:
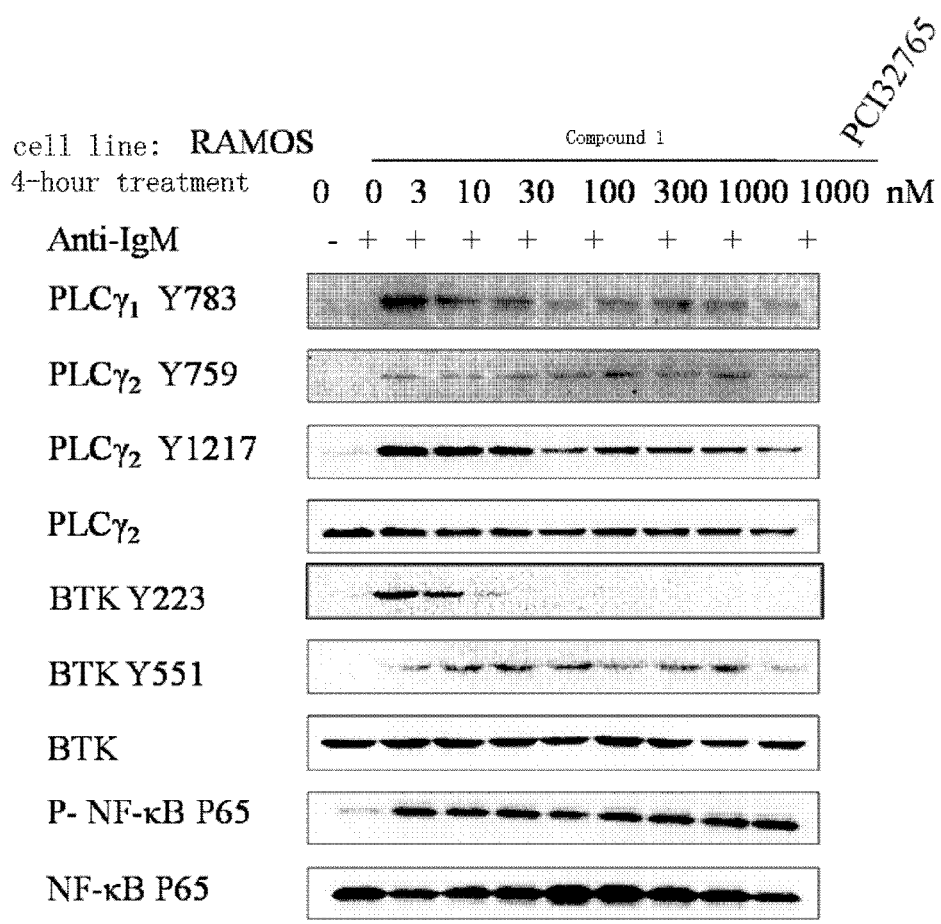
FIG. 2c illustrates the result of compound 1 in RAMOS cell line.
Figure 2D:
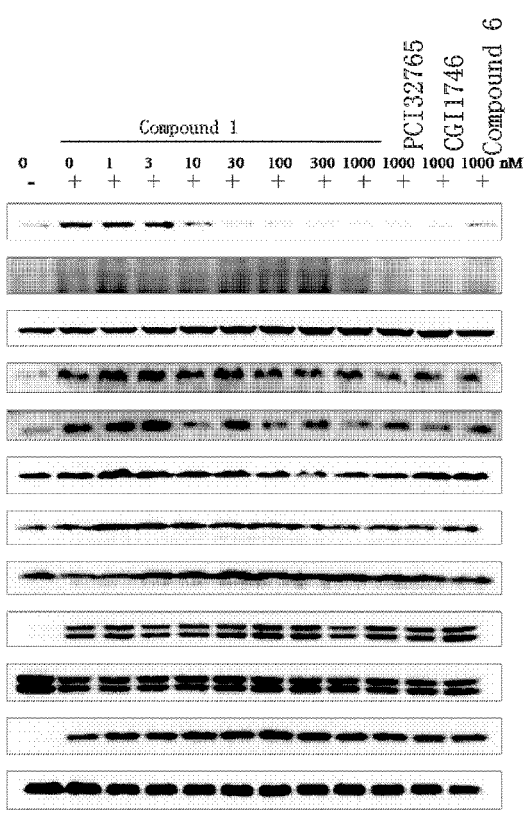
FIG. 2d illustrates the result of compound 1 in TMD8 cell line.
Figure 2E:
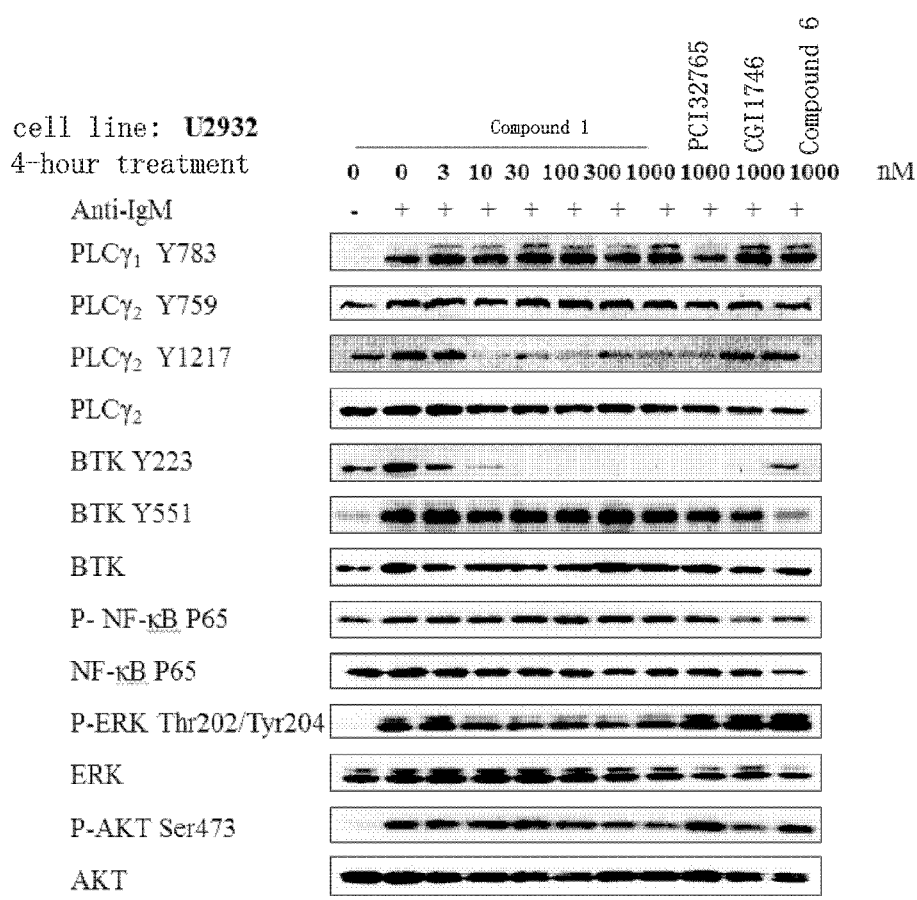
FIG. 2e illustrates the result of compound 1 in U2932 cell line.
Figure 2F:
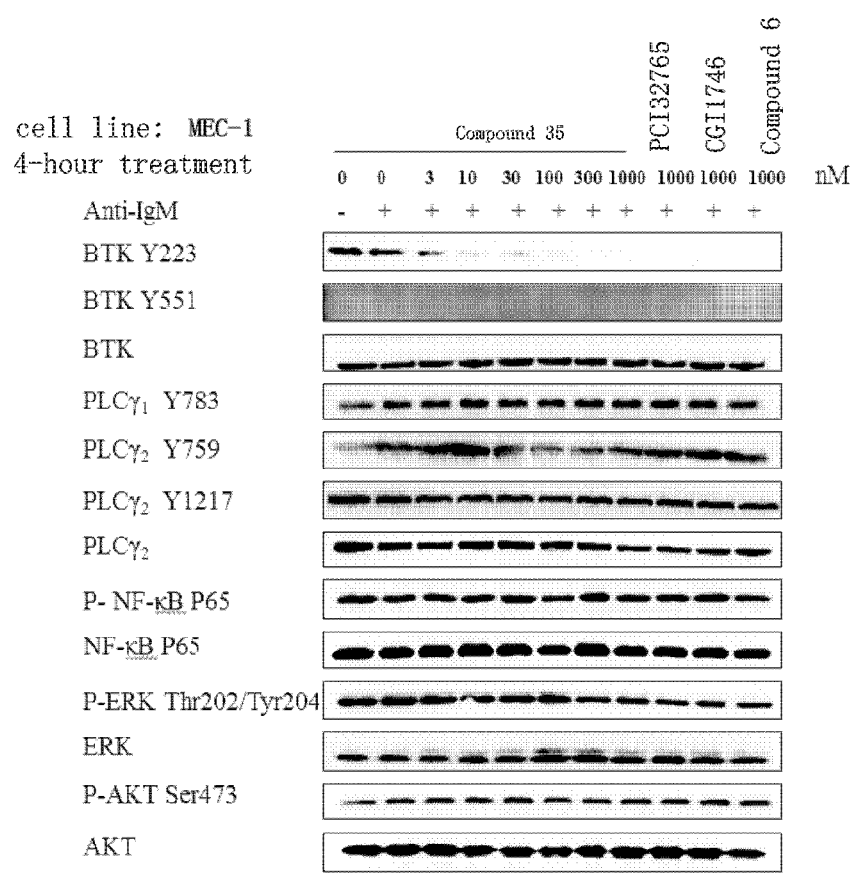
FIG. 2f illustrates the result of compound 35 in MEC-1 cell line.

Unless defined otherwise, all technical and scientific terms used herein have the same meaning as is commonly understood by one of skill in the art to which the claimed subject matter belongs.

Unless otherwise indicated, conventional methods of mass spectroscopy, NMR, HPLC, protein chemistry, biochemistry, recombinant DNA techniques and pharmacology, within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed of conventional methods well known in the art and as described in various general and more specific references that are cited and discussed throughout the present specification.

The term "alkyl" refers to an aliphatic hydrocarbon group, which may have branched or straight chain. Depending on the structure, an alkyl group can be a monoradical or a diradical (i.e., an alkylene group). In the invention, the alkyl group is preferable a "lower alkyl" having 1 to 8 carbon atoms, more preferably 1-6 carbon atoms or 1-4 carbon atoms. Typical alkyl groups include, but are not limited to, methyl, ethyl, propyl, isopropyl, butyl, isobutyl, tert-butyl, pentyl, hexyl, and the like.

"Alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

"Alkoxyalkyl" refers to an alkyl radical, as defined herein, substituted with an alkoxy group, as defined herein.

The term "aromatic" refers to a planar ring having a delocalized T-electron system containing 4n+2 T electrons, where n is an integer. Aromatic rings can be formed from five, six, seven, eight, nine, or more than nine atoms. Aromatics can be optionally substituted. The term "aromatic" includes both carbocylic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed from five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

"Alkyl(aryl)" means an alkyl radical, as defined herein, substituted with an aryl group, as defined herein. Non-limiting alkyl(aryl) groups include benzyl, phenethyl, and the like.

The term "cycloalkyl" refers to a monocyclic or polycyclic radical that contains only carbon and hydrogen. Cycloalkyl groups include groups having from 3 to 10 ring atoms. Depending on the structure, a cycloalkyl group can be a monoradical or a diradical (e.g., a cycloalkylene group). In the invention, the cycloalkyl group is preferably a cycloalkyl having 3 to 8 carbon atoms, and more preferably a "lower cycloalkyl" having 3 to 6 carbon atoms.

"Alkyl(cycloalkyl)" means an alkyl radical, as defined herein, substituted with a cycloalkyl group, as defined herein. Non-limiting alkyl(cycloalkyl) groups include cyclopropylmethyl, cyclobutylmethyl, cyclopentylmethyl, cyclohexylmethyl, and the like.

As used herein, the term "heteroalkyl" refers to an alkyl radical, as defined herein, in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

As used herein, the term "heterocycloalkyl" refers to a non-aromatic ring wherein one or more atoms forming the ring is a heteroatom selected from nitrogen, oxygen and sulfur. Heterocycloalkyl rings can be formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heteroaryl)" means an alkyl radical, as defined herein, substituted with a heteroaryl group, as defined herein.

The term "alkyl(heterocycloalkyl)" means an alkyl radical, as defined herein, substituted with a heterocycloalkyl group, as defined herein.

The term "halo" or "halogen" means fluoro, chloro, bromo and iodo.

The terms "haloalkyl", "haloalkoxy" and "haloheteroalkyl" include alkyl, alkoxy and heteroalkyl structures in which at least one hydrogen is replaced with a halogen atom. In certain embodiments in which two or more hydrogen atoms are replaced with halogen atoms, the halogen atoms are the same or different as one another.

As used herein, the term "cyano" refers to —CN group.

The term "ester" refers to a chemical moiety with formula —COOR, where R is selected from among alkyl, cycloalkyl, aryl, heteroaryl (bonded through a ring carbon) and heteroalicyclic (bonded through a ring carbon).

The term "amino" refers to —NH$_2$ group.

The term "alkylamino" refers to an amino substituent which is further substituted with one or two alkyl groups, specifically the group —NRR', wherein R and R' are each independently selected from the group consisting of hydrogen or lower alkyl, with the proviso that —NRR' is not —NH$_2$. The term "cycloalkylamino" refers to an amino substituent which is further substituted with one or two cycloalkyl as defined herein. The term "heteroalkylamino" refers to an amino substituent which is further substituted with one or two heteroalkyl as defined herein. The term "aralkylamino" herein refers to a group —NRR' wherein R is lower aralkyl and R' is hydrogen, lower alkyl, aryl or lower aralkyl. The term "aminoalkyl" refers to an alkyl substituent which is further substituted with one or more amino. The term "hydroxyalkyl" or "hydroxylalkyl" refers to an alkyl substituent which is further substituted with one or more hydroxyl. The term "cyanoalkyl" refers to refers to an alkyl substituent which is further substituted with one or more cyano. The term "alkylcarbonyl" refers to carbonyl which is further substituted with an alkyl. The term "alkylcarbonylalkyl" refers to alkyl which is further substituted with an alkylcarbonyl. The term "alkoxylcarbonyl" refers to carbonyl which is further substituted with an alkoxyl. The alkyl or aryl moiety of alkylamino, cycloalkylamino, heteroalkylamino, aralkylamino, aminoalkyl, hydroxyalkyl, cyanoalkyl, alkylcarbonyl, alkylcarbonylalkyl and alkoxylcarbonyl may be optionally substituted with one or more substituents.

The term "optionally substituted" or "substituted" means that the group mentioned may be substituted with one or more additional group(s) individually and independently selected from alkyl, cycloalkyl, aryl, heteroaryl, hydroxy, alkoxy, cyano, halo, amide, nitro, haloalkyl, amino, amino-protecting groups and the like.

The term "Bruton's tyrosine kinase" as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog" as used herein, refers to orthologs of Bruton's tyrosine kinase, e.g., the orthologs from mouse (GenBank Acession No. AAB47246), dog (GenBank Acession No. XP_549139.), rat (GenBank Acession No. NP_001007799), chicken (GenBank Acession No. NP_989564), or zebra fish (GenBank Acession No. XP_698117), and fusion proteins of any of the foregoing that exhibit kinase activity towards one or more substrates of Bruton's tyrosine kinase (e.g. a peptide substrate having the amino acid sequence AVLESEEELYS-SARQ (SEQ ID NO:1)).

The term "homologous cysteine" as used herein refers to a cysteine residue found within a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. Other examples of kinases having homologous cysteines are shown in Table 1. See also the sequence alignments of tyrosine kinases (TK) published on the World Wide Web at kmase.com/human/kinome/phylogeny.html.

TABLE 1

A sequence comparison of Btk with other tyrosine kinases.

| # | 473 | 474 | 475 | 476 | 477 | 478 | 479 | 480 | 481 | 482 | 483 | SEQ ID NO. |
|---|---|---|---|---|---|---|---|---|---|---|---|---|
| BTK | I | T | E | Y | M | A | N | G | C | L | L | 2 |
| BMX | V | T | E | Y | M | A | R | G | C | L | L | 3 |
| TEC | V | T | E | F | M | E | R | G | C | L | L | 4 |
| TXK | V | T | E | F | M | E | N | G | C | L | L | 5 |
| ITK | V | F | E | F | M | E | H | G | C | L | S | 6 |
| EGFR | I | T | Q | L | M | P | F | G | C | L | L | 7 |
| ErbB2 | V | T | Q | L | M | P | Y | G | C | L | L | 8 |
| ErbB4 | V | T | Q | L | M | P | H | G | C | L | L | 9 |
| JAK3 | V | M | E | Y | L | P | S | G | C | L | R | 10 |
| BLK | V | T | E | Y | L | P | S | G | C | L | L | 11 |
| LCK | I | T | E | Y | M | E | N | G | S | L | V | 12 |
| LYN | I | T | E | Y | M | A | K | G | S | L | L | 13 |
| SYK | V | M | E | M | A | E | L | G | P | L | N | 14 |

The terms "inhibits", "inhibiting", or "inhibitor" mentioned in connection with a kinase, as referred to herein, refer to inhibition of phosphotransferase activity.

The term "irreversible inhibitor" as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor" as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or other cysteine) of Btk or a cysteine residue in the homologous corresponding position of another tyrosine kinase (homologous cysteine), as shown in Table 1.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites. The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "target protein" refers to a protein molecule or a portion of a protein capable of being selectively bound by a compound. In certain embodiments, a target protein is Btk. In some embodiments, the target protein is Btk. In some embodiments, the target protein is Jak3. In some embodiments, the target protein is BMX. In some embodiments, the target protein is EGFR.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The Bruton's Tyrosine Kinase Inhibitor of the Present Invention

The present invention relates to an inhibitor of Bruton's tyrosine kinase. Specifically, the compound of the present invention comprises the compound formula (I), or a pharmaceutically acceptable salt, solvate, ester, acid, metabolite or prodrug thereof:

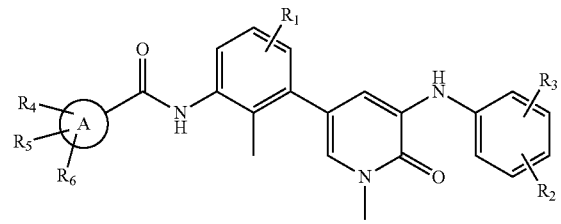

formula (I)

wherein, ring A represents any monocyclic or fused-ring group selected from the group consisting of phenyl, thienyl, benzothiophenyl and tetrahydrobenzothiophenyl; each of $R_1$ and $R_2$ is independently selected from the group consisting of hydrogen,

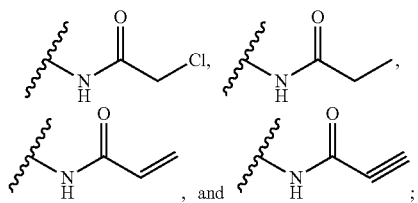

$R_3$ is selected from the group consisting of hydrogen, C1-C8 alkyl, halo, hydroxy, nitro, cyano, C1-C8 haloalkyl, amino, C1-C8 alkylamino, —(CO)—$R_7$, heterocycloalkyl optionally substituted with $R_8$, and heteroaryl optionally substituted with $R_8$;

each of $R_4$, $R_5$ and $R_6$ is independently selected from the group consisting of hydrogen, halo, hydroxy, amino, nitro, cyano, C1-C8 alkyl, C3-C8 cycloalkyl, C1-C8 haloalkyl, C1-C8 alkoxy, C1-C8 alkylamino, heterocycloalkyl, aryl and heteroaryl, or any adjacent two of $R_4$, $R_5$ and $R_6$ together form C3-C8 cycloalkyl or heterocycloalkyl;

$R_7$ is selected from the group consisting of C1-C8 alkoxy, C1-C8 alkylamino, C3-C8 cycloalkylamino, C2-C8 heteroalkylamino, C3-C8 heterocycloalkylamino, and heterocycloalkyl optionally substituted with halo, hydroxy, amino, nitro, cyano, C1-C8 alkyl, C1-C8 alkoxy, or amino protecting group; $R_8$ is selected from the group consisting of C1-C8 alkyl, C1-C8 alkoxy, C1-C8 alkylamino or C2-C8 alkanoyl.

In certain embodiments, the above aryl is preferably phenyl; the above heteroaryl is preferably pyrazolyl; each of the above heterocycloalkyl is preferably independently selected from the group consisting of piperazinyl, morpholinyl, piperidinyl, pyrrolidinyl, tetrahydropyranyl, dioxolanyl, and dioxanyl.

In a preferred embodiment, the amino protecting group is independently selected from the group consisting of pivaloyl (Piv), tert-butoxycarbonyl (Boc), benzyloxycarbonyl (Cbz), 9-fluorenylmethoxycarbonyl (FMOC), benzyl (Bn), p-methoxybenzyl (PMP), allyloxycarbonyl (Alloc), and trifluoroacetyl (Tfa).

In a further preferred embodiment, $R_3$ is selected from the group consisting of hydrogen, C1-C6 alkyl (such as methyl and the like), C1-C6 alkylamino (such as dimethylamino and the like), —(CO)—$R_7$, heterocycloalkyl (such as piperazinyl, morpholinyl, piperidinyl and pyrrolidinyl and the like) optionally substituted with $R_8$, and heteroaryl (such as pyrazolyl) optionally substituted with $R_8$; and $R_7$ is selected from the group consisting of C1-C6 alkoxyl (such as methoxy and the like), C1-C6 alkylamino (such as dimethylamino and the like), C3-C6 cycloalkylamino (such as cyclopropylamino and the like), C2-C6 heteroalkylamino (such as N-(2-methoxyethyl)amino, N,N-bis(2-ethoxyethyl) amino and the like), C3-C6 heterocycloalkylamino (such as tetrahydropyran-4-ylamino and the like), and optionally substituted heterocycloalkyl (such as pyrrolidinyl; piperidinyl the heterocyclic carbon(s) of which is optionally substituted with hydroxy or alkoxy; morpholinyl; piperazinyl with its nitrogen(s) being optionally substituted with alkyl or Boc, and the like); $R_8$ is selected from the group consisting of C1-C6 alkyl (such as methyl, ethyl, isopropyl and the like), C1-C6 alkoxyl (such as methoxy and the like), C2-C6 alkanoyl (such as acetyl and the like), and C1-C8 alkylamino (such as dimethylamino and the like).

In other preferred embodiments, each of $R_4$, $R_5$ and $R_6$ is independently selected from the group consisting of hydrogen, C1-C6 alkyl (such as methyl, ethyl, isopropyl, tert-butyl and the like), C3-C6 cycloalkyl (such as cyclopropyl and the like), C1-C6 haloalkyl (such as trifluoromethyl and the like), C1-C6 alkoxyl (such as methoxy and the like), C1-C6 alkylamino (such as dimethylamino and the like), heterocycloalkyl (such as morpholinyl, pyrrolidinyl and the like), or any adjacent two of $R_4$, $R_5$ and $R_6$ together form C3-C6 cycloalkyl (such as cyclohexyl and the like) or heterocycloalkyl (such as dioxolanyl, dioxanyl and the like).

In another aspect, the compound of the present invention comprises the compound of formula (Ia), or a pharmaceutically acceptable salt, solvate, ester, acid, metabolite or prodrug thereof:

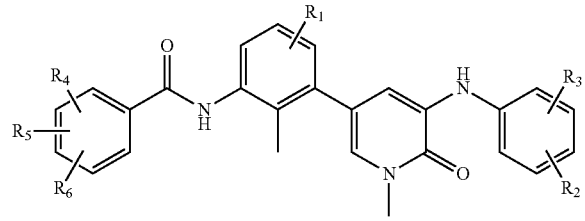

formula (Ia)

wherein, $R_1$, $R_2$, $R_3$, $R_4$, $R_5$ and $R_6$ are defined as above.

More preferably, each of $R_1$ and $R_2$ is independently selected from the group consisting of hydrogen,

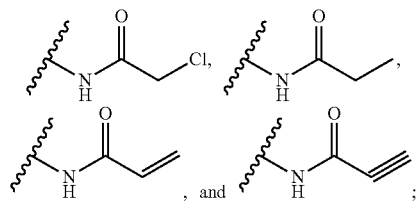

$R_3$ is selected from the group consisting of hydrogen, C1-C8 alkyl, halo, hydroxy, nitro, cyano, C1-C8 haloalkyl, amino, C1-C8 alkylamino, —(CO)—$R_7$, and heterocycloalkyl optionally substituted with $R_8$;

each of $R_4$, $R_5$ and $R_6$ is independently selected from the group consisting of hydrogen, halo, hydroxy, amino, nitro, cyano, C1-C8 alkyl, C3-C8 cycloalkyl, C1-C8 haloalkyl, C1-C8 alkoxy, C1-C8 alkylamino, heterocycloalkyl, aryl and heteroaryl, or any adjacent two of $R_4$, $R_5$ and $R_6$ together form C3-C8 cycloalkyl or heterocycloalkyl;

$R_7$ is selected from the group consisting of C1-C8 alkoxy, C1-C8 alkylamino, C3-C8 cycloalkylamino, C2-C8 heteroalkylamino, C3-C8 heterocycloalkylamino, and heterocycloalkyl optionally substituted with halo, hydroxy, amino, nitro, cyano, C1-C8 alkyl, C1-C8 alkoxy, or amino protecting group;

$R_8$ is selected from the group consisting of C1-C8 alkyl.

In a preferred embodiment, the amino protecting group is independently selected from the group consisting of pivaloyl (Piv), tert-butoxycarbonyl (Boc), benzyloxycarbonyl (Cbz), 9-fluorenylmethoxycarbonyl (FMOC), benzyl (Bn), p-methoxybenzyl (PMP), allyloxycarbonyl (Alloc), and trifluoroacetyl (Tfa).

In a further preferred embodiment, $R_3$ is selected from the group consisting of hydrogen, C1-C6 alkyl (such as methyl and the like), —(CO)—$R_7$, and heterocycloalkyl optionally substituted with C1-C6 alkyl (such as piperazinyl optionally substituted with methyl or ethyl, and morpholinyl, and the like); and $R_7$ is selected from the group consisting of C1-C6 alkoxyl (such as methoxy and the like), C1-C6 alkylamino (such as dimethylamino and the like), C3-C6 cycloalkylamino (such as cyclopropylamino and the like), C2-C6 heteroalkylamino (such as N-(2-methoxyethyl)amino, N,N-bis(2-ethoxyethyl)amino and the like), C3-C6 heterocycloalkylamino (such as tetrahydropyran-4-ylamino and the like), and optionally substituted heterocycloalkyl (such as pyrrolidinyl; piperidinyl with its heterocyclic carbon(s) being optionally substituted with hydroxyl or alkoxyl, morpholinyl; piperazinyl with its nitrogen(s) being optionally substituted with alkyl or Boc, and the like).

In other preferred embodiments, each of $R_4$, $R_5$ and $R_6$ is independently selected from the group consisting of hydrogen, C1-C6 alkyl (such as methyl, ethyl, isopropyl, tert-butyl and the like), C3-C6 cycloalkyl (such as cyclopropyl and the like), C1-C6 haloalkyl (such as trifluoromethyl and the like), C1-C6 alkoxyl (such as methoxy and the like), C1-C6 alkylamino (such as dimethylamino and the like), heterocycloalkyl (such as morpholinyl, pyrrolidinyl and the like), or any adjacent two of $R_4$, $R_5$ and $R_6$ together form C3-C6 cycloalkyl (such as cyclohexyl and the like) or heterocycloalkyl (such as dioxolanyl, dioxanyl and the like).

In a further preferred embodiment, the compound of the present invention comprises the compound of formula (IIa), or a pharmaceutically acceptable salt, solvate, ester, acid, metabolite or prodrug thereof:

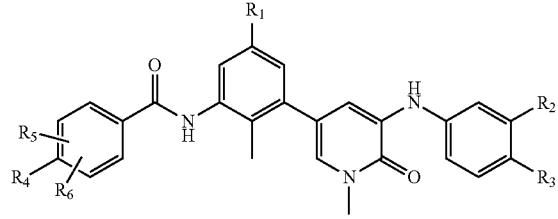

formula (IIa)

wherein, $R_1$, $R_2$, $R_3$, $R_4$, $R_5$ and $R_6$ are defined as above.

Preferably, in the compound of formula (IIa), $R_1$ is hydrogen; $R_2$ is selected from the group consisting of

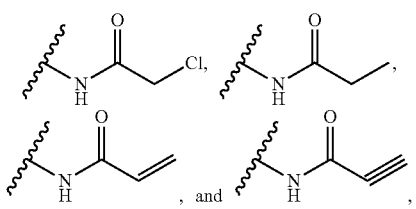

and $R_2$ is more preferably

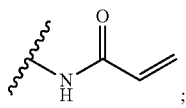 [SMILES: *NC(=O)C=C]
;

$R_3$ is —(CO)—$R_7$, and $R_7$ is selected from the group consisting of C1-C6 alkylamino, C3-C6 cycloalkylamino, C3-C6 heterocycloalkylamino, and optionally substituted heterocycloalkyl, and $R_7$ is more preferably morpholinyl; or $R_3$ is heterocycloalkyl optionally substituted with C1-C6 alkyl, and is more preferably piperazinyl with its nitrogen(s) being substituted with methyl or ethyl; $R_4$ is selected from the group consisting of C1-C6 alkyl, C1-C6 alkylamino, and heterocycloalkyl, and each of $R_5$ and $R_6$ is hydrogen, or any adjacent two of $R_4$, $R_5$ and $R_6$ together form C3-C6 cycloalkyl or heterocycloalkyl, and $R_4$ is more preferably selected from the group consisting of methyl, isopropyl, tert-butyl, dimethylamino, and pyrrolidyl, or $R_4$, together with adjacent $R_5$ or $R_6$, forms cyclohexyl or dioxanyl.

In another aspect, the compound of the present invention comprises the compound of formula (Ib), or a pharmaceutically acceptable salt, solvate, ester, acid, metabolite or prodrug thereof:

formula (Ib)

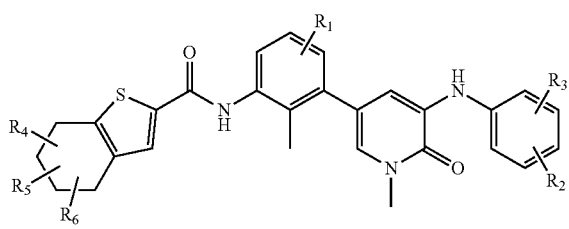

wherein, $R_1$, $R_2$, $R_3$, $R_4$, $R_5$ and $R_6$ are defined as above.

In a further preferred embodiment, the compound of the present invention comprises the compound of formula (IIb), or a pharmaceutically acceptable salt, solvate, ester, acid, metabolite or prodrug thereof:

formula (IIb)

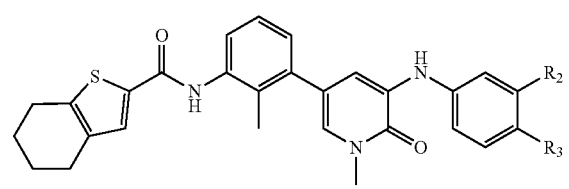

wherein, $R_2$ and $R_3$ are defined as above.

Preferably, $R_2$ is selected from the group consisting of

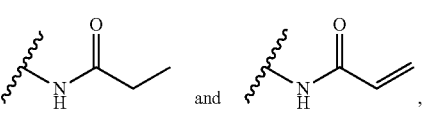

and $R_2$ is more preferably

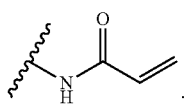 [SMILES: *NC(=O)C=C]
.

Preferably, $R_3$ is selected from the group consisting of C1-C6 alkylamino (such as dimethylamino and the like), —(CO)—$R_7$, heterocycloalkyl optionally substituted with $R_8$ (such as piperazinyl, morpholinyl, pyrrolidyl, piperidyl), and heteroaryl (such as pyrazolyl and the like); $R_7$ is selected from the group consisting of heterocycloalkyl (such as morpholinyl, pyrrolidyl); $R_8$ is selected from the group consisting of C1-C6 alkyl (such as methyl, ethyl, isopropyl), C1-C6 alkoxyl (such as methoxy), C1-C6 alkylamino (such as dimethylamino), or C2-C6 alkanoyl (such as acetyl). More preferably, $R_3$ is selected from the group consisting of —(CO)-morpholinyl; pyrazolyl; piperazinyl optionally substituted with methyl, ethyl, or isopropyl; and piperidyl optionally substituted with dimethylamino.

In other aspects, the compound of the present invention comprises the compound of formula (Ic), or a pharmaceutically acceptable salt, solvate, ester, acid, metabolite or prodrug thereof:

formula (Ic)

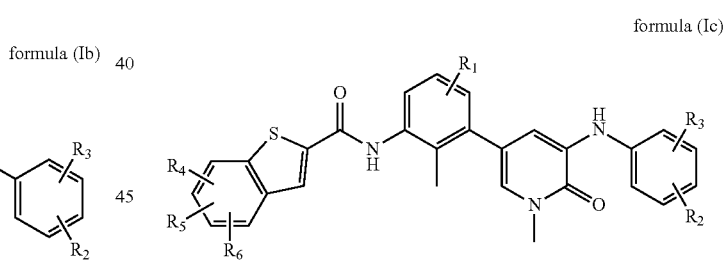

wherein, $R_1$, $R_2$, $R_3$, $R_4$, $R_5$ and $R_6$ are defined as above.

In a further preferred embodiment, the compound of the present invention comprises the compound of formula (IIc), or a pharmaceutically acceptable salt, solvate, ester, acid, metabolite or prodrug thereof:

formula (IIc)

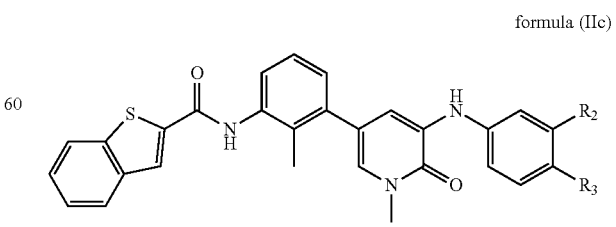

wherein, $R_2$ and $R_3$ are defined as above.

Preferably, R₂ is

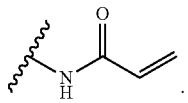 [SMILES: *NC(=O)C=C]

Preferably, R₃ is selected from the group consisting of C1-C6 alkylamino (such as dimethylamino and the like), —(CO)—R₇, heterocycloalkyl optionally substituted with R₈ (such as piperazinyl, morpholinyl, pyrrolidyl, piperidyl), and heteroaryl (such as pyrazolyl and the like); R₇ is selected from the group consisting of heterocycloalkyl (such as morpholinyl, pyrrolidyl); R₈ is selected from the group consisting of C1-C6 alkyl (such as methyl, ethyl, isopropyl), C1-C6 alkoxyl (such as methoxy), C1-C6 alkylamino (such as dimethylamino), or C2-C6 alkanoyl (such as acetyl). More preferably, R₃ is selected from the group consisting of —(CO)-morpholinyl; piperazinyl optionally substituted with methyl, ethyl, or isopropyl; and piperidyl optionally substituted with dimethylamino.

In other aspects, the compound of the present invention comprises the compound of formula (Id), or a pharmaceutically acceptable salt, solvate, ester, acid, metabolite or prodrug thereof:

formula (Id)

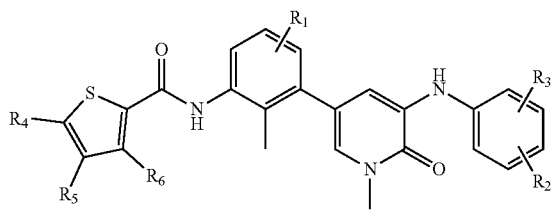

wherein, R₁, R₂, R₃, R₄, R₅ and R₆ are defined as above.

In a further preferred embodiment, the compound of the present invention comprises the compound of formula (IId), or a pharmaceutically acceptable salt, solvate, ester, acid, metabolite or prodrug thereof:

formula (IId)

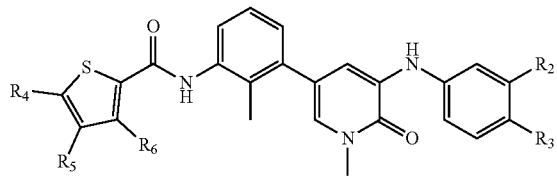

wherein, R₂, R₃, R₄, R₅ and R₆ are defined as above.
Preferably, R₂ is

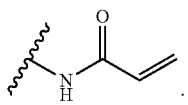 [SMILES: *NC(=O)C=C]

Preferably, R₃ is selected from the group consisting of C1-C6 alkylamino (such as dimethylamino and the like), —(CO)—R₇, heterocycloalkyl optionally substituted with R₈ (such as piperazinyl, morpholinyl, pyrrolidyl, piperidyl), and heteroaryl (such as pyrazolyl and the like); R₇ is selected from the group consisting of heterocycloalkyl (such as morpholinyl, pyrrolidyl); R₈ is selected from the group consisting of C1-C6 alkyl (such as methyl, ethyl, isopropyl), C1-C6 alkoxyl (such as methoxy), C1-C6 alkylamino (such as dimethylamino), or C2-C6 alkanoyl (such as acetyl). More preferably, R₃ is —(CO)-morpholinyl.

Preferably, each of R₄, R₅ and R₆ is independently selected from the group consisting of hydrogen and C1-C6 alkyl (such as methyl). More preferably, R₄ is methyl and each of R₅ and R₆ is hydrogen, or R₅ is methyl and each of R₄ and R₆ is hydrogen.

Further preferably, the present invention relates to an irreversible inhibitor of Bruton's tyrosine kinase, which comprises the compound of above formula (I), (Ia), (IIa), (Ib), (IIb), (Ic), (IIc), (Id) or (IId), or a pharmaceutically acceptable salt, solvate, ester, acid, metabolite or prodrug thereof, wherein R₁, R₃, R₄, R₅ and R₆ are defined as above, R₂ is selected from the group consisting of

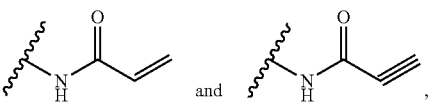

and R₂ is more preferably

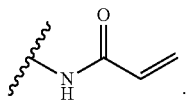

Described herein are compounds that inhibit tyrosine kinases such as Btk activity. The pharmaceutically acceptable salts, solvates, esters, acids, pharmaceutically active metabolites and prodrugs of these compounds are also described herein.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, malic acid, citric acid, succinic acid, maleic acid, tartaric acid, fumaric acid, trifluoroacetic acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 4-methylbicyclo-[2.2.2]oct-2-ene-1-carboxylic acid, 2-naphthalenesulfonic acid, tertiary butylacetic acid, glucoheptonic acid, 4,4'-methylenebis-(3-hydroxy-2-ene-1-carboxylic acid), 3-phenylpropionic acid, trimethylacetic acid, lauryl sulfuric acid, gluconic acid, glutamic acid, salicylic acid, hydroxynaphthoic acid, stearic acid, muconic acid, and the like; (2) salts formed when an acidic proton present in the parent compound either is replaced by a metal ion, e.g., an alkali metal ion (e.g.

lithium, sodium, potassium), an alkaline earth ion (e.g. magnesium, or calcium), or an aluminum ion; or coordinates with an organic base. Acceptable organic bases include ethanolamine, diethanolamine, triethanolamine, trimethylamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

The screening and characterization of the pharmaceutically acceptable salts, polymorphs and/or solvates may be accomplished using a variety of techniques including, but not limited to, thermal analysis, x-ray diffraction, spectroscopy, and microscopy. The various spectroscopic techniques used include, but are not limited to, Raman, FTIR, UVIS, and NMR (liquid and solid state). The various microscopy techniques include, but are not limited to, IR microscopy and Raman microscopy.

The Pharmaceutical Composition of the Present Invention

The present application further provides a pharmaceutical composition, containing at least one compound of formula (I), (Ia), (IIa), (Ib), (IIb), (Ic), (IIc), (Id) or (IId) or a pharmaceutically acceptable salt, solvate, ester, acid, pharmaceutically active metabolite or prodrug of the compound, and a pharmaceutically acceptable carrier or excipient, and optionally other therapeutic agents.

In the course of treatment, it may be used alone or in combination with one or more other therapeutic agents. The medicament comprising a compound of the invention may be administered to a patient through at least one of injection, oral, inhalation, rectal and transdermal administration. Other therapeutic agents may be selected from the following: immunosuppressants (e.g., tacrolimus, cyclosporin, rapamycin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, fluoxyprednisolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), allergy vaccines, antihistamines, antileukotrienes, β-agonists, theophylline, anticholinergics, or other selective kinase inhibitors (e.g., mTOR inhibitors, c-Met inhibitors) or her2 antibodies. In addition, the other therapeutic agents may also be Rapamycin, Crizotinib, Tamoxifen, Raloxifene, Anastrozole, Exemestane, Letrozole, Herceptin™ (Trastuzumab), Gleevec™ (Imatinib), Taxol™ (Paclitaxel), Cyclophosphamide, Lovastatin, Minosine, Cytarabine, 5-Fluorouracil (5-FU), Methotrexate (MTX), Taxotere™ (Docetaxel), Zoladex™ (Goserelin), Vincristine, Vinblastine, Nocodazole, Teniposide, Etoposide, Gemzar™ (Gemcitabine), Epothilone, Navelbine, Camptothecin, Daunonibicin, Dactinomycin, Mitoxantrone, Amsacrine, Doxorubicin (Adriamycin), Epirubicin or Idarubicin. Alternatively, other therapeutic agents may be cytokines such as G-CSF (Granulocyte-Colony Stimulating Factor). Alternatively, other therapeutic agents may be used in combination for the same treatment regimen, including but not limited to, CMF (Cyclophosphamide, Methotrexate and 5-Fluorouracil), CAF (Cyclophosphamide, Adriamycin and 5-Fluorouracil), AC (Adriamycin and Cyclophosphamide), FEC (5-Fluorouracil, Epirubicin and Cyclophosphamide), ACT or ATC (Adriamycin, Cyclophosphamide and Paclitaxel) or CMFP (Cyclophosphamide, Methotrexate, 5-Fluorouracil and Prednisone).

In embodiments of the present invention, when a patient is treated in accordance with the invention, the amount of a given agent will vary depending upon factors such as the particular dosing regimen, the type of the disease or condition and its severity, the identity (e.g., weight) of the subject or host in need of treatment, but can be routinely determined in a manner known in the art according to the particular circumstances surrounding the case, including, e.g., the specific agent being administered, the route of administration, the condition being treated, and the subject or host being treated. In general, doses employed for adult human treatment will typically be in the range of 0.02-5000 mg per day, such as from about 1-1500 mg per day. The desired dose may conveniently be presented in a single dose or as divided doses administered simultaneously (or over a short period of time) or at appropriate intervals, for example as two, three, four or more sub-doses per day. It will be appreciated by those skilled in the art that, although the above dosage ranges are given, the specific effective amounts may be appropriately adjusted depending on the condition of the patient and the judgment of the practitioner.

The compound of formula (I), (Ia), (IIa), (Ib), (IIb), (Ic), (IIc), (Id) or (IId) of the present invention can irreversibly inhibit Btk, and can be used in the treatment of patients suffering from conditions or diseases that are involved in or mediated by Bruton's tyrosine kinase, including but not limited to, cancers, autoimmune diseases and other inflammatory diseases. The conditions or diseases are selected from the group consisting of B-cell lymphoma, sarcoma, lymphoma, diffuse large B-cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B-cell lymphoma, nodal marginal zone B-cell lymphoma, mantle cell lymphoma, mediastinal (thymic) large B-cell lymphoma, intravascular large B-cell lymphoma, primary effusion lymphoma, Burkitt lymphoma, leukemia, lymphomatoid granulomatosis, breast ductal carcinoma, lobular carcinoma, adenocarcinoma, small cell lung cancer, non-small cell lung cancer, melanoma, B-cell lymphoma, sarcoma, lymphoma, B cell proliferative diseases, B cell proliferative diseases, or the like, or the combination thereof. It is particularly preferred for the treatment of acute myeloid leukemia (AML), chronic lymphocytic leukemia (CLL), and B-cell proliferative disease such as chronic lymphocytic lymphoma, diffuse large B-cell lymphoma (DLBCL), follicular lymphoma or chronic lymphocytic leukemia, or the like, and the combination thereof.

Preparation of the Compounds

Compounds of formula (I), (Ia), (IIa), (Ib), (IIb), (Ic), (IIc), (Id) or (IId) may be synthesized using standard synthetic techniques known to those of skill in the art or using methods known in the art in combination with methods described herein. In addition, solvents, temperatures and other reaction conditions presented herein may vary according to those of skill in the art. As a further guide the following synthetic methods may also be utilized.

The reactions can be employed in order to provide the compounds described herein or they may be used to synthesize fragments which are subsequently joined by the methods described herein and/or known in the art.

The compounds described herein can be modified using various electrophiles or nucleophiles to form new functional groups or substituents. Table 2 lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 2

Examples of Covalent Linkages and Precursors Thereof

| Covalent LinkageProduct | Electrophile | Nucleophile |
|---|---|---|
| carboxamides | activated esters | amines/anilines |
| carboxamides | acyl azides | amines/anilines |
| carboxamides | acyl halides | amines/anilines |
| esters | acyl halides | alcohols/phenols |
| esters | acyl nitriles | alcohols/phenols |
| carboxamides | acyl nitriles | amines/anilines |
| imines | aldehydes | amines/anilines |
| hydrazones | aldehydes or ketones | hydrazines |
| oximes | aldehydes or ketones | hydroxylamines |
| alkyl amines | alkyl halides | amines/anilines |
| esters | alkyl halides | carboxylic acids |
| thioethers | alkyl halides | thiols |
| esters | alkyl halides | alcohols/phenols |
| thioethers | alkyl sulfonates | thiols |
| esters | alkyl sulfonates | carboxylic acids |
| ethers | alkyl sulfonates | alcohols/phenols |
| esters | anhydrides | alcohols/phenols |
| carboxamides | anhydrides | amines/anilines |
| thiophenols | aryl halides | thiols |
| aryl amines | aryl halides | amines |
| thioethers | azindine | thiols |
| boronate esters | boronates | glycols |
| carboxamides | carboxylic acids | amines/anilines |
| esters | carboxylic acids | alcohols |
| hydrazines | hydrazides | carboxylic acids |
| N-acylureas or anhydrides | carbodiimides | carboxylic acids |
| esters | diazoalkanes | carboxylic acids |
| thioethers | epoxids | thiols |
| thioethers | haloacetamides | thiols |
| ammotriazines | halotriazines | amines/anilines |
| triazinyl ethers | halotriazines | alcohols/phenols |
| amidines | imido esters | amines/anilines |
| ureas | isocyanates | amines/anilines |
| urethanes | isocyanates | alcohols/phenols |
| thioureas | isothiocyanates | amines/anilines |
| thioethers | maleimides | thiols |
| phosphite esters | phosphoramidites | alcohols |
| silyl ethers | silyl halides | alcohols |

TABLE 2-continued

Examples of Covalent Linkages and Precursors Thereof

| Covalent LinkageProduct | Electrophile | Nucleophile |
|---|---|---|
| alkyl amines | sulfonate esters | amines/anilines |
| thioethers | sulfonate esters | thiols |
| esters | sulfonate esters | carboxylic acids |
| ethers | sulfonate esters | alcohols |
| sulfonamides | sulfonyl halides | amines/anilines |
| sulfonate esters | sulfonyl halides | phenols/alcohols |
| alkyl thiols | α,β-unsaturated esters | thiols |
| alkyl ethers | α,β-unsaturated esters | alcohols |
| alkyl amines | α,β-unsaturated esters | amines |
| alkyl thiols | vinyl sulfones | thiols |
| alkyl ethers | vinyl sulfones | alcohols |
| alkyl amines | vinyl sulfones | amines |
| vinyl sulfides | propargyl amides | thiols |

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

The starring materials used for the synthesis of the compounds described herein may be synthesized or can be obtained from commercial sources. The compounds described herein, and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

A non-limiting example of a synthetic approach towards the preparation of compounds of formula (I), (Ia), (IIa), (Ib), (IIb), (Ic), (IIc), (Id) or (IId) is shown in Scheme I.

Scheme I

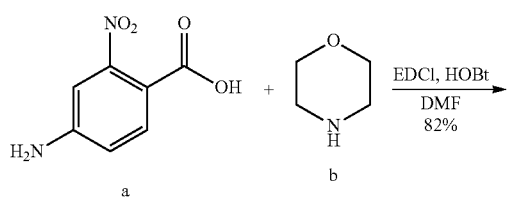

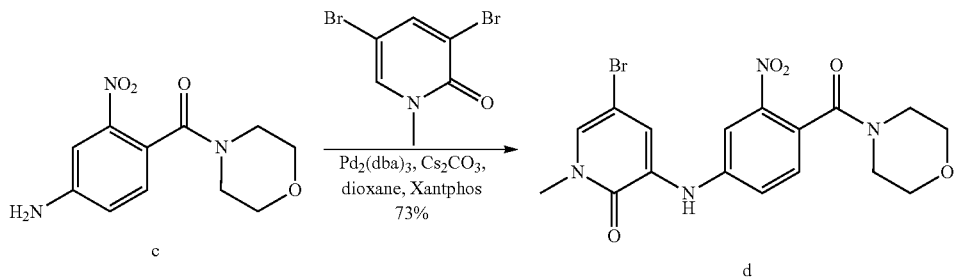

-continued
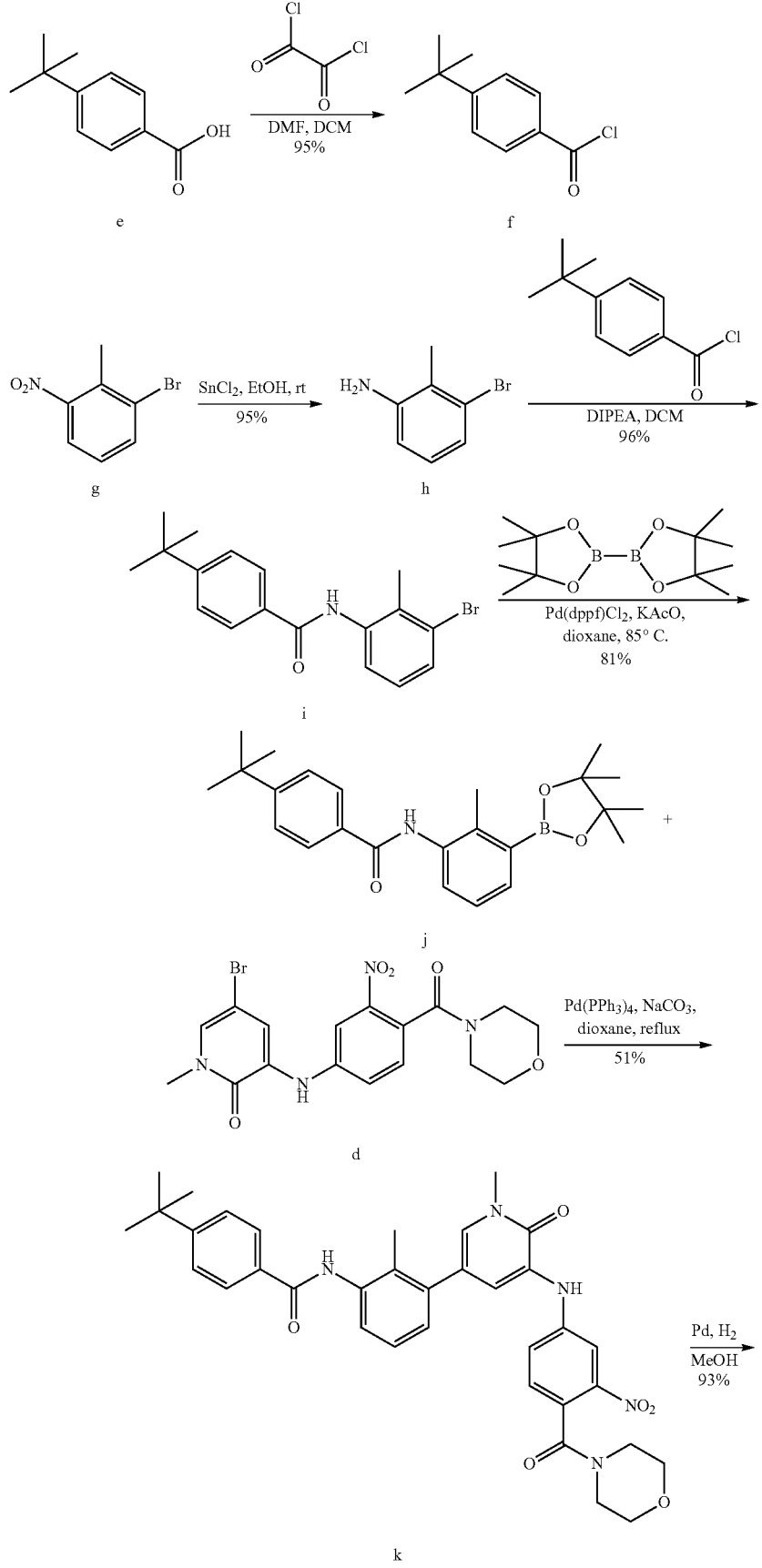

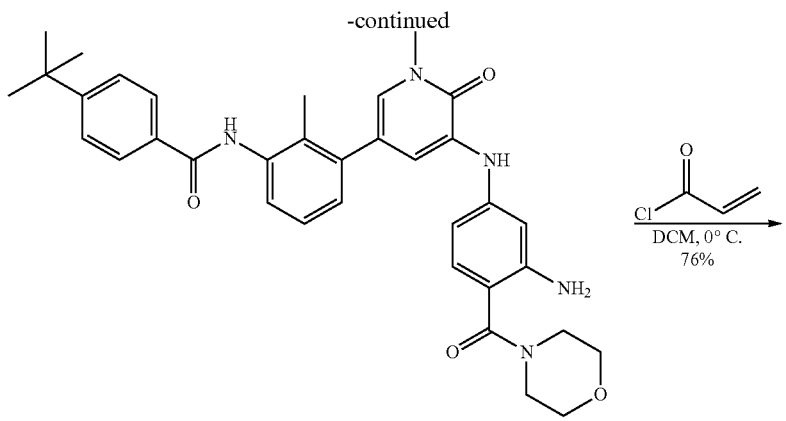

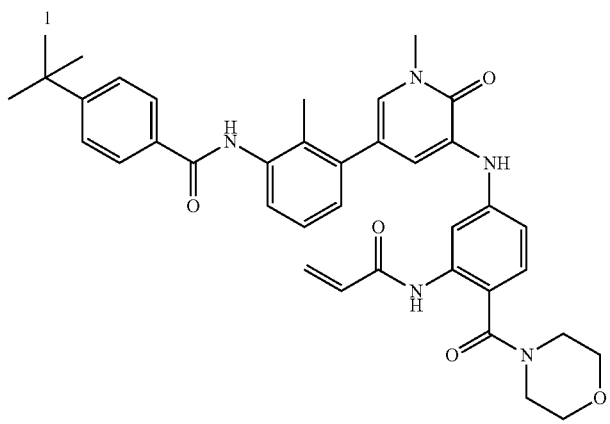

Example 1

Synthesis of Compound 1 N-(3-(5-((3-acrylamide-4-(morpholin-4-carbonyl)phenyl)amino)-1-methyl-6-oxo-1,6-dihydropyridin-3-yl)-2-methylphenyl)-4-(tert-butyl)benzamide Step 1: Synthesis of Compound c Compound a (1.00 g, 5.49 mmol) was added into N,N-dimethylformamide (DMG), and then carbodiimide (EDCl) (2.10 g, 10.95 mmol) and 1- hydroxybenzotriazole HOBt (0.74 g, 5.49 mmol) was added and the resultant was stirred under room temperature for 30 minutes, and further added with Compound b (2.40 ml, 27.45 mmol). The mixture was stirred for 8 hours under room temperature. Rotary evaporation was performed to remove N,N-dimethlformamide (DMF). After addition of water, extraction with ethyl acetate was performed three times and then the organic phase was washed with a saturated sodium chloride solution once. The organic phase was dried over anhydrous magnesium sulfate. After filtration, the filtrate was concentrated and subjected to column chromatography to give Compound c (1.13 g, 4.5 mmol) at a yield of 82%.

Step 2: Synthesis of Compound d:

Compound c (1.00 g, 3.98 mmol), 1,4-dioxane (15 ml), 4,5-bisdiphenylphosphino-9,9-dimethylxanthene (346 mg, 0.597 mmol), tris(dibenzylideneacetone)dipalladium (Pd$_2$(dba)$_3$) (364 mg, 0.398 mmol), caesium carbonate (Cs$_2$CO$_3$) (3.89 g, 11.94 mmol), 3,5-dibromo-1-methylpyridin-2(1H)-one (1.27 g, 4.78 mmol) was sequentially added into a sealed tube. The mixture underwent reaction under the protection of argon at 120° C. for 8 hours. Rotary evaporation was performed to remove 1,4-dioxane, and extraction with dichloromethane was performed three times after addition of water. The organic phase was washed with a saturated sodium chloride solution once. The organic phase was dried over anhydrous magnesium sulfate. After filtration, the filtrate was concentrated and subjected to column chromatography to give Compound d (1.27 g, 2.9 mmol) at a yield of 73%.

Step 3: Synthesis of Compound f

To anhydrous dichloromethane Compound e (500 mg, 3.03 mmol), 20 µL N,N-dimethylformamide was added, and then oxalyl chloride was added slowly, and the resultant was stirred for 2 hours at room temperature. The mixture was dried under rotation to obtain Compound f (526 mg, 2.88 mmol) at a yield of 95%.

Step 4: Synthesis of Compound h

To ethanol Compound g (500 mg, 2.32 mmol) and tin dichloride hydrate (2.62 g, 11.63 mmol) was added and reaction was conducted for 3 hours at 80° C. Rotary evaporation was performed to remove ethanol, and then pH was adjusted to about 8 with saturated aqueous sodium bicarbonate. The resultant was filtered with Celite and the filter cake was washed with ethyl acetate, and the filtrate was collected and extracted with ethyl acetate three times. The filtrate was dried under rotation to obtain Compound h (410 mg, 2.20 mmol) at a yield of 95%.

Step 5: Synthesis of Compound i

To anhydrous dichloromethane Compound h (410 mg, 2.20 mmol), Compound f (409 mg, 2.20 mmol) and DIPEA (380 µL, 2.20 mmol) was added at 0° C., and the resultant was stirred for 1 hour. Reaction was quenched with addition of water and extraction was performed with dichloromethane. The organic phase was washed with a saturated sodium chloride solution once. The organic phase was dried over anhydrous magnesium sulfate. After filtration, the filtrate was concentrated and subjected to column chromatography to give Compound i (696 mg, 2.09 mmol) at a yield of 96%.

Step 6: Synthesis of Compound j

Compound i (600 mg, 1.80 mmol), 1,1-bis(diphenylphosphino)ferrocenedichloropalladium (147 mg, 0.18 mmol), potassium acetate (530 mg, 5.4 mmol), bis(pinacolato)diboron (914 mg, 3.6 mmol) was added into 1,4-dioxane (80 ml). Stirring was conducted under protection of argon for 8 hours at 90° C. Rotary evaporation was performed to remove 1,4-dioxane, and extraction with dichloromethane was performed three times after addition of water. The organic phase was washed with a saturated sodium chloride solution once. The organic phase was dried over anhydrous magnesium sulfate. After filtration, the filtrate was concentrated and subjected to column chromatography to give Compound j (554 mg, 1.46 mmol) at a yield of 81%.

Step 7: Synthesis of Compound k

Compound j (554 mg, 1.46 mmol), Compound d (638 mg, 1.46 mmol), tetrakis(triphenylphosphine)palladium (Pd (PPh$_3$)$_4$) (169 mg, 0.146 mmol), sodium carbonate (442 mg, 4.38 mmol), water (5 ml) was added into 1,4-dioxane (80 ml), and stirring was conducted under protection of argon for 8 hours at 100° C. Rotary evaporation was performed to remove 1,4-dioxane, and extraction with dichloromethane was performed three times after addition of water. The organic phase was washed with a saturated sodium chloride solution once. The organic phase was dried over anhydrous magnesium sulfate. After filtration, the filtrate was concentrated and subjected to column chromatography to give Compound k (454 mg, 0.745 mmol) at a yield of 51%.

Step 8: Synthesis of Compound I

Compound k (400 mg, 0.655 mmol), and palladium/carbon (40 mg) was added into methanol, and the resultant was stirred for 4 hours under hydrogen atmosphere at room temperature. After filtration with Celite and rotary drying of the filtrate, Compound I was obtained (353 mg, 0.609 mmol) at a yield of 93%.

Step 9: Synthesis of Compound 1

To anhydrous dichloromethane Compound I (50 mg, 0.086 mmol), acryloyl chloride (8.2 μL, 0.10 mmol) was added at 0° C., and also N,N-diisopropylethylamine (DIPEA) (15 ul, 0.086 mmol), and the resultant was stirred for 10 minutes. The reaction was quenched by adding water and extraction with dichloromethane was performed. The organic phase was washed with a saturated sodium chloride solution once. The organic phase was dried over anhydrous magnesium sulfate. After filtration, the filtrate was concentrated and subjected to column chromatography to give Compound 1 (41 mg, 0.065 mmol) at a yield of 76%. Exact Mass (calculated): 647.3108; MS(ESI) m/e (M+1)+: 648.3113; 1H NMR (400 MHz, DMSO-d6) δ 9.97-9.79 (m, 2H), 8.18-8.00 (m, 1H), 7.99-7.86 (m, 2H), 7.64-7.52 (m, 3H), 7.35 (d, J=7.6 Hz, 1H), 7.27 (t, J=7.6 Hz, 2H), 7.24-7.18 (m, 2H), 7.16 (s, 1H), 7.10 (d, J=8.3 Hz, 1H), 6.47 (dd, J=17.0, 10.2 Hz, 1H), 6.22 (d, J=16.8 Hz, 1H), 5.70 (d, J=10.5 Hz, 1H), 3.61 (s, 3H), 3.56 (s, 4H), 3.39 (s, 4H), 2.21 (s, 3H), 1.34 (s, 9H).

Example 2

Synthesis of Compound 2 N-(3-(5-((3-chloroacetamide-4-(morpholin-4-carbonyl)phenyl)amino)-1-methyl-6-oxo-1,6-dihydropyridin-3-yl)-2-methyl-phenyl)-4-(tert-butyl)benzamide

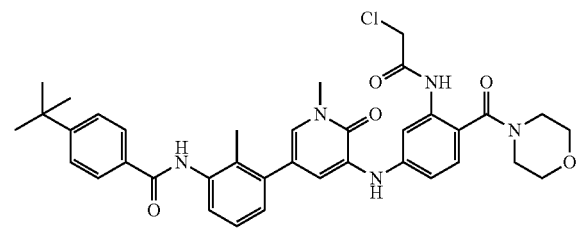 [SMILES: Cc1c(NC(=O)c2ccc(C(C)(C)C)cc2)cccc1-c1cc(Nc2ccc(C(=O)N3CCOCC3)c(NC(=O)CCl)c2)c(=O)n(C)c1]

Synthesis of Compound 2 was accomplished using a procedure similar to that described in Example 1. Exact Mass (calculated): 669.2718; MS(ESI) m/e (M+1)+: 670.2736.

Example 3

Synthesis of Compound 3 N-(3-(5-((3-acrylamide-4-(4-methylpiperazin-1-carbonyl)phenyl)amino)-1-methyl-6-oxo-1,6-dihydropyridin-3-yl)-2-methyl-phenyl)-4-(tert-butyl)benzamide

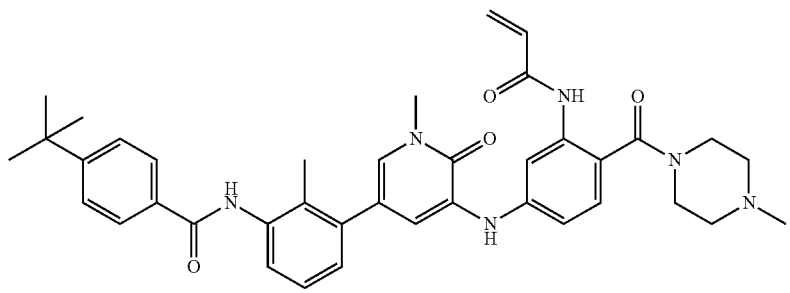 [SMILES: C=CC(=O)Nc1cc(Nc2cc(-c3cccc(NC(=O)c4ccc(C(C)(C)C)cc4)c3C)cn(C)c2=O)ccc1C(=O)N1CCN(C)CC1]

Synthesis of Compound 3 was accomplished using a procedure similar to that described in Example 1. Exact Mass (calculated): 660.3424; MS(ESI) m/e (M+1)+: 661.3454.

Example 4

Synthesis of Compound 4 N-(3-(5-((2-propynamide-4-(morpholin-4-carbonyl)phenyl)amino)-1-methyl-6-oxo-1,6-dihydropyridin-3-yl)-2-methylphenyl)-4-(tert-butyl)benzamide

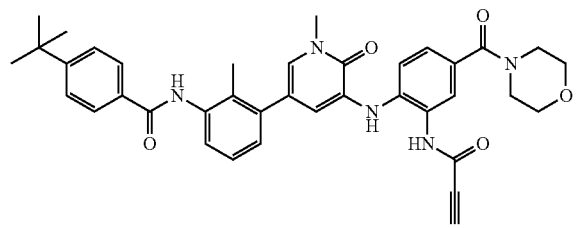 [SMILES: C#CC(=O)Nc1cc(C(=O)N2CCOCC2)ccc1Nc1cc(-c2cccc(NC(=O)c3ccc(C(C)(C)C)cc3)c2C)cn(C)c1=O]

Synthesis of Compound 4 was accomplished using a procedure similar to that described in Example 1. Exact Mass (calculated): 645.2951; MS(ESI) m/e (M+1)+: 646.3001.

Example 5

Synthesis of Compound 5 N-(3-(5-((3-chloroacetamide-4-(4-methylpiperazin-1-carbonyl)phenyl)amino)-1-methyl-6-oxo-1,6-dihydropyridin-3-yl)-2-methylphenyl)-4-(tert-butyl)benzamide

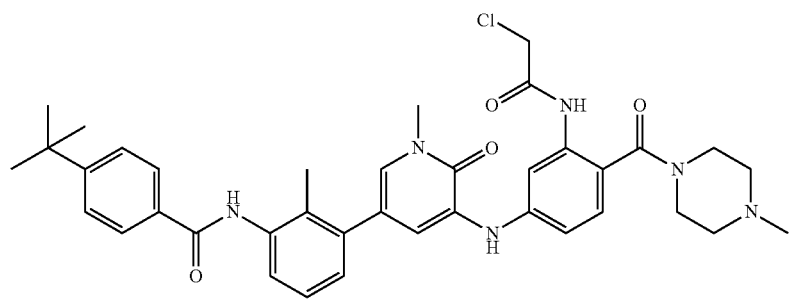 [SMILES: Cc1c(NC(=O)c2ccc(C(C)(C)C)cc2)cccc1-c1cc(Nc2ccc(C(=O)N3CCN(C)CC3)c(NC(=O)CCl)c2)c(=O)n(C)c1]

Synthesis of Compound 6 was accomplished using a procedure similar to that described in Example 1. Exact Mass (calculated): 682.3034; MS(ESI) m/e (M+1)+: 683.3064.

Example 6

Synthesis of Compound 6 N-(3-(5-((3-propanamide-4-(morpholin-4-carbonyl)phenyl)amino)-1-methyl-6-oxo-1,6-dihydropyridin-3-yl)-2-methylphenyl)-4-(tert-butyl)benzamide

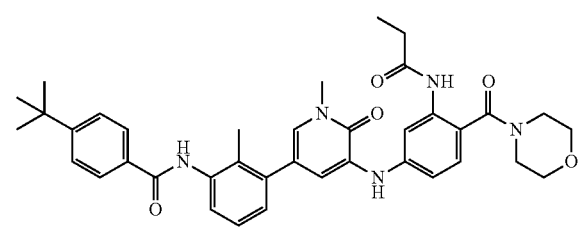 [SMILES: CCC(=O)Nc1cc(Nc2cc(-c3cccc(NC(=O)c4ccc(C(C)(C)C)cc4)c3C)cn(C)c2=O)ccc1C(=O)N1CCOCC1]

Synthesis of Compound 6 was accomplished using a procedure similar to that described in Example 1. Exact Mass (calculated): 649.3264; MS(ESI) m/e (M+1)+: 650.3234.

Example 7

Synthesis of Compound 7 4-(tert-butyl)-N-(5-(2-chloroacetamide)-2-methyl-3-(1-methyl-5-((4-(morpholin-4-carbonyl)phenyl)amino)-6-oxo-1,6-dihydropyridin-3-yl)phenyl)benzoylamide

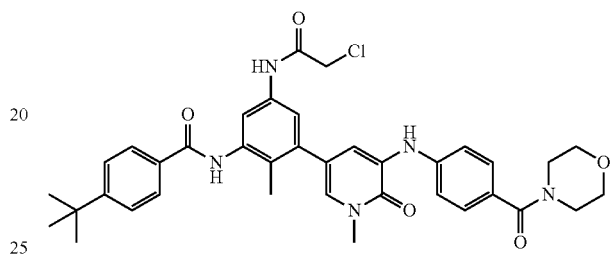

Synthesis of Compound 7 was accomplished using a procedure similar to that described in Example 1. Exact Mass (calculated): 669.2718; MS(ESI) m/e (M+1)+: 670.2738.

Example 8

Synthesis of Compound 8 4-(tert-butyl)-N-(5-(2-acrylamide)-2-methyl-3-(1-methyl-5-((4-(morpholin-4-carbonyl)phenyl)amino)-6-oxo-1,6-dihydropyridin-3-yl)phenyl)benzoylamide

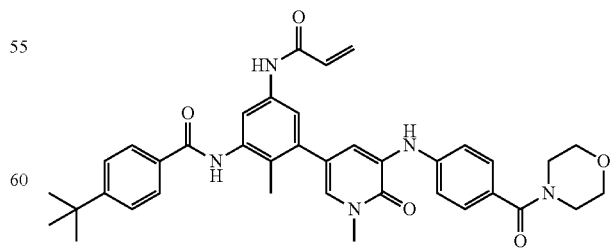

Synthesis of Compound 8 was accomplished using a procedure similar to that described in Example 1. Exact Mass (calculated): 647.3108; MS(ESI) m/e (M+1)+: 648.3118.

Example 9

Synthesis of Compound 9 N-(3-(5-((3-acrylamide-4-(morpholin-4-carbonyl)phenyl)amino)-1-methyl-6-oxo-1,6-dihydropyridin-3-)-2-methylphenyl)-4-(methyl)benzoylamide

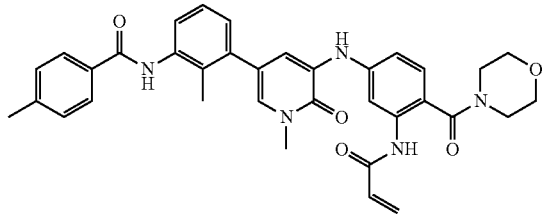 [SMILES: C=CC(=O)Nc1cc(Nc2cc(-c3cccc(NC(=O)c4ccc(C)cc4)c3C)cn(C)c2=O)ccc1C(=O)N1CCOCC1]

Synthesis of Compound 9 was accomplished using a procedure similar to that described in Example 1. Exact Mass (calculated): 605.2638; MS(ESI) m/e (M+1)+: 606.2648.

Example 10

Synthesis of Compound 10 N-(3-(5-((3-propanamide-4-(morpholin-4-carbonyl)phenyl)amino)-1-methyl-6-oxo-1,6-dihydropyridin-3-yl)-2-methylphenyl)-4-(methyl)benzoylamide

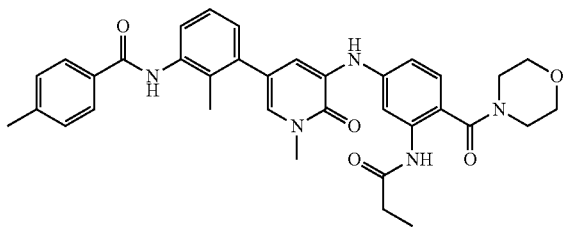 [SMILES: CCC(=O)Nc1cc(Nc2cc(-c3cccc(NC(=O)c4ccc(C)cc4)c3C)cn(C)c2=O)ccc1C(=O)N1CCOCC1]

Synthesis of Compound 10 was accomplished using a procedure similar to that described in Example 1. Exact Mass (calculated): 607.2795; MS(ESI) m/e (M+1)+: 608.2785.

Example 11

Synthesis of Compound 11 N-(3-(5-((3-chloroacetamide-4-(morpholin-4-carbonyl)phenyl)amino)-1-methyl-6-oxo-1,6-dihydropyridin-3-yl)-2-methylphenyl)-4-(methyl)benzoylamide

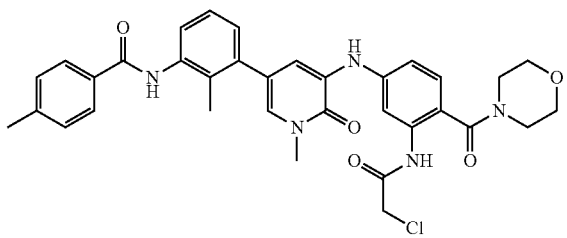 [SMILES: Cc1ccc(C(=O)Nc2cccc(-c3cc(Nc4ccc(C(=O)N5CCOCC5)c(NC(=O)CCl)c4)c(=O)n(C)c3)c2C)cc1]

Synthesis of Compound 11 was accomplished using a procedure similar to that described in Example 1. Exact Mass (calculated): 627.2248; MS(ESI) m/e (M+1)+: 628.2238.

Example 12

Synthesis of Compound 12 N-(3-(5-((3-acrylamide-4-(morpholin-4-carbonyl)phenyl)amino)-1-methyl-6-oxo-1,6-dihydropyridin-3-yl)-2-methylphenyl)benzoylamide

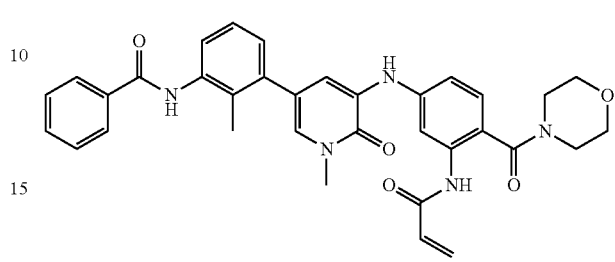

Synthesis of Compound 12 was accomplished using a procedure similar to that described in Example 1. Exact Mass (calculated): 591.2482; MS(ESI) m/e (M+1)+: 592.2442.

Example 13

Synthesis of Compound 13 N-(3-(5-((3-chloroacetamide-4-(morpholin-4-carbonyl)phenyl)amino)-1-methyl-6-oxo-1,6-dihydropyridin-3-yl)-2-methylphenyl)benzoylamide

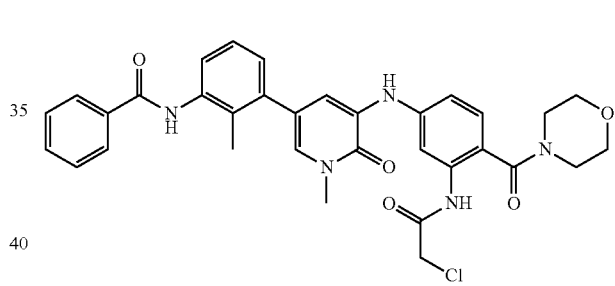

Synthesis of Compound 13 was accomplished using a procedure similar to that described in Example 1. Exact Mass (calculated): 613.2092; MS(ESI) m/e (M+1)+: 614.2102.

Example 14

Synthesis of Compound 14 N-(3-(5-((3-propanamide-4-(morpholin-4-carbonyl)phenyl)amino)-1-methyl-6-oxo-1,6-dihydropyridin-3-yl)-2-methylphenyl)benzoylamide

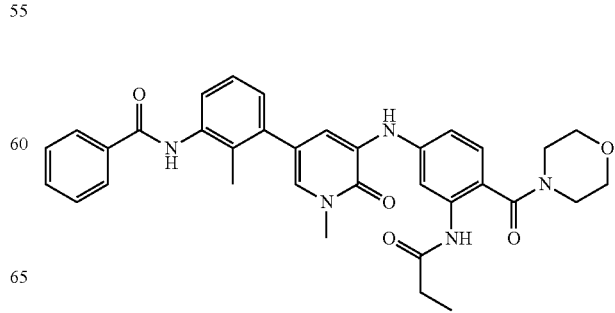

Synthesis of Compound 14 was accomplished using a procedure similar to that described in Example 1. Exact Mass (calculated): 593.2638; MS(ESI) m/e (M+1)+: 594.2653.

Example 15

Synthesis of Compound 15 N-(3-(5-((3-acrylamide-4-(morpholin-4-carbonyl)phenyl)amino)-1-methyl-6-oxo-1,6-dihydropyridin-3-yl)-2-methylphenyl)-4-morpholinbenzoylamide

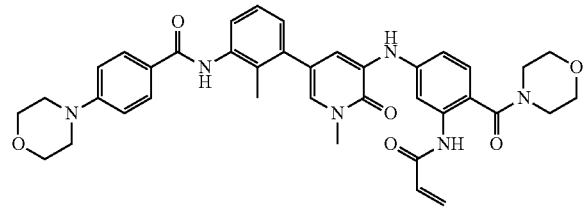 [SMILES: C=CC(=O)Nc1cc(Nc2cc(-c3cccc(NC(=O)c4ccc(N5CCOCC5)cc4)c3C)cn(C)c2=O)ccc1C(=O)N1CCOCC1]

Synthesis of Compound 15 was accomplished using a procedure similar to that described in Example 1. Exact Mass (calculated): 676.3009; MS(ESI) m/e (M+1)+: 677.3001.

Example 16

Synthesis of Compound 16 N-(3-(5-((3-chloroacetamide-4-(morpholin-4-carbonyl)phenyl)amino)-1-methyl-6-oxo-1,6-dihydropyridin-3-yl)-2-methylphenyl)-4-morpholinbenzoylamide

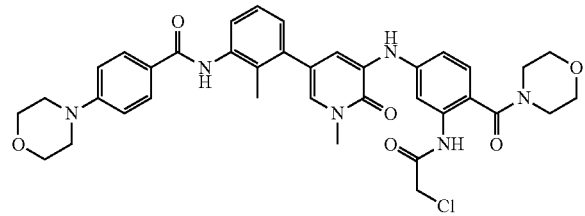 [SMILES: Cc1c(NC(=O)c2ccc(N3CCOCC3)cc2)cccc1-c1cc(Nc2ccc(C(=O)N3CCOCC3)c(NC(=O)CCl)c2)c(=O)n(C)c1]

Synthesis of Compound 1 was accomplished using a procedure similar to that described in Example 1. Exact Mass (calculated): 698.2620; MS(ESI) m/e (M+1)+: 699.2701.

Example 17

Synthesis of Compound 17 N-(3-(5-((3-propanamide-4-(morpholin-4-carbonyl)phenyl)amino)-1-methyl-6-oxo-1,6-dihydropyridin-3-yl)-2-methylphenyl)-4-morpholinbenzoylamide

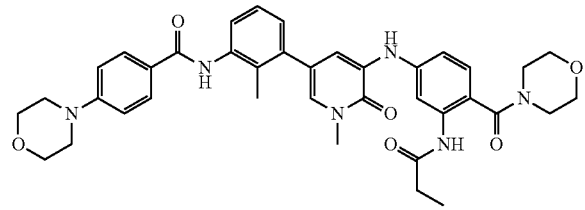 [SMILES: CCC(=O)Nc1cc(Nc2cc(-c3cccc(NC(=O)c4ccc(N5CCOCC5)cc4)c3C)cn(C)c2=O)ccc1C(=O)N1CCOCC1]

Synthesis of Compound 17 was accomplished using a procedure similar to that described in Example 1. Exact Mass (calculated): 678.3166; MS(ESI) m/e (M+1)+: 679.3144.

Example 18

Synthesis of Compound 18 N-(3-(5-((3-acrylamide-4-(morpholin-4-carbonyl)phenyl)amino)-1-methyl-6-oxo-1,6-dihydropyridin-3-yl)-2-methylphenyl)-benzo[d][1,3]dioxolanyl-5-carboxamide

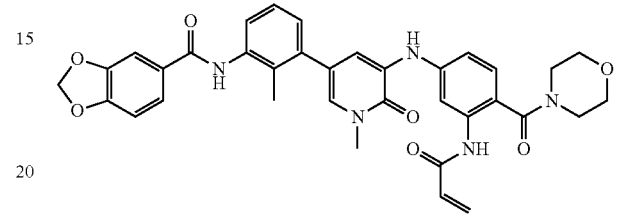

Synthesis of Compound 18 was accomplished using a procedure similar to that described in Example 1. Exact Mass (calculated): 635.2380; MS(ESI) m/e (M+1)+: 636.2351.

Example 19

Synthesis of Compound 19 N-(3-(5-((3-chloroacetamide-4-(morpholin-4-carbonyl)phenyl)amino)-1-methyl-6-oxo-1,6-dihydropyridin-3-yl)-2-methylphenyl)-benzo[d][1,3]dioxolanyl-5-carboxamide

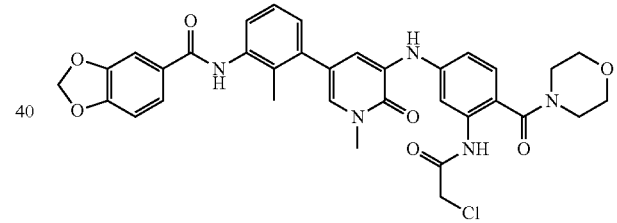

Synthesis of Compound 19 was accomplished using a procedure similar to that described in Example 1. Exact Mass (calculated): 657.1990; MS(ESI) m/e (M+1)+: 658.2001.

Example 20

Synthesis of Compound 20 N-(3-(5-((3-propanamide-4-(morpholin-4-carbonyl)phenyl)amino)-1-methyl-6-oxo-1,6-dihydropyridin-3-yl)-2-methylphenyl)-benzo[d][1,3]dioxolanyl-5-carboxamide

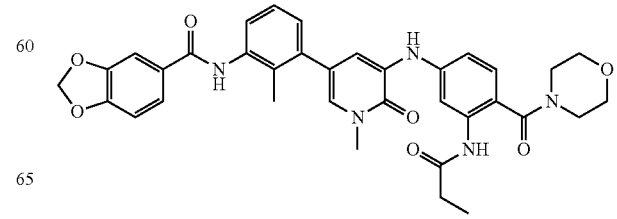

Synthesis of Compound 20 was accomplished using a procedure similar to that described in Example 1. Exact Mass (calculated): 637.2536; MS(ESI) m/e (M+1)+: 638.2601.

Example 21

Synthesis of Compound 21 N-(3-(5-((3-acrylamide-phenyl)amino)-1-methyl-6-oxo-1,6-dihydropyridin-3-yl)-2-methylphenyl)-4-(tert-butyl)benzamide

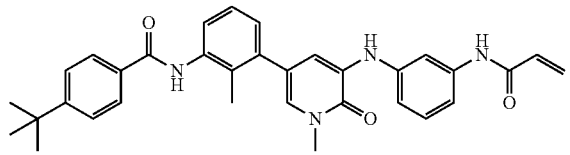 [SMILES: C=CC(=O)Nc1cccc(Nc2cc(-c3cccc(NC(=O)c4ccc(C(C)(C)C)cc4)c3C)cn(C)c2=O)c1]

Synthesis of Compound 21 was accomplished using a procedure similar to that described in Example 1. Exact Mass (calculated): 534.2631; MS(ESI) m/e (M+1)+: 535.2644.

Example 22

Synthesis of Compound 22 N-(3-(5-((3-chloroacet-amidephenyl)amino)-1-methyl-6-oxo-1,6-dihydro-pyridin-3-yl)-2-methylphenyl)-4-(tert-butyl)benz-amide

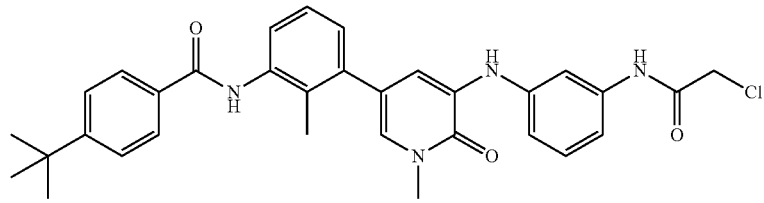 [SMILES: Cc1c(NC(=O)c2ccc(C(C)(C)C)cc2)cccc1-c1cc(Nc2cccc(NC(=O)CCl)c2)c(=O)n(C)c1]

Synthesis of Compound 22 was accomplished using a procedure similar to that described in Example 1. Exact Mass (calculated): 556.2241; MS(ESI) m/e (M+1)+: 557.2265.

Example 23

Synthesis of Compound 23 N-(3-(5-((3-propana-midephenyl)amino)-1-methyl-6-oxo-1,6-dihydro-pyridin-3-yl)-2-methylphenyl)-4-(tert-butyl)benz-amide

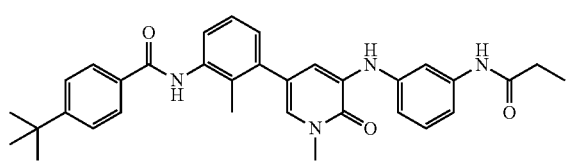 [SMILES: CCC(=O)Nc1cccc(Nc2cc(-c3cccc(NC(=O)c4ccc(C(C)(C)C)cc4)c3C)cn(C)c2=O)c1]

Synthesis of Compound 23 was accomplished using a procedure similar to that described in Example 1. Exact Mass (calculated): 536.2787; MS(ESI) m/e (M+1)+: 537.2798.

Example 24

Synthesis of Compound 24 N-(4-propanamide-2-methyl-3-(1-methyl-5-((4-(morpholin-4-carbonyl)phenyl)amino)-6-oxo-1,6-dihydropyridin-3-yl)-2-methylphenyl)-4-(tert-butyl)benzamide

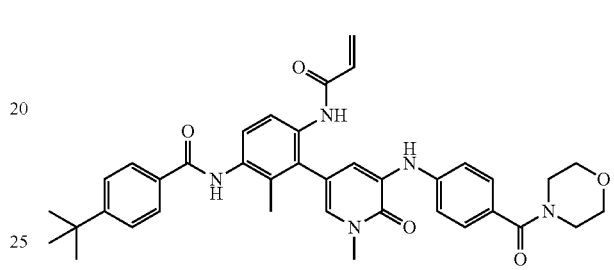

Synthesis of Compound 24 was accomplished using a procedure similar to that described in Example 1. Exact Mass (calculated): 647.3108; MS(ESI) m/e (M+1)+: 647.3091.

Example 25

Synthesis of Compound 25 N-(3-(5-((3-acrylamide-4-methylphenyl)amino)-1-methyl-6-oxo-1,6-dihy-dropyridin-3-yl)-2-methylphenyl)-4-(tert-butyl)benz-amide

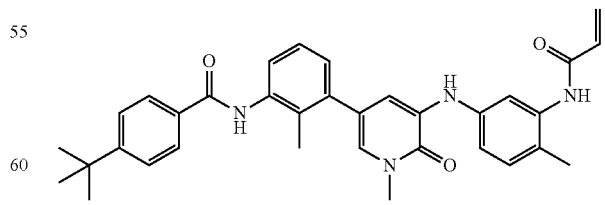

Synthesis of Compound 25 was accomplished using a procedure similar to that described in Example 1. Exact Mass (calculated): 548.2787; MS(ESI) m/e (M+1)+: 549.2795.

Example 26

Synthesis of Compound 26 N-(3-(5-((3-chloroacet-amide-4-methylphenyl)amino)-1-methyl-6-oxo-1,6-dihydropyridin-3-yl)-2-methylphenyl)-4-(tert-butyl)benzamide

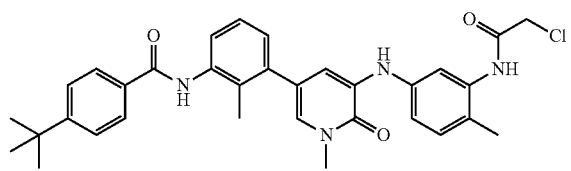 [SMILES: Cc1ccc(Nc2cc(-c3cccc(NC(=O)c4ccc(C(C)(C)C)cc4)c3C)cn(C)c2=O)cc1NC(=O)CCl]

Synthesis of Compound 26 was accomplished using a procedure similar to that described in Example 1. Exact Mass (calculated): 570.2398; MS(ESI) m/e (M+1)+: 571.2406.

Example 27

Synthesis of Compound 27 N-(3-(5-((3-propana-mide-4-methylphenyl)amino)-1-methyl-6-oxo-1,6-dihydropyridin-3-yl)-2-methylphenyl)-4-(tert-butyl)benzamide

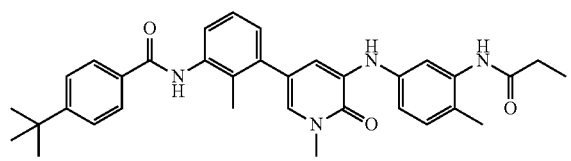 [SMILES: CCC(=O)Nc1cc(Nc2cc(-c3cccc(NC(=O)c4ccc(C(C)(C)C)cc4)c3C)cn(C)c2=O)ccc1C]

Synthesis of Compound 27 was accomplished using a procedure similar to that described in Example 1. Exact Mass (calculated): 550.2944; MS(ESI) m/e (M+1)+: 551.2964.

Example 28

Synthesis of Compound 28 2-acrylamide-4-((5-(3-(4-(tert-butyl)benzamide)-2-methylphenyl)-1-methyl-2-oxo-1,2-dihydropyridin-3-yl)amino)-N,N-dimethylbenzoylamide

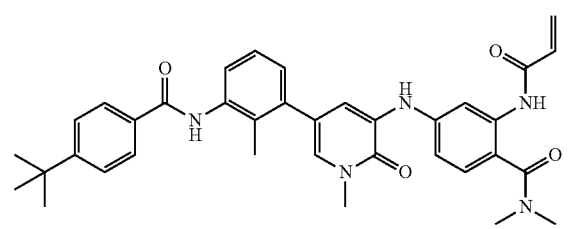 [SMILES: C=CC(=O)Nc1cc(Nc2cc(-c3cccc(NC(=O)c4ccc(C(C)(C)C)cc4)c3C)cn(C)c2=O)ccc1C(=O)N(C)C]

Synthesis of Compound 28 was accomplished using a procedure similar to that described in Example 1. Exact Mass (calculated): 605.3002; MS(ESI) m/e (M+1)+: 606.3001.

Example 29

Synthesis of Compound 29 2-chloroacetamide-4-((5-(3-(4-(tert-butyl)benzamide)-2-methylphenyl)-1-methyl-2-oxo-1,2-dihydropyridin-3-yl)amino)-N,N-dimethylbenzoylamide

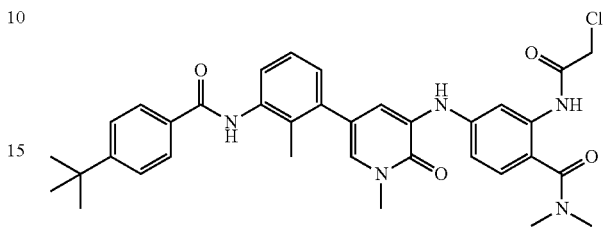

Synthesis of Compound 29 was accomplished using a procedure similar to that described in Example 1. Exact Mass (calculated): 627.2612; MS(ESI) m/e (M+1)+: 628.2645.

Example 30

Synthesis of Compound 30 2-propanamide-4-((5-(3-(4-(tert-butyl)benzamide)-2-methylphenyl)-1-methyl-2-oxo-1,2-dihydropyridin-3-yl)amino)-N,N-dimethylbenzoylamide

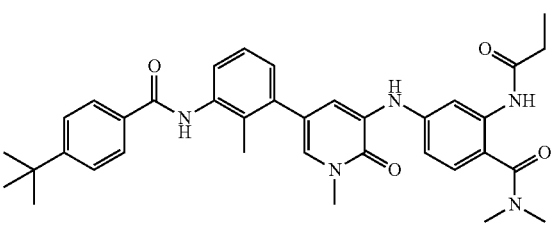 [SMILES: CCC(=O)Nc1cc(Nc2cc(-c3cccc(NC(=O)c4ccc(C(C)(C)C)cc4)c3C)cn(C)c2=O)ccc1C(=O)N(C)C]

Synthesis of Compound 30 was accomplished using a procedure similar to that described in Example 1. Exact Mass (calculated): 607.3159; MS(ESI) m/e (M+1)+: 608.3180.

Example 31

Synthesis of Compound 31 N-(3-(5-((3-acrylamide-4-(pyrrolidin-1-carbonyl)phenyl)amino)-1-methyl-6-oxo-1,6-dihydropyridin-3-yl)-2-methylphenyl)-4-(tert-butyl)benzamide

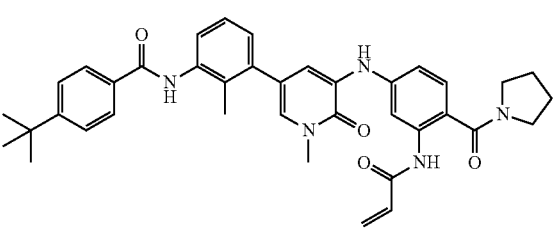 [SMILES: C=CC(=O)Nc1cc(Nc2cc(-c3cccc(NC(=O)c4ccc(C(C)(C)C)cc4)c3C)cn(C)c2=O)ccc1C(=O)N1CCCC1]

Synthesis of Compound 31 was accomplished using a procedure similar to that described in Example 1. Exact Mass (calculated): 631.3159; MS(ESI) m/e (M+1)+: 632.3178.

Example 32

Synthesis of Compound 32 N-(3-(5-((3-chloroacetamide-4-(pyrrolidin-1-carbonyl)phenyl)amino)-1-methyl-6-oxo-1,6-dihydropyridin-3-yl)-2-methylphenyl)-4-(tert-butyl)benzamide

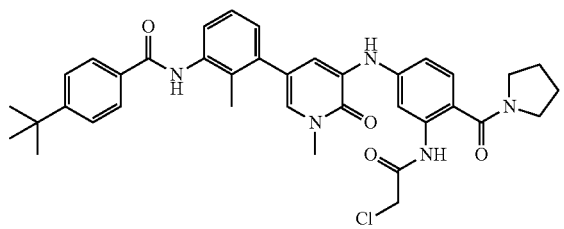 [SMILES: Cc1c(NC(=O)c2ccc(C(C)(C)C)cc2)cccc1-c1cc(Nc2ccc(C(=O)N3CCCC3)c(NC(=O)CCl)c2)c(=O)n(C)c1]

Synthesis of Compound 32 was accomplished using a procedure similar to that described in Example 1. Exact Mass (calculated):653.2769; MS(ESI) m/e (M+1)+: 654.2796.

Example 33

Synthesis of Compound 33 N-(3-(5-((3-propanamide-4-(pyrrolidin-1-carbonyl)phenyl)amino)-1-methyl-6-oxo-1,6-dihydropyridin-3-yl)-2-methylphenyl)-4-(tert-butyl)benzamide

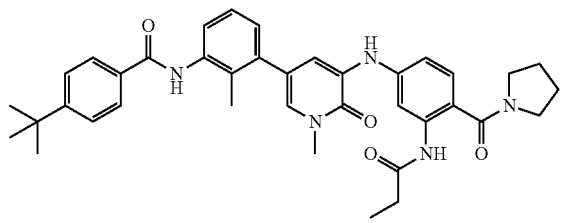 [SMILES: CCC(=O)Nc1cc(Nc2cc(-c3cccc(NC(=O)c4ccc(C(C)(C)C)cc4)c3C)cn(C)c2=O)ccc1C(=O)N1CCCC1]

Synthesis of Compound 33 was accomplished using a procedure similar to that described in Example 1. Exact Mass (calculated): 633.3315; MS(ESI) m/e (M+1)+: 634.3354.

Example 34

Synthesis of Compound 34 N-(3-(5-((3-acrylamide-4-(4-hydroxypiperidin-1-carbonyl)phenyl)amino)-1-methyl-6-oxo-1,6-dihydropyridin-3-yl)-2-methylphenyl)-4-(tert-butyl)benzamide

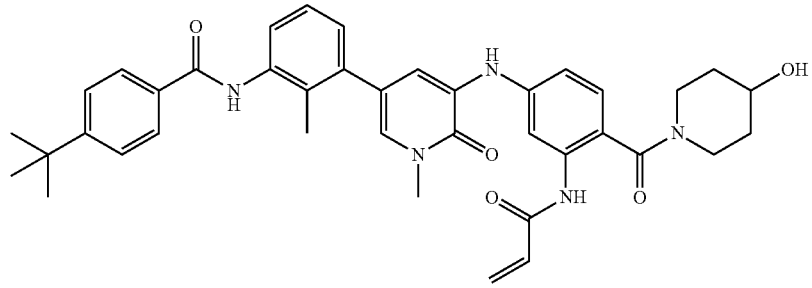 [SMILES: C=CC(=O)Nc1cc(Nc2cc(-c3cccc(NC(=O)c4ccc(C(C)(C)C)cc4)c3C)cn(C)c2=O)ccc1C(=O)N1CCC(O)CC1]

Synthesis of Compound 34 was accomplished using a procedure similar to that described in Example 1. Exact Mass (calculated): 661.3264; MS(ESI) m/e (M+1)+: 662.3272.

Example 35

Synthesis of Compound 35 N-(3-(5-((3-acrylamide-4-(morpholin-4-carbonyl)phenyl)amino)-1-methyl-6-oxo-1,6-dihydropyridin-3-yl)-2-methylphenyl)-4-(dimethylamino)benzoylamide

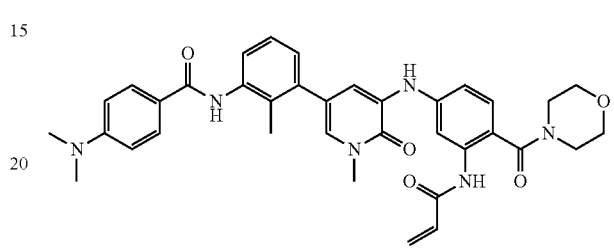

Synthesis of Compound 36 was accomplished using a procedure similar to that described in Example 1. Exact Mass (calculated): 656.2514; MS(ESI) m/e (M+1)+: 657.2541.

Example 36

Synthesis of Compound 36 N-(3-(5-((3-chloroacetamide-4-(morpholin-4-carbonyl)phenyl)amino)-1-methyl-6-oxo-1,6-dihydropyridin-3-yl)-2-methylphenyl)-4-(dimethylamino)benzoylamide

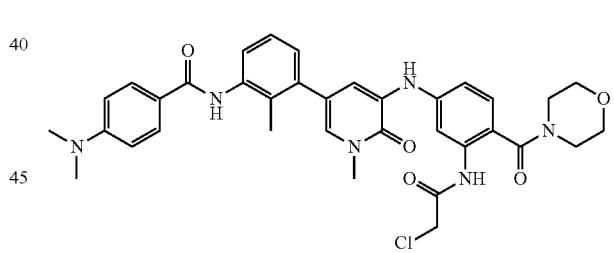

Synthesis of Compound 36 was accomplished using a procedure similar to that described in Example 1. Exact Mass (calculated): 656.2514; MS(ESI) m/e (M+1)+: 657.2523.

Example 37

Synthesis of Compound 37 N-(3-(5-((3-propanamide-4-(morpholin-4-carbonyl)phenyl)amino)-1-methyl-6-oxo-1,6-dihydropyridin-3-yl)-2-methylphenyl)-4-(dimethylamino)benzo

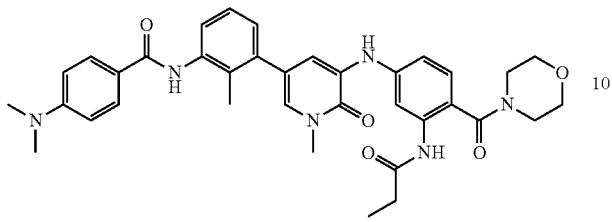

Synthesis of Compound 37 was accomplished using a procedure similar to that described in Example 1. Exact Mass (calculated): 636.3060; MS(ESI) m/e (M+1)+: 637.3094.

Example 38

Synthesis of Compound 38 tertbutyl 4-(2-acrylamide-4-((5-(3-(4-(tert-butyl)benzamide)-2-methylphenyl)-1-methyl-2-oxo-1,2-dihydropyridin-3-yl)amino)benzoyl)piperazin-1-carboxylate

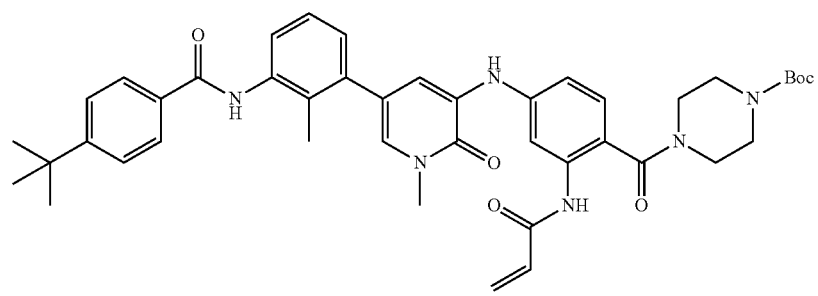 [SMILES: C=CC(=O)Nc1cc(Nc2cc(-c3cccc(NC(=O)c4ccc(C(C)(C)C)cc4)c3C)cn(C)c2=O)ccc1C(=O)N1CCN(C(=O)OC(C)(C)C)CC1]

Synthesis of Compound 38 was accomplished using a procedure similar to that described in Example 1. Exact Mass (calculated): 746.3792; MS(ESI) m/e (M+1)+: 747.3802.

Example 39

Synthesis of Compound 39 tertbutyl 4-(2-propanamide-4-((5-(3-(4-(tert-butyl)benzamide)-2-methylphenyl)-1-methyl-2-oxo-1,2-dihydropyridin-3-yl)amino)benzoyl)piperazin-1-carboxylate

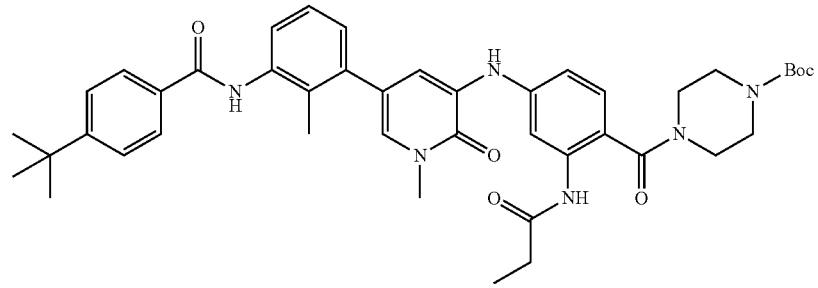 [SMILES: CCC(=O)Nc1cc(Nc2cc(-c3cccc(NC(=O)c4ccc(C(C)(C)C)cc4)c3C)cn(C)c2=O)ccc1C(=O)N1CCN(C(=O)OC(C)(C)C)CC1]

Synthesis of Compound 39 was accomplished using a procedure similar to that described in Example 1. Exact Mass (calculated): 748.3948; MS(ESI) m/e (M+1)+: 749.3985.

Example 40

Synthesis of Compound 40 N-(3-(5-((3-acrylamide-4-(piperazin-1-carbonyl)phenyl)amino)-1-methyl-6-oxo-1,6-dihydropyridin-3-yl)-2-methylphenyl)-4-(tert-butyl)benzamide

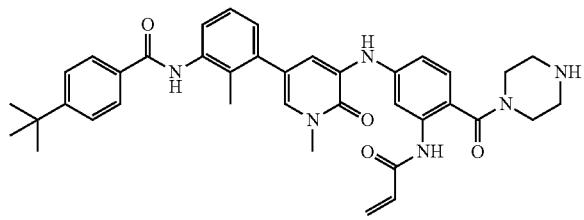 [SMILES: C=CC(=O)Nc1cc(Nc2cc(-c3cccc(NC(=O)c4ccc(C(C)(C)C)cc4)c3C)cn(C)c2=O)ccc1C(=O)N1CCNCC1]

Synthesis of Compound 40 was accomplished using a procedure similar to that described in Example 1. Exact Mass (calculated): 646.3268; MS(ESI) m/e (M+1)+: 647.3272.

Example 41

Synthesis of Compound 41 N-(3-(5-((3-propanamide-4-(piperazin-1-carbonyl)phenyl)amino)-1-methyl-6-oxo-1,6-dihydropyridin-3-yl)-2-methylphenyl)-4-(tert-butyl)benzamide

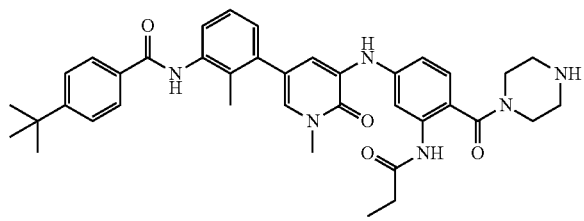 [SMILES: CCC(=O)Nc1cc(Nc2cc(-c3cccc(NC(=O)c4ccc(C(C)(C)C)cc4)c3C)cn(C)c2=O)ccc1C(=O)N1CCNCC1]

Synthesis of Compound 41 was accomplished using a procedure similar to that described in Example 1. Exact Mass (calculated): 648.3424; MS(ESI) m/e (M+1)+: 649.3444.

Example 42

Synthesis of Compound 42 N-(3-(5-((3-acrylamide-4-(morpholin-4-carbonyl)phenyl)amino)-1-methyl-6-oxo-1,6-dihydropyridin-3-yl)-2-methylphenyl)-3,4,5-trimethoxy Benzoylamide

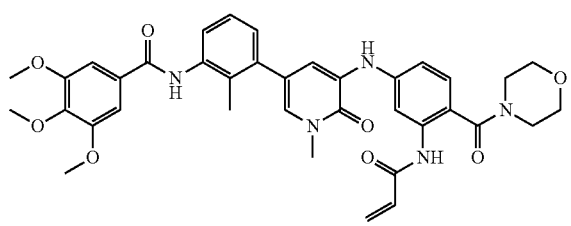 [SMILES: C=CC(=O)Nc1cc(Nc2cc(-c3cccc(NC(=O)c4cc(OC)c(OC)c(OC)c4)c3C)cn(C)c2=O)ccc1C(=O)N1CCOCC1]

Synthesis of Compound 42 was accomplished using a procedure similar to that described in Example 1. Exact Mass (calculated): 681.2799; MS(ESI) m/e (M+1)+: 682.2809.

Example 43

Synthesis of Compound 43 N-(3-(5-((3-acrylamide-4-(morpholin-4-carbonyl)phenyl)amino)-1-methyl-6-oxo-1,6-dihydropyridin-3-yl)-2-methylphenyl)-5,6,7,8-tetrahydronaphthalene-2-carboxamide

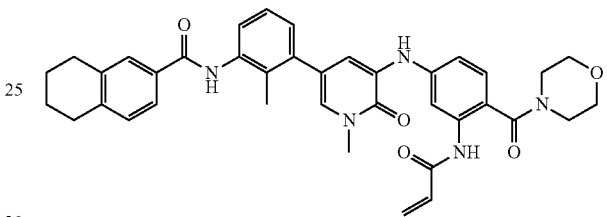

Synthesis of Compound 43 was accomplished using a procedure similar to that described in Example 1. Exact Mass (calculated): 645.2951; MS(ESI) m/e (M+1)+: 646.3001.

Example 44

Synthesis of Compound 44 N-(3-(5-((3-acrylamide-4-(morpholin-4-carbonyl)phenyl)amino)-1-methyl-6-oxo-1,6-dihydropyridin-3-yl)-2-methylphenyl)-2,3-dihydrobenzo[b][1,4]dioxin-6-carboxamide

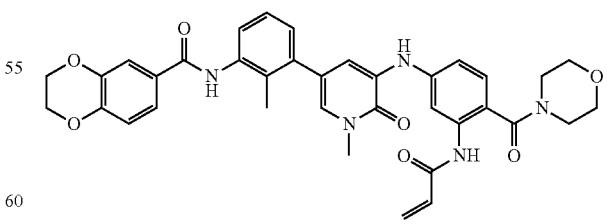

Synthesis of Compound 44 was accomplished using a procedure similar to that described in Example 1. Exact Mass (calculated): 649.2536; MS(ESI) m/e (M+1)+: 650.2564.

Example 45

Synthesis of Compound 45 N-(3-(5-((3-acrylamide-4-(morpholin-4-carbonyl)phenyl)amino)-1-methyl-6-oxo-1,6-dihydropyridin-3-yl)-2-methylphenyl)-4-(pyrrolidin-1-yl)benzoylamide

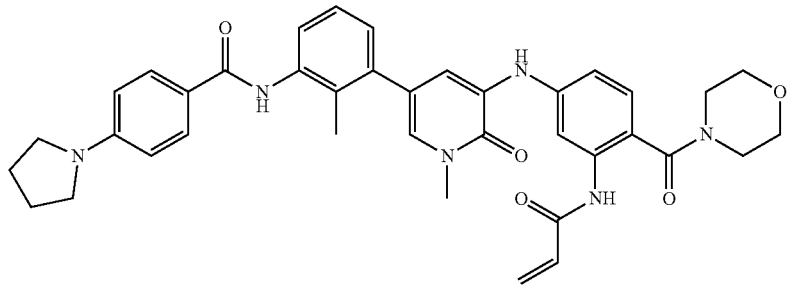 [SMILES: C=CC(=O)Nc1cc(Nc2cc(-c3cccc(NC(=O)c4ccc(N5CCCC5)cc4)c3C)cn(C)c2=O)ccc1C(=O)N1CCOCC1]

Synthesis of Compound 45 was accomplished using a procedure similar to that described in Example 1. Exact Mass (calculated): 660.3060; MS(ESI) m/e (M+1)+: 661.3091.

Example 46

Synthesis of Compound 46 2-acrylamide-4-((5-(3-(4-(tert-butyl)benzamide)-2-methylphenyl)-1-methyl-2-oxo-1,2-dihydropyridin-3-yl)amino)-N-cyclopropylbenzoylamide

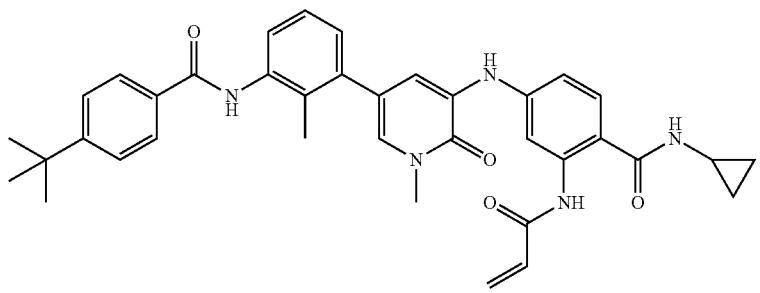 [SMILES: C=CC(=O)Nc1cc(Nc2cc(-c3cccc(NC(=O)c4ccc(C(C)(C)C)cc4)c3C)cn(C)c2=O)ccc1C(=O)NC1CC1]

Synthesis of Compound 46 was accomplished using a procedure similar to that described in Example 1. Exact Mass (calculated): 617.3002; MS(ESI) m/e (M+1)+: 618.3047.

Example 47

Synthesis of Compound 47 N-(3-(5-((3-acrylamide-4-(3-hydroxypiperidin-1-carbonyl)phenyl)amino)-1-methyl-6-oxo-1,6-dihydropyridin-3-yl)-2-methyl-phenyl)-4-(tert-butyl)benzamide

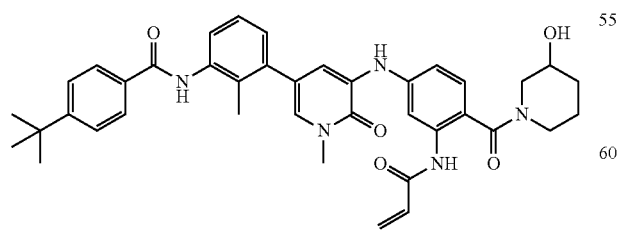

Synthesis of Compound 47 was accomplished using a procedure similar to that described in Example 1. Exact Mass (calculated): 661.3264; MS(ESI) m/e (M+1)+: 662.3299.

Example 48

Synthesis of Compound 48 N-(3-(5-((3-acrylamide-4-(4-methoxypiperidin-1-carbonyl)phenyl)amino)-1-methyl-6-oxo-1,6-dihydropyridin-3-yl)-2-methylphenyl)-4-(tert-butyl)benzamide

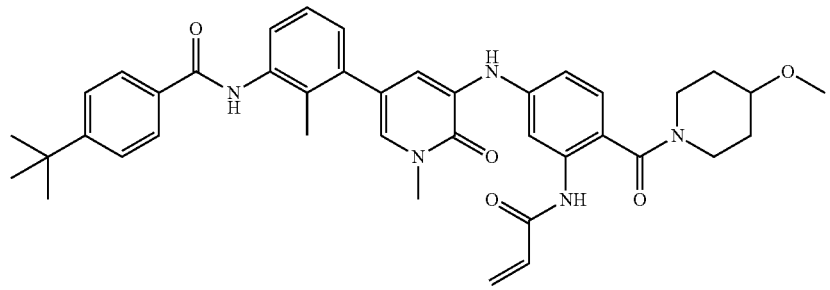 [SMILES: C=CC(=O)Nc1cc(Nc2cc(-c3cccc(NC(=O)c4ccc(C(C)(C)C)cc4)c3C)cn(C)c2=O)ccc1C(=O)N1CCC(OC)CC1]

Synthesis of Compound 48 was accomplished using a procedure similar to that described in Example 1. Exact Mass (calculated): 675.3421; MS(ESI) m/e (M+1)+: 676.3447.

Example 49

Synthesis of Compound 49 2-acrylamide-4-((5-(3-(4-(tert-butyl)benzamide)-2-methylphenyl)-1-methyl-2-oxo-1,2-dihydropyridin-3-yl)amino)methyl benzoate

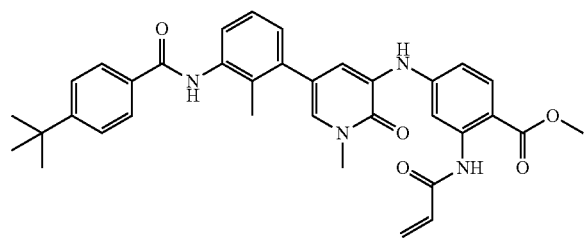 [SMILES: C=CC(=O)Nc1cc(Nc2cc(-c3cccc(NC(=O)c4ccc(C(C)(C)C)cc4)c3C)cn(C)c2=O)ccc1C(=O)OC]

Synthesis of Compound 49 was accomplished using a procedure similar to that described in Example 1. Exact Mass (calculated): 592.2686; MS(ESI) m/e (M+1)+: 593.2696.

Example 50

Synthesis of Compound 50 N-(3-(5-((3-acrylamide-4-(piperidin-1-carbonyl)phenyl)amino)-1-methyl-6-oxo-1,6-dihydropyridin-3-yl)-2-methylphenyl)-4-(dimethylamino)benzoylamide

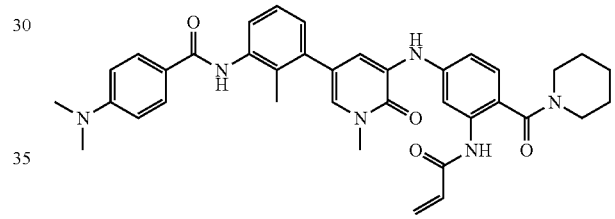

Synthesis of Compound 60 was accomplished using a procedure similar to that described in Example 1. Exact Mass (calculated): 632.3111; MS(ESI) m/e (M+1)+: 633.3150.

Example 51

Synthesis of Compound 51 2-acrylamide-4-((5-(3-(4-(dimethylamino)benzoylamide)-2-methylphenyl)-1-methyl-2-oxo-1,2-dihydropyridin-3-yl)amino)-N-(tetrahydro-2H-pyran-4-yl)benzoylamide

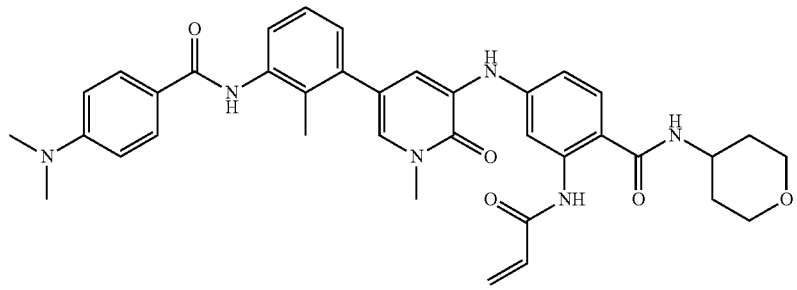 [SMILES: C=CC(=O)Nc1cc(Nc2cc(-c3cccc(NC(=O)c4ccc(N(C)C)cc4)c3C)cn(C)c2=O)ccc1C(=O)NC1CCOCC1]

Synthesis of Compound 51 was accomplished using a procedure similar to that described in Example 1. Exact Mass (calculated): 648.3060; MS(ESI) m/e (M+1)+: 649.3078.

Example 52

Synthesis of Compound 52 N-(3-(5-((3-acrylamide-4-(4-methoxypiperidin-1-carbonyl)phenyl)amino)-1-methyl-6-oxo-1,6-dihydropyridin-3-yl)-2-methyl-phenyl)-4-(dimethylamino)benzoylamide

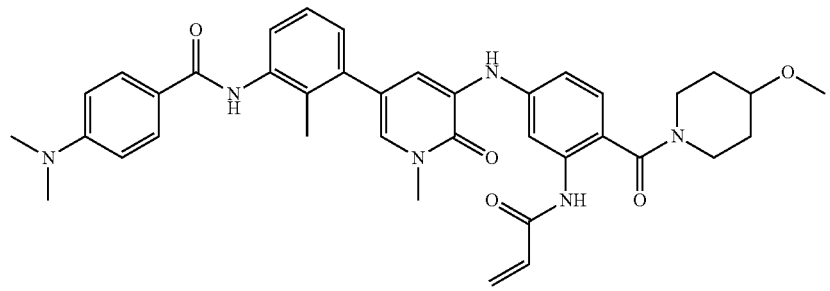

Synthesis of Compound 52 was accomplished using a procedure similar to that described in Example 1. Exact Mass (calculated): 662.3217; MS(ESI) m/e (M+1)+: 663.3243.

Example 53

Synthesis of Compound 63 2-acrylamide-4-((5-(3-(4-(dimethylamino)benzoylamide)-2-methylphenyl)-1-methyl-2-oxo-1,2-dihydropyridin-3-yl)amino)-N-(2-methoxyethyl)benzoylamide

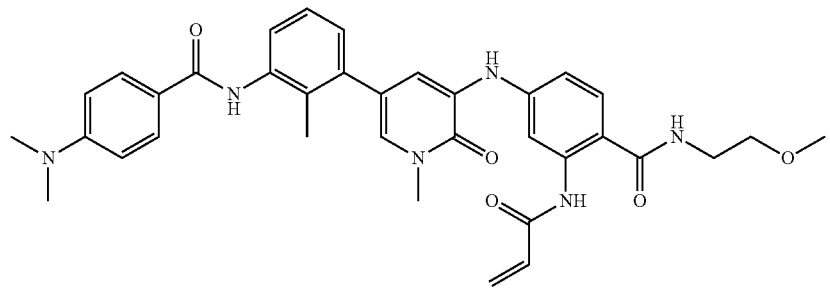

Synthesis of Compound 53 was accomplished using a procedure similar to that described in Example 1. Exact Mass (calculated): 622.2904; MS(ESI) m/e (M+1)+: 623.2941.

Example 54

Synthesis of Compound 54 2-acrylamide-4-((5-(3-(4-(dimethylamino)benzoylamide)-2-methylphenyl)-1-methyl-2-oxo-1,2-dihydropyridin-3-yl)amino)-N,N-bis(2-ethoxylethyl)benzoylamide

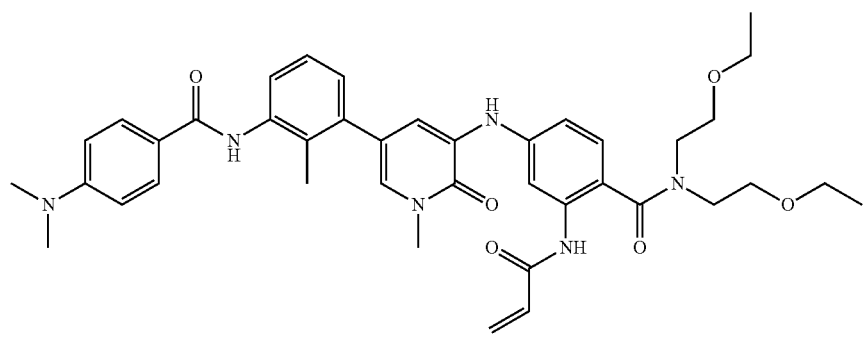 [SMILES: C=CC(=O)Nc1cc(Nc2cc(-c3cccc(NC(=O)c4ccc(N(C)C)cc4)c3C)cn(C)c2=O)ccc1C(=O)N(CCOCC)CCOCC]

Synthesis of Compound 54 was accomplished using a procedure similar to that described in Example 1. Exact Mass (calculated): 708.3635; MS(ESI) m/e (M+1)+: 709.3653.

Example 55

Synthesis of Compound 66 N-(3-(5-((3-acrylamide-4-(3-hydroxypiperdin-1-carbonyl)phenyl)amino)-1-methyl-6-oxo-1,6-dihydropyridin-3-yl)-2-methyl-phenyl)-4-(dimethylamino)benzoylamide

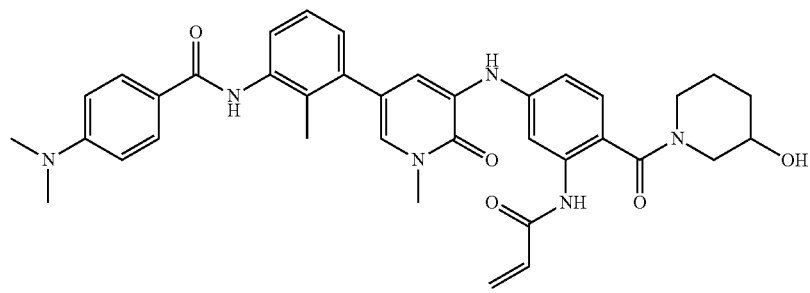 [SMILES: C=CC(=O)Nc1cc(Nc2cc(-c3cccc(NC(=O)c4ccc(N(C)C)cc4)c3C)cn(C)c2=O)ccc1C(=O)N1CCCC(O)C1]

Synthesis of Compound 55 was accomplished using a procedure similar to that described in Example 1. Exact Mass (calculated): 648.3060; MS(ESI) m/e (M+1)+: 649.3094.

Example 56

Synthesis of Compound 56 N-(3-(5-((3-acrylamide-4-(4-hydroxypiperdin-1-carbonyl)phenyl)amino)-1-methyl-6-oxo-1,6-dihydropyridin-3-yl)-2-methyl-phenyl)-4-(dimethylamino)benzoylamide

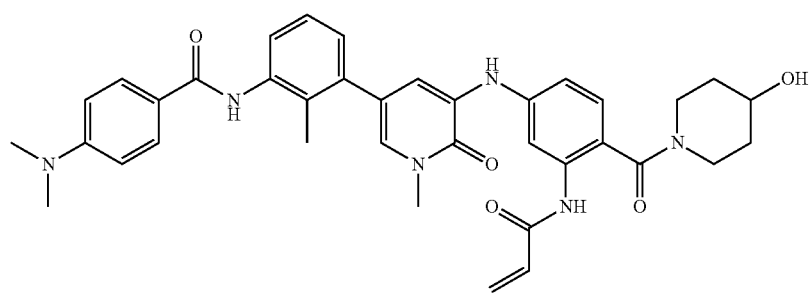 [SMILES: C=CC(=O)Nc1cc(Nc2cc(-c3cccc(NC(=O)c4ccc(N(C)C)cc4)c3C)cn(C)c2=O)ccc1C(=O)N1CCC(O)CC1]

Synthesis of Compound 66 was accomplished using a procedure similar to that described in Example 1. Exact Mass (calculated): 648.3060; MS(ESI) m/e (M+1)+: 649.3094.

Example 57

Synthesis of Compound 67 N-(3-(5-((3-acrylamide-4-(morpholin-4-carbonyl)phenyl)amino)-1-methyl-6-oxo-1,6-dihydropyridin-3-yl)-2-methylphenyl)-3-(trifluoromethyl)benzoylamide

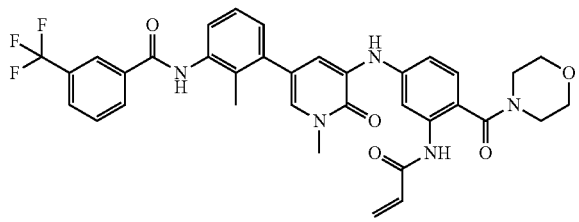 [SMILES: C=CC(=O)Nc1cc(Nc2cc(-c3cccc(NC(=O)c4cccc(C(F)(F)F)c4)c3C)cn(C)c2=O)ccc1C(=O)N1CCOCC1]

Synthesis of Compound 57 was accomplished using a procedure similar to that described in Example 1. Exact Mass (calculated): 659.2356; MS(ESI) m/e (M+1)+: 660.2378.

Example 58

Synthesis of Compound 58 N-(3-(5-((3-acrylamide-4-(morpholin-4-carbonyl)phenyl)amino)-1-methyl-6-oxo-1,6-dihydropyridin-3-yl)-2-methylphenyl)-4-methoxy Benzoylamide

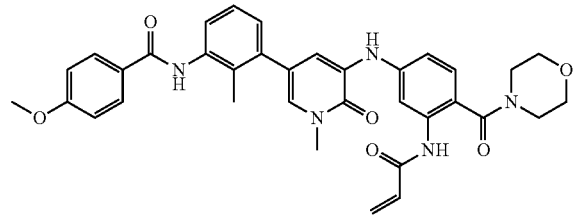 [SMILES: C=CC(=O)Nc1cc(Nc2cc(-c3cccc(NC(=O)c4ccc(OC)cc4)c3C)cn(C)c2=O)ccc1C(=O)N1CCOCC1]

Synthesis of Compound 58 was accomplished using a procedure similar to that described in Example 1. Exact Mass (calculated): 621.2587; MS(ESI) m/e (M+1)+: 622.2603.

Example 59

Synthesis of Compound 59 N-(3-(5-((3-acrylamide-4-(morpholin-4-carbonyl)phenyl)amino)-1-methyl-6-oxo-1,6-dihydropyridin-3-yl)-2-methylphenyl)-3-methoxy Benzoylamide

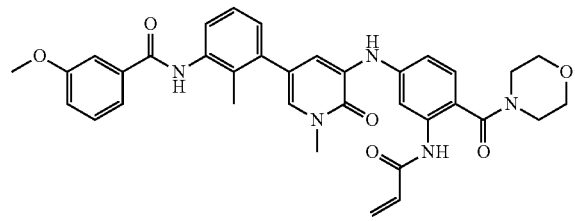 [SMILES: C=CC(=O)Nc1cc(Nc2cc(-c3cccc(NC(=O)c4cccc(OC)c4)c3C)cn(C)c2=O)ccc1C(=O)N1CCOCC1]

Synthesis of Compound 59 was accomplished using a procedure similar to that described in Example 1. Exact Mass (calculated): 621.2587; MS(ESI) m/e (M+1)+: 622.2603.

Example 60

Synthesis of Compound 60 N-(3-(5-((3-acrylamide-4-(morpholin-4-carbonyl)phenyl)amino)-1-methyl-6-oxo-1,6-dihydropyridin-3-yl)-2-methylphenyl)-4-(trifluoromethyl)benzoylamide

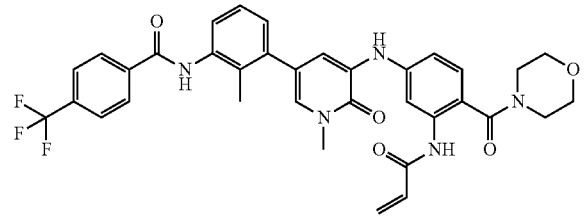

Synthesis of Compound 60 was accomplished using a procedure similar to that described in Example 1. Exact Mass (calculated): 659.2356; MS(ESI) m/e (M+1)+: 660.2377.

Example 61

Synthesis of Compound 61 N-(3-(5-((3-acrylamide-4-(morpholin-4-carbonyl)phenyl)amino)-1-methyl-6-oxo-1,6-dihydropyridin-3-yl)-2-methylphenyl)-3,4-dimethoxy Benzoylamide

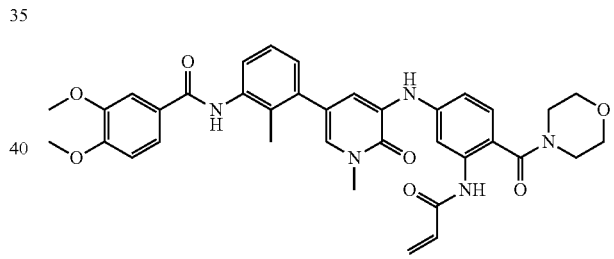

Synthesis of Compound 61 was accomplished using a procedure similar to that described in Example 1. Exact Mass (calculated): 651.2693; MS(ESI) m/e (M+1)+: 652.2724.

Example 62

Synthesis of Compound 62 N-(3-(5-((3-acrylamide-4-(morpholin-4-carbonyl)phenyl)amino)-1-methyl-6-oxo-1,6-dihydropyridin-3-yl)-2-methylphenyl)-4-ethylbenzoylamide

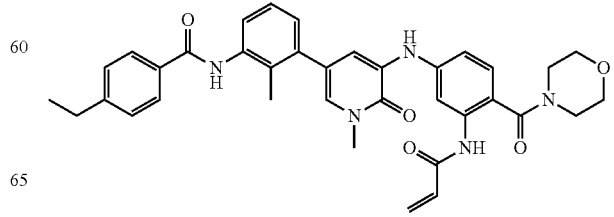

Synthesis of Compound 62 was accomplished using a procedure similar to that described in Example 1. Exact Mass (calculated): 619.2795; MS(ESI) m/e (M+1)+: 620.2817.

Example 63

Synthesis of Compound 63 N-(3-(5-((3-acrylamide-4-(morpholin-4-carbonyl)phenyl)amino)-1-methyl-6-oxo-1,6-dihydropyridin-3-yl)-2-methylphenyl)-4-methyl-3-(trifluoromethyl)benzoylamide

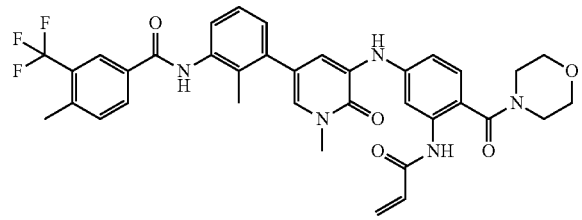 [SMILES: C=CC(=O)Nc1cc(Nc2cc(-c3cccc(NC(=O)c4ccc(C)c(C(F)(F)F)c4)c3C)cn(C)c2=O)ccc1C(=O)N1CCOCC1]

Synthesis of Compound 63 was accomplished using a procedure similar to that described in Example 1. Exact Mass (calculated): 673.2512; MS(ESI) m/e (M+1)+: 674.2534.

Example 64

Synthesis of Compound 64 N-(3-(5-((3-acrylamide-4-(morpholin-4-carbonyl)phenyl)amino)-1-methyl-6-oxo-1,6-dihydropyridin-3-yl)-2-methylphenyl)-4-isopropylbenzoylamide

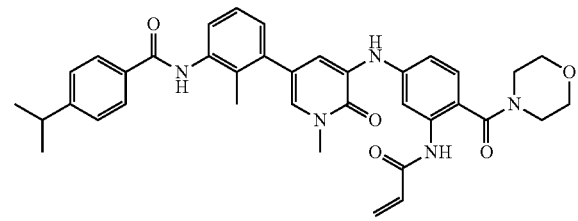

Synthesis of Compound 64 was accomplished using a procedure similar to that described in Example 1. Exact Mass (calculated): 633.2951; MS(ESI) m/e (M+1)+: 634.2957.

Example 65

Synthesis of Compound 65 N-(3-(5-((3-acrylamide-4-(morpholin-4-carbonyl)phenyl)amino)-1-methyl-6-oxo-1,6-dihydropyridin-3-yl)-2-methylphenyl)-4,5,6,7-tetrahydrobenzo[b]thiophene-2-carboxamide

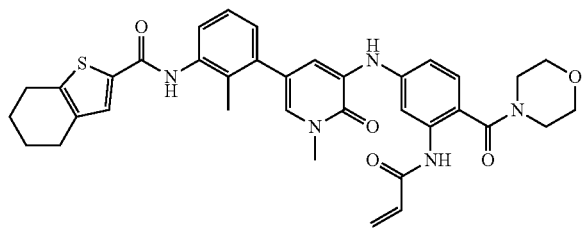 [SMILES: C=CC(=O)Nc1cc(Nc2cc(-c3cccc(NC(=O)c4cc5c(s4)CCCC5)c3C)cn(C)c2=O)ccc1C(=O)N1CCOCC1]

Synthesis of Compound 65 was accomplished using a procedure similar to that described in Example 1, except that 4,5,6,7-tetrahydrobenzo[b]thiophene-2-carboxylic acid was used as the starting material to replace Compound f. Exact Mass (calculated): 651.2515; MS(ESI) m/e (M+1)+: 652.2517.

Example 66

Synthesis of Compound 66 N-(3-(5-((3-acrylamide-4-(morpholin-4-carbonyl)phenyl)amino)-1-methyl-6-oxo-1,6-dihydropyridin-3-yl)-2-methylphenyl)-4-cyclopropylbenzoylamide

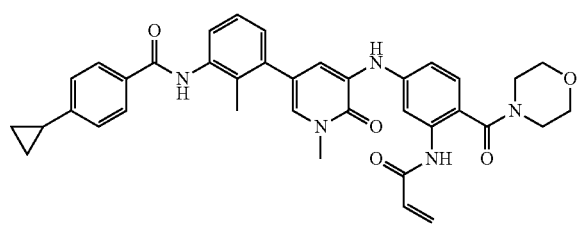 [SMILES: C=CC(=O)Nc1cc(Nc2cc(-c3cccc(NC(=O)c4ccc(C5CC5)cc4)c3C)cn(C)c2=O)ccc1C(=O)N1CCOCC1]

Synthesis of Compound 66 was accomplished using a procedure similar to that described in Example 1. Exact Mass (calculated): 631.2795; MS(ESI) m/e (M+1)+: 632.2797.

Example 67

Synthesis of Compound 67 N-(3-(5-((3-propanamide-4-(morpholin-4-carbonyl)phenyl)amino)-1-methyl-6-oxo-1,6-dihydropyridin-3-yl)-2-methylphenyl)-4,5,6,7-tetrahydrobenzo[b]thiophene-2-carboxamide

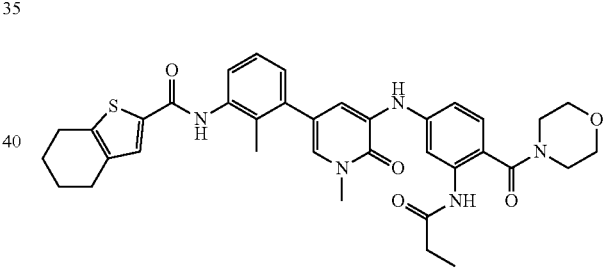

Synthesis of Compound 67 was accomplished using a procedure similar to that described in Example 65. Exact Mass (calculated): 653.2672; MS(ESI) m/e (M+1)+: 654.2673.

Example 68

Synthesis of Compound 68 N-(3-(5-((3-acrylamide-4-(morpholin-4-carbonyl)phenyl)amino)-1-methyl-6-oxo-1,6-dihydropyridin-3-yl)-2-methylphenyl)benzo[b]thiophene-2-carboxamide

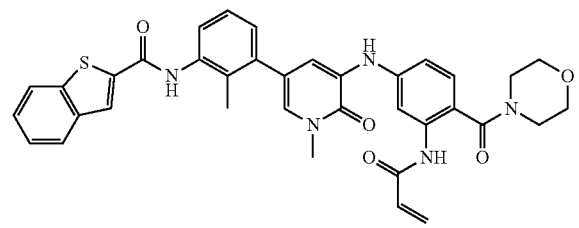 [SMILES: C=CC(=O)Nc1cc(Nc2cc(-c3cccc(NC(=O)c4cc5ccccc5s4)c3C)cn(C)c2=O)ccc1C(=O)N1CCOCC1]

Synthesis of Compound 68 was accomplished using a procedure similar to that described in Example 1, except that benzo[b]thiophene-2-carbonyl chloride was used as the starting material to replace Compound f. Exact Mass (calculated): 647.2202; MS(ESI) m/e (M+1)+:648.2234.

Example 69

Synthesis of Compound 69 N-(3-(5-((3-acrylamide-4-(pyrrolidin-1-carbonyl)phenyl)amino)-1-methyl-6-oxo-1,6-dihydropyridin-3-yl)-2-methylphenyl)-4,5,6,7-tetrahydrobenzo[b]thiophene-2-carboxamide

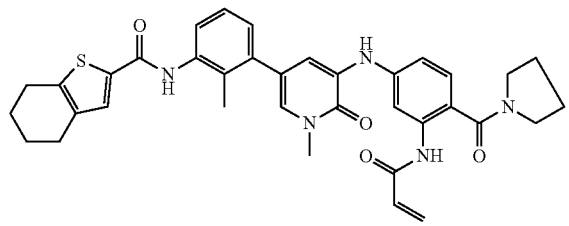 [SMILES: C=CC(=O)Nc1cc(Nc2cc(-c3cccc(NC(=O)c4cc5c(s4)CCCC5)c3C)cn(C)c2=O)ccc1C(=O)N1CCCC1]

Synthesis of Compound 69 was accomplished using a procedure similar to that described in Example 65. Exact Mass (calculated): 635.2566; MS(ESI) m/e (M+1)+: 636.2534

Example 70

Synthesis of Compound 70 N-(3-(5-((3-acrylamide-4-(morpholin-4-carbonyl)phenyl)amino)-1-methyl-6-oxo-1,6-dihydropyridin-3-yl)-2-methylphenyl)-4-methylthiophene-2-carboxamide

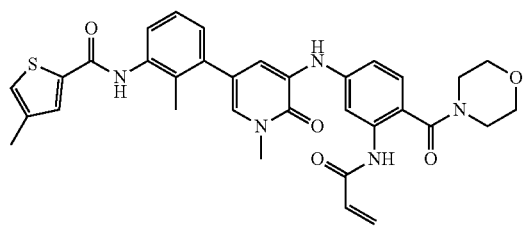 [SMILES: C=CC(=O)Nc1cc(Nc2cc(-c3cccc(NC(=O)c4cc(C)cs4)c3C)cn(C)c2=O)ccc1C(=O)N1CCOCC1]

Synthesis of Compound 70 was accomplished using a procedure similar to that described in Example 1, except that 4-methylthiophene-2-carbonyl chloride was used as the starting material to replace Compound f. Exact Mass (calculated): 611.2202; MS(ESI) m/e (M+1)+:612.2218

Example 71

Synthesis of Compound 71 N-(3-(5-((3-acrylamide-4-(morpholin-4-carbonyl)phenyl)amino)-1-methyl-6-oxo-1,6-dihydropyridin-3-yl)-2-methylphenyl)-5-methylthiophene-2-carboxamide

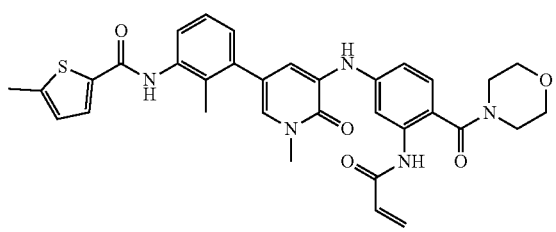 [SMILES: C=CC(=O)Nc1cc(Nc2cc(-c3cccc(NC(=O)c4ccc(C)s4)c3C)cn(C)c2=O)ccc1C(=O)N1CCOCC1]

Synthesis of Compound 71 was accomplished using a procedure similar to that described in Example 1, except that 5-methylthiophene-2-carbonyl chloride was used as the starting material to replace Compound f. Exact Mass (calculated): 611.2202; MS(ESI) m/e (M+1)+:612.2223

Example 72

Synthesis of Compound 72 N-(3-(5-((3-acrylamide-4-(4-methylpiperazin-1-yl)phenyl)amino)-1-methyl-6-oxo-1,6-dihydropyridin-3-yl)-2-methylphenyl)-4-cyclopropylbenzoylamide

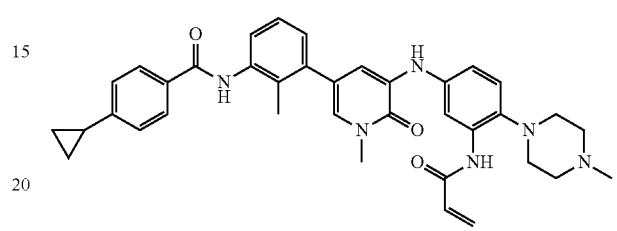

Synthesis of Compound 72 was accomplished using a procedure similar to that described in Example 1. Exact Mass (calculated): 616.3162; MS(ESI) m/e (M+1)+: 617.3187

Example 73

Synthesis of Compound 73 N-(3-(5-((3-acrylamide-4-morpholinophenyl)amino)-1-methyl-6-oxo-1,6-dihydropyridin-3-yl)-2-methylphenyl)-4-dimethylamino)benzoylamide

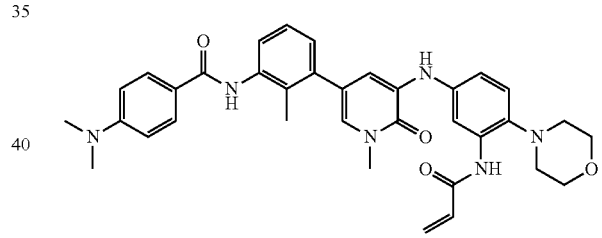

Synthesis of Compound 73 was accomplished using a procedure similar to that described in Example 1. Exact Mass (calculated): 606.2955; MS(ESI) m/e (M+1)+: 607.2967

Example 74

Synthesis of Compound 74 N-(3-(5-((3-acrylamide-4-(4-ethylpiperazin-1-yl)phenyl)amino)-1-methyl-6-oxo-1,6-dihydropyridin-3-yl)-2-methylphenyl)-4-(dimethylamino)benzoylamide

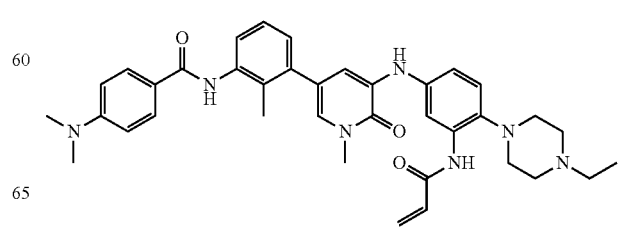

Synthesis of Compound 74 was accomplished using a procedure similar to that described in Example 1. Exact Mass (calculated): 633.3427; MS(ESI) m/e (M+1)+: 634.3467

Example 75

Synthesis of Compound 76 N-(3-(5-((3-acrylamide-4-(4-methylpiperazin-1-yl)phenyl)amino)-1-methyl-6-oxo-1,6-dihydropyridin-3-yl)-2-methylphenyl)-4,5,6,7-tetrahydrobenzo[b]thiophene-2-carboxamide

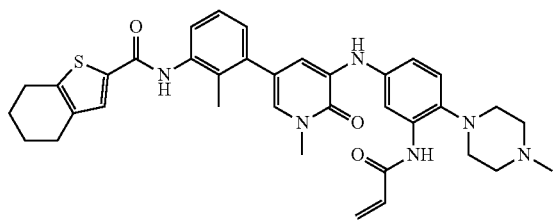 [SMILES: C=CC(=O)Nc1cc(Nc2cc(-c3cccc(NC(=O)c4cc5c(s4)CCCC5)c3C)cn(C)c2=O)ccc1N1CCN(C)CC1]

Synthesis of Compound 75 was accomplished using a procedure similar to that described in Example 65. Exact Mass (calculated): 636.2883; MS(ESI) m/e (M+1)+: 637.2891

Example 76

Synthesis of Compound 76 N-(3-(5-((3-acrylamide-4-(4-ethylpiperazin-1-yl)phenyl)amino)-1-methyl-6-oxo-1,6-dihydropyridin-3-yl)-2-methylphenyl)-4,5,6,7-tetrahydrobenzo[b]thiophene-2-carboxamide

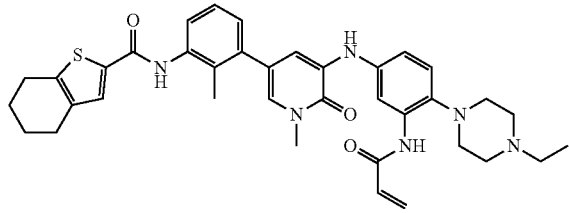 [SMILES: C=CC(=O)Nc1cc(Nc2cc(-c3cccc(NC(=O)c4cc5c(s4)CCCC5)c3C)cn(C)c2=O)ccc1N1CCN(CC)CC1]

Synthesis of Compound 76 was accomplished using a procedure similar to that described in Example 65. Exact Mass (calculated): 650.3039; MS(ESI) m/e (M+1)+: 651.3104

Example 77

Synthesis of Compound 77 N-(3-(5-((3-acrylamide-4-(dimethylamino)phenyl)amino)-1-methyl-6-oxo-1,6-dihydropyridin-3-yl)-2-methylphenyl)-4,5,6,7-tetrahydrobenzo[b]thiophene-2-carboxamide

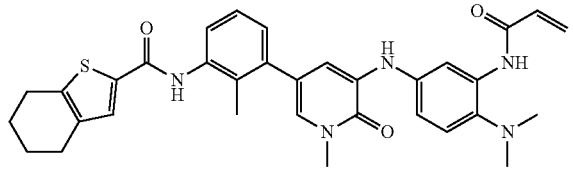 [SMILES: C=CC(=O)Nc1cc(Nc2cc(-c3cccc(NC(=O)c4cc5c(s4)CCCC5)c3C)cn(C)c2=O)ccc1N(C)C]

Synthesis of Compound 77 was accomplished using a procedure similar to that described in Example 65. Exact Mass (calculated): 581.2461; MS(ESI) m/e (M+1)+: 582.2478

Example 78

Synthesis of Compound 78 N-(3-(5-((3-acrylamide-4-morpholinophenyl)amino)-1-methyl-6-oxo-1,6-dihydropyridin-3-yl)-2-methylphenyl)4,5,6,7-tetrahydrobenzo[b]thiophene-2-carboxamide

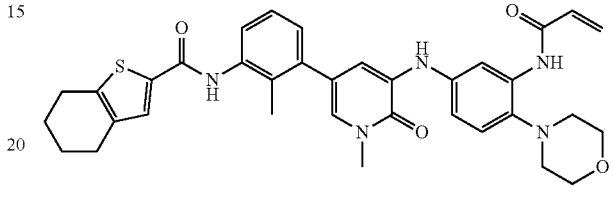

Synthesis of Compound 78 was accomplished using a procedure similar to that described in Example 65. Exact Mass (calculated): 623.2566; MS(ESI) m/e (M+1)+:624.2535

Example 79

Synthesis of Compound 79 N-(3-(5-((4-(4-acetylpiperazin-1-yl)-3-acrylamidephenyl)amino)-1-methyl-6-oxo-1,6-dihydropyridin-3-yl)-2-methylphenyl)-4,5,6,7-tetrahydrobenzo[b]thiophene-2-carboxamide

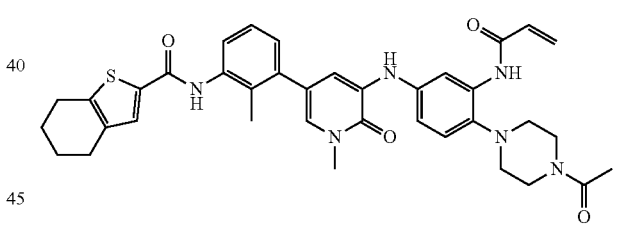

Compound 79 was accomplished using a procedure similar to that described in Example 65. Exact Mass (calculated): 664.2832; MS(ESI) m/e (M+1)+:665.2865

Example 80

Synthesis of Compound 80 N-(3-(5-((3-acrylamide-4-(pyrrolidin-1-yl)phenyl)amino)-1-methyl-6-oxo-1,6-dihydropyridin-3-yl)-2-methylphenyl)-4,5,6,7-tetrahydrobenzo[b]thiophene-2-carboxamide

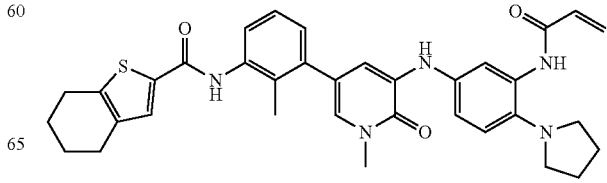

Synthesis of Compound 80 was accomplished using a procedure similar to that described in Example 65. Exact Mass (calculated): 607.2617; MS(ESI) m/e (M+1)+: 608.2637

Example 81

Synthesis of Compound 81 N-(3-(5-((3-acrylamide-4-(4-methylpiperazin-1-yl)phenyl)amino)-1-methyl-6-oxo-1,6-dihydropyridin-3-yl)-2-methylphenyl)-benzo[b]thiophene-2-carboxamide

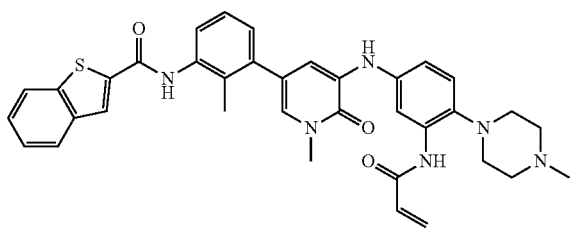 [SMILES: C=CC(=O)Nc1cc(Nc2cc(-c3cccc(NC(=O)c4cc5ccccc5s4)c3C)cn(C)c2=O)ccc1N1CCN(C)CC1]

Synthesis of Compound 81 was accomplished using a procedure similar to that described in Example 68. Exact Mass (calculated): 632.2570; MS(ESI) m/e (M+1)+: 633.2563

Example 82

Synthesis of Compound 82 N-(3-(5-((3-acrylamide-4-morpholinophenyl)amino)-1-methyl-6-oxo-1,6-dihydropyridin-3-yl)-2-methylphenyl)benzo[b]thiophene-2-carboxamide

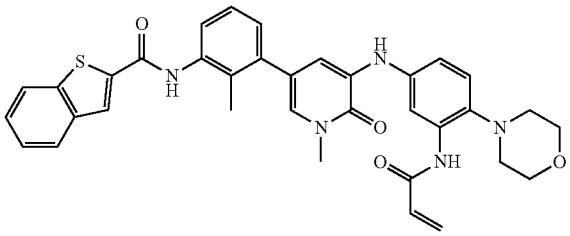 [SMILES: C=CC(=O)Nc1cc(Nc2cc(-c3cccc(NC(=O)c4cc5ccccc5s4)c3C)cn(C)c2=O)ccc1N1CCOCC1]

Synthesis of Compound 82 was accomplished using a procedure similar to that described in Example 68. Exact Mass (calculated): 619.2253; MS(ESI) m/e (M+1)+: 620.2236

Example 83

Synthesis of Compound 83 N-(3-(5-((3-acrylamide-4-(4-(dimethylamino)piperidin-1-yl)phenyl)amino)-1-methyl-6-oxo-1,6-dihydropyridin-3-yl)-2-methylphenyl)-4,5,6,7-tetrahydrobenzo[b]thiophene-2-carboxamide

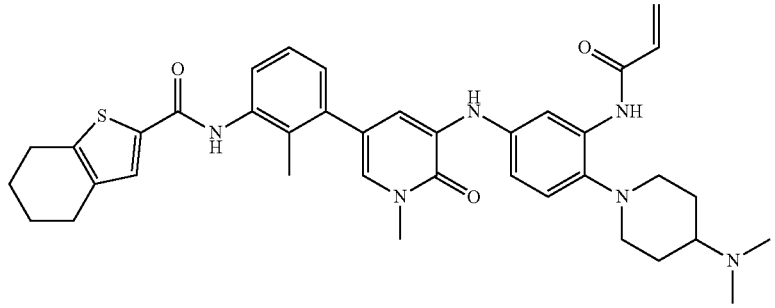 [SMILES: C=CC(=O)Nc1cc(Nc2cc(-c3cccc(NC(=O)c4cc5c(s4)CCCC5)c3C)cn(C)c2=O)ccc1N1CCC(N(C)C)CC1]

Synthesis of Compound 83 was accomplished using a procedure similar to that described in Example 65. Exact Mass (calculated): 664.3196; MS(ESI) m/e (M+1)+: 665.3203

Example 84

Synthesis of Compound 84 N-(3-(5-((3-acrylamide-4-(4-(dimethylamino)piperidin-1-yl)phenyl)amino)-1-methyl-6-oxo-1,6-dihydropyridin-3-yl)-2-methylphenyl)benzo[b]thiophene-2-carboxamide

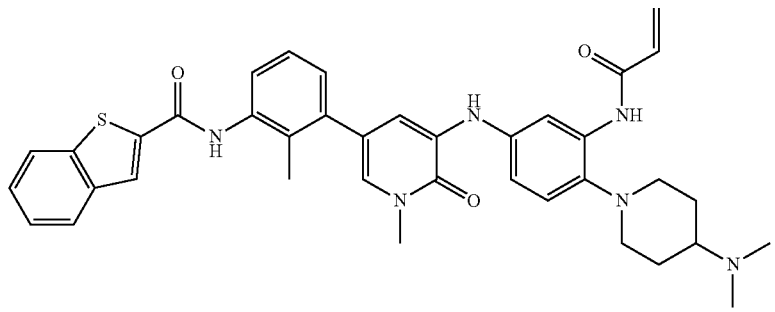 [SMILES: C=CC(=O)Nc1cc(Nc2cc(-c3cccc(NC(=O)c4cc5ccccc5s4)c3C)cn(C)c2=O)ccc1N1CCC(N(C)C)CC1]

Synthesis of Compound 84 was accomplished using a procedure similar to that described in Example 68. Exact Mass (calculated): 660.2883; MS(ESI) m/e (M+1)+: 660.2894

Example 85

Synthesis of Compound 85 N-(3-(5-((3-acrylamide-4-(1H-pyrazol-1-yl)phenyl)amino)-1-methyl-6-oxo-1,6-dihydropyridin-3-yl)-2-methylphenyl)benzo[b]thiophene-2-carboxamide

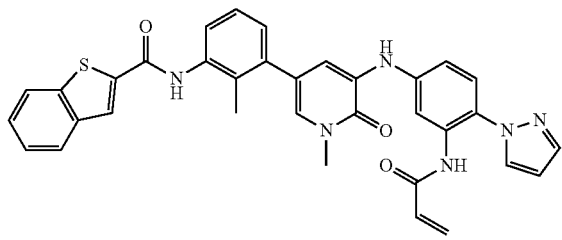 [SMILES: C=CC(=O)Nc1cc(Nc2cc(-c3cccc(NC(=O)c4cc5ccccc5s4)c3C)cn(C)c2=O)ccc1-n1cccn1]

Synthesis of Compound 85 was accomplished using a procedure similar to that described in Example 68. Exact Mass (calculated): 600.1944; MS(ESI) m/e (M+1)+: 601.2001

Example 86

Synthesis of Compound 86 N-(3-(5-((3-acrylamide-4-(1H-pyrazol-1-yl)phenyl)amino)-1-methyl-6-oxo-1,6-dihydropyridin-3-yl)-2-methylphenyl)-4,5,6,7-tetrahydrobenzo[b]thiophene-2-carboxamide

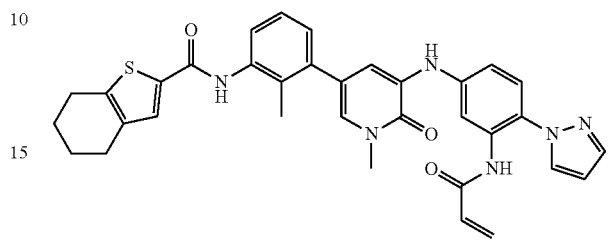

Synthesis of Compound 86 was accomplished using a procedure similar to that described in Example 65. Exact Mass (calculated): 604.2257; MS(ESI) m/e (M+1)+: 605.2273

Example 87

Synthesis of Compound 87 N-(3-(5-((3-acrylamide-4-(4-methoxypiperidin-1-yl)phenyl)amino)-1-methyl-6-oxo-1,6-dihydropyridin-3-yl)-2-methylphenyl)benzo[b]thiophene-2-carboxamide

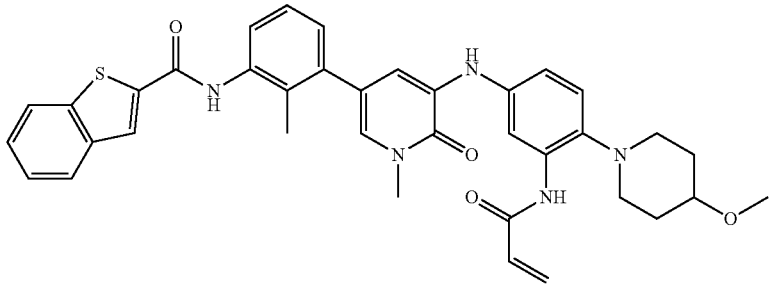 [SMILES: C=CC(=O)Nc1cc(Nc2cc(-c3cccc(NC(=O)c4cc5ccccc5s4)c3C)cn(C)c2=O)ccc1N1CCC(OC)CC1]

Synthesis of Compound 87 was accomplished using a procedure similar to that described in Example 68. Exact Mass (calculated): 647.2566; MS(ESI) m/e (M+1)+: 648.2643

Example 88

Synthesis of Compound 88 N-(3-(5-((3-acrylamide-4-(4-methoxypiperidin-1-yl)phenyl)amino)-1-methyl-6-oxo-1,6-dihydropyridin-3-yl)-2-methylphenyl)-4,5,6,7-tetrahydrobenzo[b]thiophene-2-carboxamide

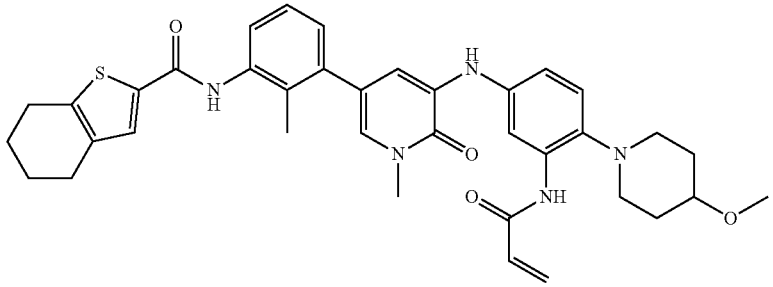 [SMILES: C=CC(=O)Nc1cc(Nc2cc(-c3cccc(NC(=O)c4cc5c(s4)CCCC5)c3C)cn(C)c2=O)ccc1N1CCC(OC)CC1]

Synthesis of Compound 88 was accomplished using a procedure similar to that described in Example 65. Exact Mass (calculated): 651.2879; MS(ESI) m/e (M+1)+: 652.2893

Example 89
Synthesis of Compound 89 N-(3-(5-((3-acrylamide-4-(4-isopropylpiperazin-1-yl)phenyl)amino)-1-methyl-6-oxo-1,6-dihydropyridin-3-yl)-2-methylphenyl)-4,5,6,7-tetrahydrobenzo[b]thiophene-2-carboxamide

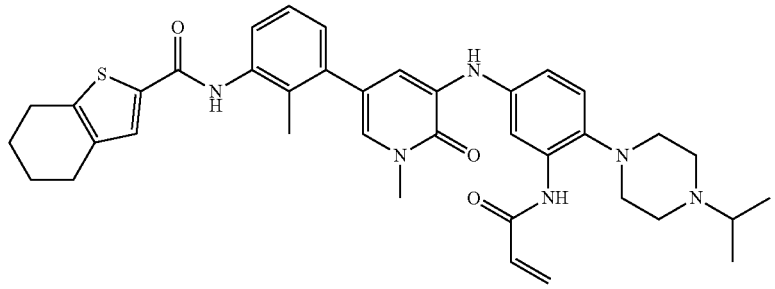 [SMILES: C=CC(=O)Nc1cc(Nc2cc(-c3cccc(NC(=O)c4cc5c(s4)CCCC5)c3C)cn(C)c2=O)ccc1N1CCN(C(C)C)CC1]

Compound 89 was accomplished using a procedure similar to that described in Example 65. Exact Mass (calculated): 664.3196; MS(ESI) m/e (M+1)+:665.3212

Example 90
Synthesis of Compound 90 N-(3-(5-((3-acrylamide-4-(4-isopropylpiperazin-1-yl)phenyl)amino)-1-methyl-6-oxo-1,6-dihydropyridin-3-yl)-2-methylphenyl)benzo[b]thiophene-2-carboxamide

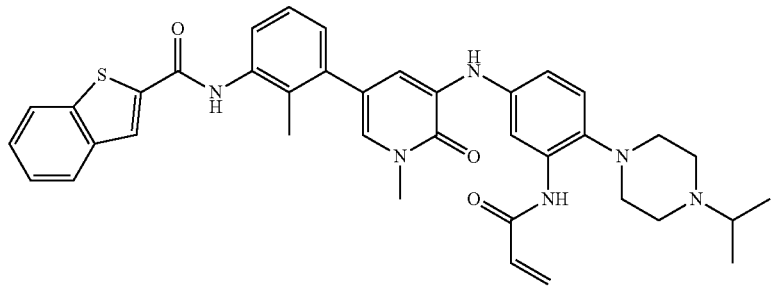 [SMILES: C=CC(=O)Nc1cc(Nc2cc(-c3cccc(NC(=O)c4cc5ccccc5s4)c3C)cn(C)c2=O)ccc1N1CCN(C(C)C)CC1]

Synthesis of Compound 90 was accomplished using a procedure similar to that described in Example 68. Exact Mass (calculated): 660.2883; MS(ESI) m/e (M+1)+: 661.2893

Example 91
Synthesis of Compound 91 N-(3-(5-((3-acrylamide-4-(4-ethylpiperazin-1-yl)phenyl)amino)-1-methyl-6-oxo-1,6-dihydropyridin-3-yl)-2-methylphenyl)benzo[b]thiophene-2-carboxamide

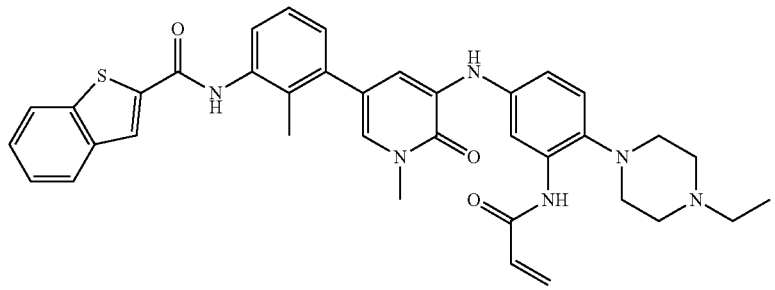 [SMILES: C=CC(=O)Nc1cc(Nc2cc(-c3cccc(NC(=O)c4cc5ccccc5s4)c3C)cn(C)c2=O)ccc1N1CCN(CC)CC1]

Synthesis of Compound 91 was accomplished using a procedure similar to that described in Example 68. Exact Mass (calculated): 646.2726; MS(ESI) m/e (M+1)+: 647.2734

Example 92

Synthesis of Compound 92 N-(3-(5-((4-(4-acetylpiperazin-1-yl)-3-acrylamidephenyl)amino)-1-methyl-6-oxo-1,6-dihydropyridin-3-yl)-2-methyl-phenyl)benzo[b]thiophene-2-carboxamide

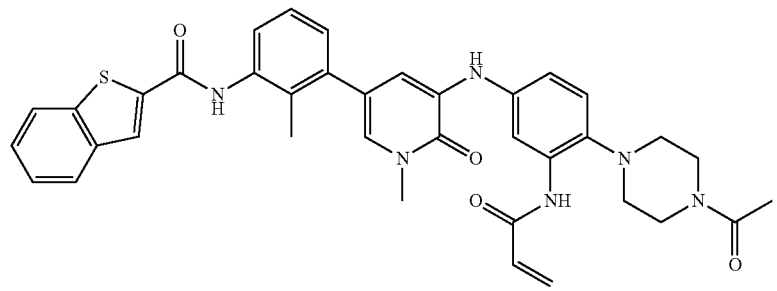 [SMILES: C=CC(=O)Nc1cc(Nc2cc(-c3cccc(NC(=O)c4cc5ccccc5s4)c3C)cn(C)c2=O)ccc1N1CCN(C(C)=O)CC1]

Synthesis of Compound 92 was accomplished using a procedure similar to that described in Example 68. Exact Mass (calculated): 660.2519; MS(ESI) m/e (M+1)+: 661.2537

Example 93

Synthesis of Compound 93 N-(3-(5-((3-acrylamide-4-(dimethylamino)phenyl)amino)-1-methyl-6-oxo-1,6-dihydropyridin-3-yl)-2-methylphenyl)benzo[b]thiophene-2-carboxamide

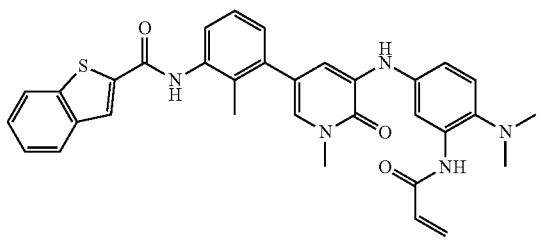 [SMILES: C=CC(=O)Nc1cc(Nc2cc(-c3cccc(NC(=O)c4cc5ccccc5s4)c3C)cn(C)c2=O)ccc1N(C)C]

Synthesis of Compound 93 was accomplished using a procedure similar to that described in Example 68. Exact Mass (calculated): 577.2148; MS(ESI) m/e (M+1)+: 578.2157

Example 94

Btk In Vitro Inhibitory Activity and Verification of Irreversibility

The Btk $IC_{50}$ of some compounds disclosed herein was determined in a cell-free kinase assay as described below.

The BTK wild-type plasmid and the BTK mutant plasmid (C481S) were respectively transfected into SF9 cells (purchased from invitrogen), and after three generations of virus amplification, the P3-generation virus was used to transfect SF9 cells which were collected after 72-hour culture to obtain protein BTK WT and protein BTK C481S, which were then purified. Various concentrations of Compound 1, 6 and 35 were respectively added into protein BTK WT and protein BTK C481S to react for 30 mins at room temperature and then 100 μM ATP was added to react for 20 min at 37° C. Results were shown in FIGS. 1a-1e, wherein "BTK" refers to BTK protein, "BTK WT" refers to wild-type BTK protein, and "BTK C481S" refers to C481S mutant BTK protein. The results shown in the figures reflected that Compound 1 and Compound 35 had strong inhibitory effects against BTK WT protein, wherein the $EC_{50}$ of Compound 1 is 4.7 nM, and the $EC_{50}$ of Compound 35 is 16 nM. In the same experiment, Compound 1 and Compound 35 showed significantly weaker inhibitory effects against BTK C481S, wherein the $EC_{50}$ of Compound 1 is 185.1 nM, and the $EC_{50}$ of Compound 35 is 186 nM. Meanwhile, Compound 6 (the only difference as compared with Compound 1 lies in that it has a single bond at the terminal of $R_2$ substituent and is a reversible inhibitor), which has a similar structure as Compound 1, showed no inhibitory effects against BTK WT and BTK C481S. It suggested that Compound 1 and Compound 35 were irreversible inhibitors of BTK.

Example 95

Effects of Btk Inhibitors on Upstream and Downstream Signaling Pathway in cells

By assaying a number of cellular biochemical and functional endpoints, the properties of the compounds were further characterized. Specifically, we evaluated the selectivity of Compound 1 and Compound 35 in inhibition of protein kinases AKT and ErK which are relatively in close relation to Btk inhibition. MEC-2 (chronic B cell leukemia cells, purchased from ATCC), Pfeiffer (human diffuse large cell lymphoma B lymphocytes, purchased from Cobioer Biosciences Co., LTD (Nanjing)), Ramos cells (human B lymphoma cells, purchased from ATCC), TMD8 cells (diffuse large B-cell lymphoma cells, purchased from ATCC), and U2932 (B-cell lymphoma cells, purchased from ATCC) were respectively treated with various concentrations of Compound 1, and MEC-1 (human B-cell chronic lymphocytic leukemia cell strain, purchased from ATCC) was treated with Compound 35 for 4 hours, followed by stimulation with anti-IgM for 10 mins, and then the samples were harvested. In this experiment, PC132765 (purchased from Shanghai Haoyuan Chemexpress Co., Ltd.), CGI11746 (purchased from Shanghai Haoyuan Chemexpress Co., Ltd.) and Compound 6 (prepared herein) were used as control (see FIGS. 2a-2f).

Effects of the compounds on phosphorylation of BTKY223, BTKY551, PLCγ₁Y783, PLCγ₂Y759, PLCγ₂Y1217, P—NF-κB P65, P-AKT Ser473, Erk Thr202/Tyr204 and the like were determined (FIGS. 2a-2f). The results showed that Compound 1 and Compound 35 could selectively and significantly inhibit phosphorylation of tyrosine Y223 on Btk (FIGS. 2a-2f).

Example 96

Effects of the Novel Kinase Inhibitors on Cell Apoptosis

Various concentrations (0.5 μM, 1 μM, 5 μM, 10 μM) of Compound 1 was administered to Pfeiffer (human diffuse large cell lymphoma B lymphocytes, purchased from Cobioer Biosciences Co., LTD (Nanjing)) and U2932 (B-cell lymphoma cells, purchased from ATCC) in order to confirm whether cell death after the administration was caused by apoptosis or necrosis. After 48 hours, effects of Compound 1 on protein cleavage of the DNA repairase poly(ADP-ribose) polymerase (PARP) and Caspase (cysteinyl aspartate-specific proteinase) 3 that were closely related to cell apoptosis was examined.

Figure 3A:
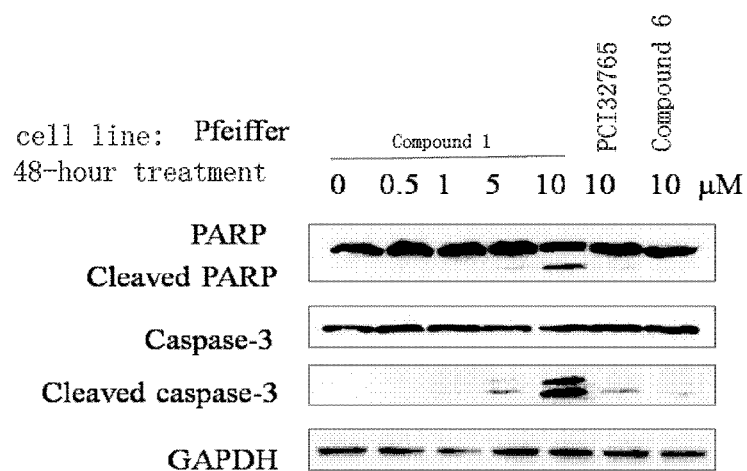
FIG. 3a illustrates the results in Pfeiffer cell line.
Figure 3B:
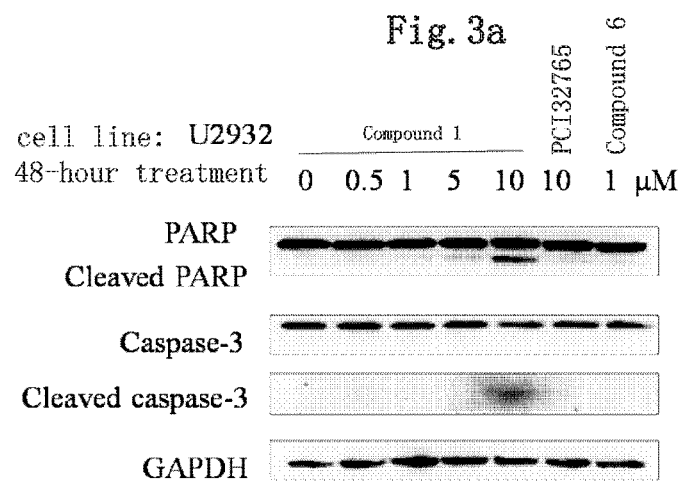
FIG. 3b illustrates the result in U2932 cell line.

Results were shown in FIGS. 3a and 3b, and it was reflected that Compound 1 could lead to cell apoptosis in Pfeiffer and U2932, and when administered at 10 μM, significant cleavage of DNA repairase poly(ADP-ribose) polymerase (PARP) was observed and cleavage of Caspase 3 that is downstream of PARP was also observed.

Example 97

Effect of the Novel Kinase Inhibitors on Cell Cycle

Effect of Compound 1 on cell cycle distribution was examined respectively in Pfeiffer (human diffuse large cell lymphoma B lymphocytes, purchased from Cobioer Biosciences Co., LTD (Nanjing)) and U2932 (B-cell lymphoma cells, purchased from ATCC) cells in order to study the growth cycle to which the cells were blocked upon compound administration. The above cells were treated with various concentrations (0.5 μM, 1 μM, 5 μM, 10 μM) of Compound 1, 10 μM of PC132765 and 10 μM of Compound 6 (FIG. 4a) or 1 μM of Compound 6 (FIG. 4b) for 48 hours, and then cells were collected and washed twice with 1×PBS buffer, and fixed with 75% ethanol at −20° C. for 24 hours, washed again with 1×PBS buffer twice, followed by addition of 0.5 mL 1×PBS buffer and 0.5 mL of PI dyeing liquor (purchased from BD Bioscience, USA), and then the cells were placed in the dark at 37° C. for dyeing 15 minutes and the cell cycle distribution was detected by flow cytometry (BD FACS Calibur). The results were shown in FIGS. 4a-4b.

Figure 4A:
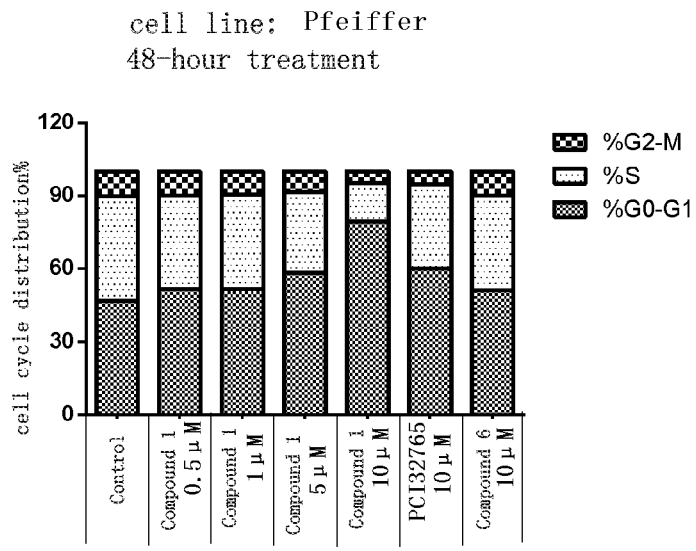
FIG. 4 illustrates the effects of compound 1 on cell cycles in two cell lines Pfeiffer (FIG. 4a) and U2932 (FIG. 4b).
Figure 4B:
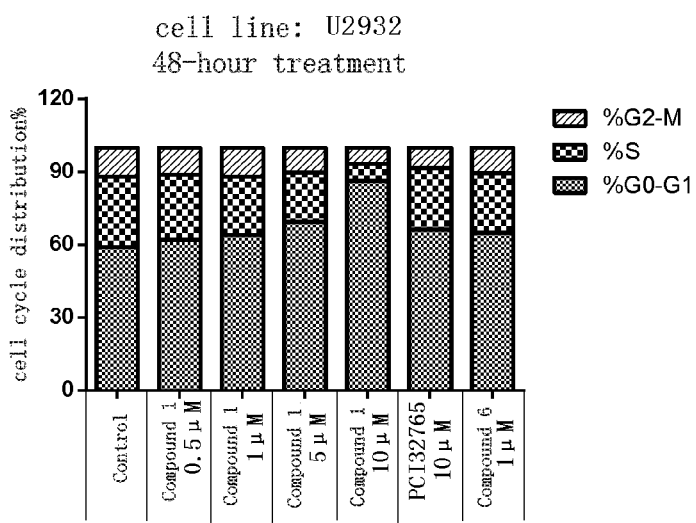

Experiments shown in FIGS. 4a-4b reflected that Compound 1 influenced the cell cycle of both two cell strains. Under 10 μM of Compound 1, there was significant cell cycle arrest in G0-G1.

Example 98

Experimental Investigation of In Vitro Enzymatic Activity of BTK Inhibitors

In vitro enzymatic activity of the compounds against BTK was determined in a experimental assay of in vitro enzymatic activity using ATP-Glo kit (purchased from Progema, USA).

9 μL of BTK protein kinase (at a concentration of 1.5 ng/μL) was used to react with compounds (1 μL) shown in the following table that were diluted three times in gradient at room temperature for 4 hours (the final concentration of the compound being 10 μM, 3 μM, 1 μM, 0.3 μM, 0.1 μM, 0.03 μM, 0.01 μM, 0.003 μM);

2 μL of ATP and 3 μL of the substrate Poly(4:1 Glu, Tyr)Peptide (Promega, USA) (the final concentrations being 10 μM and 0.2 μg/μL, respectively) were added to allow reaction at 37° C. for 1 hour;

5 μL of BTK kinase solution after reaction was taken and added into 5 μL of ADP-Glo™ (Promega, USA) reagent to allow reaction at room temperature for 40 mins so as to terminate the kinase reaction and exhaust the remaining ATP;

10 μL kinase detecting reagent was added to convert ADP to ATP, and newly synthesized ATP was detected using coupled luciferase/fluorescein reaction, then the IC50 values were calculated by using a plotting method based on the Envision reading.

The results in Table 3 reflected that Compound 1 and Compound 35 exhibited strong inhibitory effects on BTK protein and the IC$_{50}$ were 7.09 nM and 5 nM respectively. The results further showed that Compound 6 also exhibited relatively strong inhibitory effects. Combining and analyzing the results of Table 3 and the results of Example 94, it was confirmed that Compound 1 is a very strong BTK inhibitor while Compound 6 had a much weaker BTK inhibitory effects as compared with Compound 1, which suggested that Compound 1 was an irreversible BTK inhibitor while Compound 6 was a reversible inhibitor. Based on structure analysis, it was believed that this was because cysteine of BTK481 could be added to the double bond of acrylamide of Compound 1 such that the compound could bind firmly to BTK protein and accordingly inhibit the phosphorylation of BTK protein kinase to thereby block BTK signaling; in contrast, in absence of such double bond, Compound 6 bond to BTK reversibly although it could inhibit the phosphorylation of BTK.

TABLE 3

IC$_{50}$ of different Compounds against BTK obtained in in vitro assay

| Compound | Compound 1 | Compound 2 | Compound 3 | Compound 4 | Compound 6 | Compound 7 | Compound 8 | Compound 9 |
|---|---|---|---|---|---|---|---|---|
| BTK/IC50 | 7.09 nM | 37.95 nM | 144 nM | 32.62 nM | 207.4 nM | 1.22 μM | 2.61 μM | 88.92 nM |
| Compound | Compound 11 | Compound 12 | Compound 15 | Compound 16 | Compound 18 | Compound 19 | Compound 22 | Compound 24 |
| BTK/IC50 | 151.6 nM | 4.62 μM | 262 nM | 437 nM | 187 nM | 197 nM | 5.53 μM | 1.77 μM |

TABLE 3-continued

IC$_{50}$ of different Compounds against BTK obtained in in vitro assay

| Compound | Compound 25 | Compound 26 | Compound 28 | Compound 30 | Compound 31 | Compound 32 | Compound 33 | Compound 35 |
|---|---|---|---|---|---|---|---|---|
| BTK/IC50 | 212 nM | 223 nM | 25 nM | 339 nM | 19 nM | 29 nM | 165 nM | 5 nM |
| Compound | Compound 36 | Compound 37 | Compound 38 | Compound 39 | Compound 41 | Compound 43 | Compound 44 | Compound 45 |
| BTK/IC50 | 24 nM | 646 nM | 85 nM | 503 nM | 42 nM | 41 nM | 72 nM | 101 nM |
| Compound | Compound 46 | Compound 47 | Compound 43 | Compound 49 | Compound 50 | Compound 51 | Compound 52 | Compound 53 |
| BTK/IC50 | 45 nM | 24 nM | 70 nM | 162 nM | 91 nM | 89 nM | 586 nM | 667 nM |
| Compound | Compound 55 | Compound 56 | Compound 57 | Compound 59 | Compound 60 | Compound 61 | Compound 62 | Compound 63 |
| BTK/IC50 | 181 nM | 124 nM | >10000 nM | 816 nM | 104 nM | 4858 nM | 164 nM | 800 nM |
| Compound | Compound 64 | Compound 65 | Compound 66 | Compound 67 | Compound 68 | Compound 69 | Compound 70 | Compound 71 |
| BTK/IC50 | 22 nM | 25 nM | 180 nM | 25 nM | 22 nM | 83.6 nM | 114 nM | 30 nM |
| Compound | Compound 72 | Compound 73 | Compound 74 | Compound 75 | Compound 76 | Compound 77 | Compound 78 | Compound 79 |
| BTK/IC50 | 180 nM | 24.9 nM | 23 nM | 7 nM | 25 nM | 101 nM | 119 nM | 82 nM |
| Compound | Compound 80 | Compound 81 | Compound 82 | Compound 53 | Compound 84 | Compound 85 | Compound 86 | Compound 87 |
| BTK/IC50 | 83 nM | 28.9 nM | 98.8 nM | 16.7 nM | 7.8 nM | 130.1 nM | 9.9 nM | 126.1 nm |
| Compound | Compound 88 | Compound 89 | Compound 90 | Compound 91 | Compound 92 | Compound 93 | | |
| BTK/IC50 | 167.5 nM | 23.1 nM | 6.5 nM | 156 nM | 71.7 nM | 15.4 nM | | |

Example 99

Effects of Btk Inhibitors on Growth of Cancer Cells

The selectivity of Compound 1 in inhibiting the proliferation of cancer cells was further evaluated by testing the effect of Btk inhibitors on the growth of cancer cells. The following cells were adopted in the example: acute myelocytic leukemia cell strains (acute myelocytic leukemia, AML) HL-60, B-lymphoma cell Ramos, colon cancer cells HCT116, leukemic cells K562, B-cell lymphoma cells U2932, diffuse large B-cell lymphoma cell line OCI-LY10, diffuse histiocytic lymphoma cells SU-DHL-2, diffuse large B-cell lymphoma cell lines TMD8, leukemia cell OCI-AML-3, acute promyelocytic leukemia cell line NB-4 (Lu+), MDS-RAEB (myelodysplastic syndrome—excessive blasts) cell lines SKM-1, human leukocyte leukemia cells HEL, acute myeloid leukemia cell lines (acute myelocytic leukemia, AML) U937, acute myeloid leukemia cell lines (acute myelocytic leukemia, AML) MOLM14, acute myeloid leukemia cell lines (acute myelocytic leukemia, AML) MOLM13, acute myeloid leukemia cell lines (acute myelocytic leukemia, AML) M-07e, acute myeloid leukemia cell lines (acute myelocytic leukemia, AML) MV4-11, acute myeloid leukemia cell lines (acute myelocytic leukemia, AML) MOLM16, diffuse large B-cell lymphoma cell lines Pfeiffer, multiple myeloma cell lines (multiple myeloma) RPM18226, bone marrow plasma cell tumor cells AMO-1, mouse pro-B cells BaF3, all purchased from ATCC. This example further used mouse TEL-EGFR-BaF3 (stably expressing TEL-EGFR activated kinase), mouse TEL-EGFR/T790-BaF3 cells (stably expressing TEL-EGFR-C797S point mutation kinase), mouse TEL-BMX-BaF3 cells (stably expressing TEL-BMX activated kinase), mouse TEL-BLK-BaF3 cells (stably expressing TEL-BLK activated kinase), mouse TEL-JAK3-BaF3 cells (stably expressing TEL-JAK3 activated kinase), mouse TEL-LYN-BaF3 cells (stably expressing TEL-LYN activated kinase), all of which were constructed in our laboratory according to the following method: the kinase region sequences of human EGFR, EGFR/C797S, BLK, BMX, JAK3, LYN were respectively amplified via PCR, and inserted into MSCV-Puro vectors harboring N-terminal TEL fragment (Clontech). Site-Directed Mutagenesis kit (Stratagene) was used to incorporate a mutation at a corresponding position if a mutation is desired. The resultants were stably transfected into mouse BaF3 cells by retrovirus methods and growth factor IL-3 was removed, eventually obtaining cell lines that are transferred protein (EGFR, EGFR/C797S, BLK, BMX, JAK3, LYN)-dependent.

In this example different concentrations (0.000508 μM, 0.00152 μM, 0.00457 μM, 0.0137 μM, 0.0411 μM, 0.123 μM, 0.370 μM, 1.11 μM, 3.33 μM, 10 μM) of Compound 1 and Compound 6 were respectively added into the above cells which were then cultured for 72 hours. The number of viable cells was determined via quantitative determination of ATP in living cells by using Cell Titer-Glo® (Promega, the USA) Chemical Luminescent Cell Viability Assay kit. It was found that Compound 1 and Compound 6 exhibited very significant inhibitory effects against growth of diffuse large B-cell lymphoma cell lines, TMD8 cells, wherein the $GI_{50}$ is 0.001 and 0.75 μM, respectively (see Table 4 below); they had a weaker inhibitory effects on other leukemia cells, corroborating the selectively of the compounds of this invention in treating diffuse large B-cell lymphoma.

In addition, the same method was used to test the effects of other compounds on proliferation of diffuse large B-cell lymphoma TMD8 cells, and it was found that Compounds 28, 31, 35, 64, 68, 74, 75, and 76 had significant inhibitory effects on growth of diffuse large B-cell lymphoma cell lines TMD8 cells, wherein the $GI_{50}$ were all below 0.1 μM (see Table 5 below), corroborating the selectively of the compounds of this invention in treating diffuse large B-cell lymphoma.

TABLE 4

Effects on cell proliferation ($GI_{50}$, μM)

|  | Compound 6 | Compound 1 |
|---|---|---|
| HL60 | >10 | 5.5 |
| TMD8 | 0.75 | 0.001 |
| U2932 | >10 | 2.4 |
| HEL | >10 | 5.3 |
| U937 | >10 | 4.8 |
| MOLM14 | >10 | 6.4 |
| MOLM13 | 4.0 | 2.2 |
| M-07e | >10 | 7.3 |
| K562 | >10 | 4.2 |
| MV4-11 | 4.8 | 2.1 |
| MOLM-16 | >10 | 3.5 |
| HCT116 | >10 | >10 |
| OCI-AML-3 | 9.5 | 3.8 |
| NB4 | >10 | 6.6 |
| SKM-1 | >10 | 7.1 |
| Pfeiffer | >10 | 4.5 |
| Romas | 4.6 | 3.5 |
| RPMI8226 | 4.7 | 2.9 |
| AMO-1 | 8.0 | 3.4 |
| OCI-LY10 | 3-10 | 3.4 |
| SU-DHL-2 | >10 | 3.0 |
| WT-BaF3 | 6.3 | 7.9 |
| BaF3-tel-BMX | 4.1 | 0.38 |
| BaF3-tel-BLK | 5.4 | 4.7 |
| BaF3-tel-JAK3 | 4.6 | 3.2 |
| BaF3-tel-EGFR | 7.6 | 5.3 |
| BaF3-tel-EGFR-C797S | 1.8 | 2.5 |
| BaF3-tel-LYN | 6.8 | 6.3 |

TABLE 5

Effects on TMD8 cell proliferation ($GI_{50}$, μM)

|  | TMD8 |
|---|---|
| CGI1746 | 0.126 |
| PCI32765 | 0.001 |
| Compound 1 | 0.001 |
| Compound 28 | 0.0035 |
| Compound 31 | 0.0094 |
| Compound 35 | 0.01 |
| Compound 64 | 0.012 |
| Compound 68 | 0.012 |
| Compound 74 | 0.0072 |
| Compound 75 | 0.0074 |
| Compound 76 | 0.006 |

INDUSTRIAL APPLICABILITY

The present invention provides an irreversible inhibitor of Bruton's tyrosine kinase which is useful in inhibiting Bruton's tyrosine kinase activity or treating a disease, disorder, or condition, which would benefit from the inhibition of Bruton's tyrosine kinase(s). Therefore, it may be prepared as corresponding medicaments and has industrial applicability.

While the invention has been described in detail herein, the invention is not limited thereto and modifications may be made by those skilled in the art based on the principles of the invention, and thus, all modifications in accordance with the principles of the invention are to be understood as within the protection scope of the invention.

The invention claimed is:

1. A compound of formula (I) or a pharmaceutically acceptable salt, solvate, ester, acid, or prodrug thereof, said compound having a structure of:

formula (I)

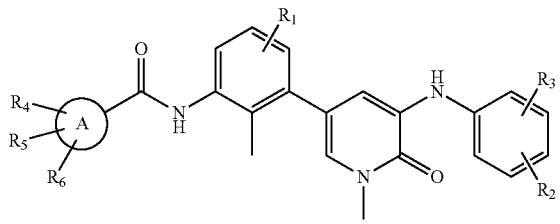

wherein,
ring A represents any monocyclic or fused-ring group selected from the group consisting of phenyl, thienyl, benzothienyl, and tetrahydrobenzothienyl;
$R_1$ is hydrogen;
$R_2$ is selected from the group consisting of

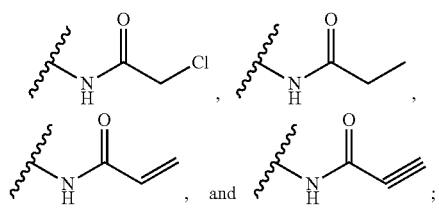

$R_3$ is selected from the group consisting of hydrogen, C1-C8 alkyl, halo, hydroxy, nitro, cyano, C1-C8 haloalkyl, amino, C1-C8 alkylamino, —(CO)—$R_7$, heterocycloalkyl optionally substituted with $R_8$, and heteroaryl optionally substituted with $R_8$;
each of $R_4$, $R_5$ and $R_6$ is independently selected from the group consisting of hydrogen, halo, hydroxy, amino, nitro, cyano, C1-C8 alkyl, C3-C8 cycloalkyl, C1-C8 haloalkyl, C1-C8 alkoxy, C1-C8 alkylamino, heterocycloalkyl, aryl and heteroaryl, or any adjacent two of $R_4$, $R_5$ and $R_6$ together form C3-C8 cycloalkyl or heterocycloalkyl;
$R_7$ is selected from the group consisting of C1-C8 alkoxy, C1-C8 alkylamino, C3-C8 cycloalkylamino, C2-C8 heteroalkylamino, C3-C8 heterocycloalkylamino, and heterocycloalkyl optionally substituted with halo, hydroxy, amino, nitro, cyano, C1-C8 alkyl, C1-C8 alkoxy, or amino protecting group;
$R_8$ is selected from the group consisting of C1-C8 alkyl, C1-C8 alkoxy, C1-C8 alkylamino or C2-C8 alkanoyl.

2. The compound or a pharmaceutically acceptable salt, solvate, ester, acid, or prodrug thereof according to claim 1, wherein $R_3$ is selected from the group consisting of hydrogen, C1-C6 alkyl, C1-C6 alkylamino, —(CO)—$R_7$, heterocycloalkyl optionally substituted with $R_8$, and heteroaryl optionally substituted with $R_8$; and $R_7$ is selected from the group consisting of C1-C6 alkoxy, C1-C6 alkylamino, C3-C6 cycloalkylamino, C2-C6 heteroalkylamino, C3-C6 heterocycloalkylamino, and heterocycloalkyl optionally substituted with halo, hydroxy, amino, nitro, cyano, C1-C8 alkyl, C1-C8 alkoxy, or amino protecting group; $R_8$ is selected from the group consisting of C1-C6 alkyl, C1-C6 alkoxy, C2-C6 alkanoyl, and C1-C8 alkylamino.

3. The compound or a pharmaceutically acceptable salt, solvate, ester, acid, or prodrug thereof according to claim 1, wherein each of $R_4$, $R_5$ and $R_6$ is independently selected from the group consisting of hydrogen, C1-C6 alkyl, C3-C6 cycloalkyl, C1-C6 haloalkyl, C1-C6 alkoxy, C1-C6 alkylamino, heterocycloalkyl, or any adjacent two of $R_4$, $R_5$ and $R_6$ together form C3-C6 cycloalkyl or heterocycloalkyl.

4. The compound or a pharmaceutically acceptable salt, solvate, ester, acid, or prodrug thereof according to claim 1, wherein $R_2$ is selected from the group consisting of

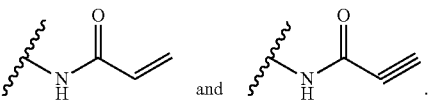

5. The compound or a pharmaceutically acceptable salt, solvate, ester, acid, or prodrug thereof according to claim 1, wherein
ring A represents any monocyclic or fused-ring group selected from the group consisting of phenyl, thiophene-2-yl, benzo[b]thiophene-2-yl, and 4,5,6,7-tetrahydrobenzo[b]thiophene-2-yl;
$R_3$ is selected from the group consisting of hydrogen, methyl, dimethylamino, —(CO)—$R_7$, and piperazinyl, morpholinyl, piperidyl, pyrrolidyl and pyrazolyl optionally substituted with $R_8$; and $R_7$ is selected from the group consisting of methoxy, dimethylamino, cyclopropylamino, N-(2-methoxyethyl)amino, N,N-bis(2-ethoxyethyl)amino, tetrahydropyran-4-ylamino, pyrrolidyl, piperidyl optionally substituted with hydroxyl or methoxy, morpholinyl, and piperazinyl with its nitrogen(s) being optionally substituted with methyl or Boc; $R_8$ is selected from the group consisting of methyl, ethyl, isopropyl, methoxy, acetyl, and dimethylamino;
each of $R_4$, $R_5$ and $R_6$ is independently selected from the group consisting of hydrogen, methyl, ethyl, isopropyl, tert-butyl, cyclopropyl, trifluoromethyl, methoxy, dimethylamino, morpholinyl, and pyrrolidyl, or any adjacent two of $R_4$, $R_5$ and $R_6$ together form cyclohexyl, dioxolanyl, or dioxanyl.

6. The compound or a pharmaceutically acceptable salt, solvate, ester, acid, or prodrug thereof according to claim 1, said compound having a structure of formula (Ia):

formula (Ia)

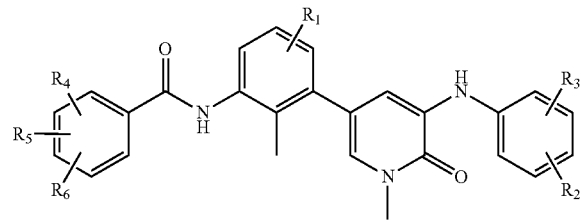

wherein,
$R_1$ is hydrogen,
$R_2$ is selected from the group consisting of

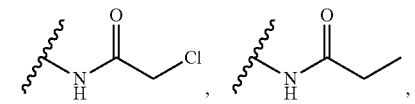

-continued

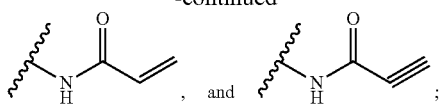

R₃ is selected from the group consisting of hydrogen, C1-C8 alkyl, halo, hydroxy, nitro, cyano, C1-C8 haloalkyl, amino, C1-C8 alkylamino, —(CO)—R₇, and heterocycloalkyl optionally substituted with R₈;

each of R₄, R₅ and R₆ is independently selected from the group consisting of hydrogen, halo, hydroxy, amino, nitro, cyano, C1-C8 alkyl, C3-C8 cycloalkyl, C1-C8 haloalkyl, C1-C8 alkoxy, C1-C8 alkylamino, heterocycloalkyl, aryl and heteroaryl, or any adjacent two of R₄, R₅ and R₆ together form C3-C8 cycloalkyl or heterocycloalkyl;

R₇ is selected from the group consisting of C1-C8 alkoxy, C1-C8 alkylamino, C3-C8 cycloalkylamino, C2-C8 heteroalkylamino, C3-C8 heterocycloalkylamino, and heterocycloalkyl optionally substituted with halo, hydroxy, amino, nitro, cyano, C1-C8 alkyl, C1-C8 alkoxy, or amino protecting group;

R₈ is selected from the group consisting of C1-C8 alkyl.

7. The compound or a pharmaceutically acceptable salt, solvate, ester, acid, or prodrug thereof according to claim 6, wherein R₃ is selected from the group consisting of hydrogen, C1-C6 alkyl, and —(CO)—R₇, and heterocycloalkyl optionally substituted with C1-C6 alkyl; and R₇ is selected from the group consisting of C1-C6 alkoxy, C1-C6 alkylamino, C3-C6 cycloalkylamino, C2-C6 heteroalkylamino, C3-C6 heterocycloalkylamino, and optionally substituted heterocycloalkyl.

8. The compound or a pharmaceutically acceptable salt, solvate, ester, acid, or prodrug thereof according to claim 6, wherein each of R₄, R₅ and R₆ is independently selected from the group consisting of hydrogen, C1-C6 alkyl, C3-C6 cycloalkyl, C1-C6 haloalkyl, C1-C6 alkoxy, C1-C6 alkylamino, heterocycloalkyl, or any adjacent two of R₄, R₅ and R₆ together form C3-C6 cycloalkyl or heterocycloalkyl.

9. The compound or a pharmaceutically acceptable salt, solvate, ester, acid, or prodrug thereof according to claim 6, said compound having a structure of formula (IIa):

formula (IIa)

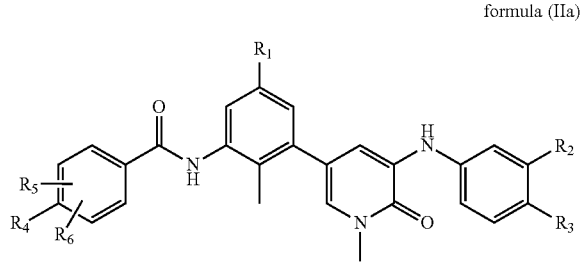

wherein
R₁ is hydrogen; R₂ is

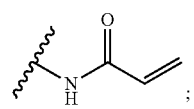

R₃ is heterocycloalkyl optionally substituted with C1-C6 alkyl, or —(CO)—R₇, and R₇ is selected from the group consisting of C1-C6 alkylamino, C3-C6 cycloalkylamino, C3-C6 heterocycloalkylamino, and optionally substituted heterocycloalkyl; R₄ is selected from the group consisting of C1-C6 alkyl, C1-C6 alkylamino, and heterocycloalkyl, and each of R₅ and R₆ is hydrogen, or any adjacent two of R₄, R₅ and R₆ together form C3-C6 cycloalkyl or heterocycloalkyl.

10. The compound or a pharmaceutically acceptable salt, solvate, ester, acid, or prodrug thereof according to claim 1, said compound having the structure of formula (Ib):

formula (Ib)

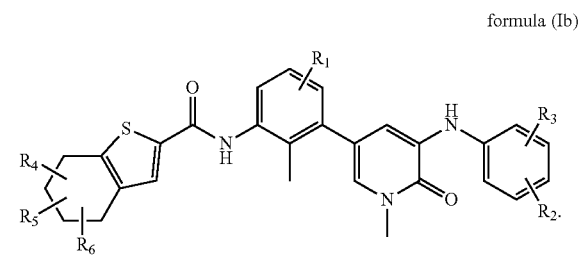

11. The compound or a pharmaceutically acceptable salt, solvate, ester, acid, or prodrug thereof according to claim 10, said compound having a structure of formula (IIb):

formula (IIb)

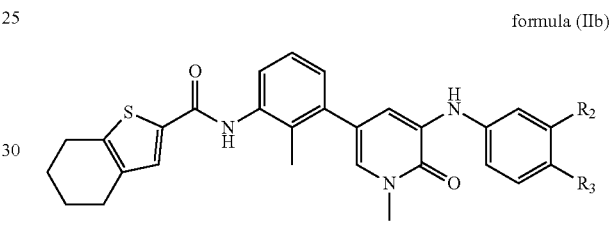

wherein,
R₂ is selected from the group consisting of

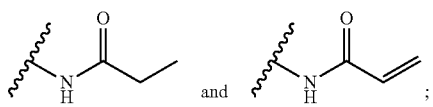

R₃ is selected from the group consisting of dimethylamino, —(CO)—R₇, and piperazinyl, morpholinyl, pyrrolidyl, piperidyl, and pyrazolyl optionally substituted with R₈; R₇ is selected from the group consisting of morpholinyl, and pyrrolidyl; R₈ is selected from the group consisting of methyl, ethyl, isopropyl, methoxy, dimethylamino, and acetyl.

12. The compound or a pharmaceutically acceptable salt, solvate, acid, or prodrug thereof according to claim 1, said compound having the structure of formula (Ic):

formula (Ic)

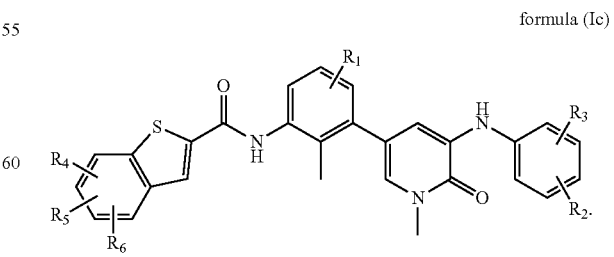

13. The compound or a pharmaceutically acceptable salt, solvate, ester, acid, or prodrug thereof according to claim 12, said compound having the structure of formula (IIc):

formula (IIc)

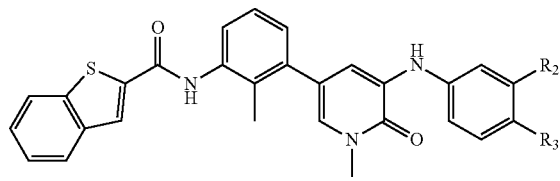

wherein,
R₂ is

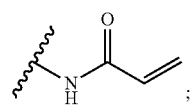

R₃ is selected from the group consisting of dimethylamino, —(CO)—R₇, and piperazinyl, morpholinyl, pyrrolidyl, piperidyl, and pyrazolyl optionally substituted with R₈; R₇ is selected from the group consisting of morpholinyl, and pyrrolidyl; R₈ is selected from the group consisting of methyl, ethyl, isopropyl, methoxy, dimethylamino, and acetyl.

14. The compound or a pharmaceutically acceptable salt, solvate, ester, acid, or prodrug thereof according to claim 1, said compound having the structure of formula (Id):

formula (Id)

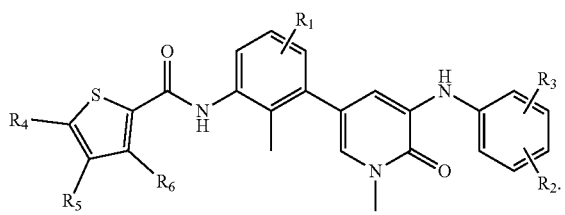

15. The compound or a pharmaceutically acceptable salt, solvate, ester, acid, or prodrug thereof according to claim 14, said compound having the structure of formula (IId):

formula (IId)

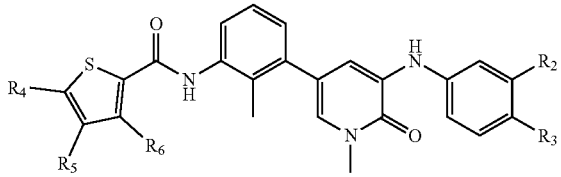

wherein,
R₂ is

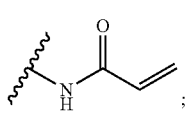 [SMILES: *NC(=O)C=C]

R₃ is selected from the group consisting of dimethylamino, —(CO)—R₇, and piperazinyl, morpholinyl, pyrrolidyl, piperidyl, and pyrazolyl optionally substituted with R₈; R₇ is selected from the group consisting of morpholinyl, and pyrrolidyl; R₈ is selected from the group consisting of methyl, ethyl, isopropyl, methoxy, dimethylamino, and acetyl;

each of R₄, R₅ and R₆ is independently selected from the group consisting of hydrogen and methyl.

16. The compound or a pharmaceutically acceptable salt, solvate, ester, acid, or prodrug thereof according to claim 1, said compound being selected from the group consisting of following compounds:

Compound 1

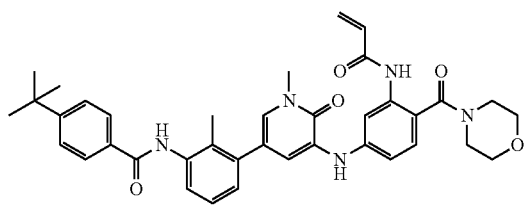

Compound 2

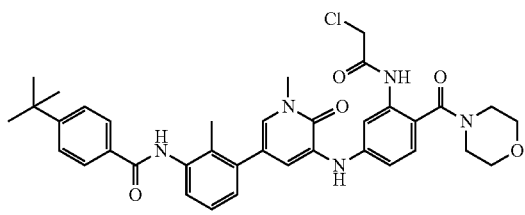

Compound 3

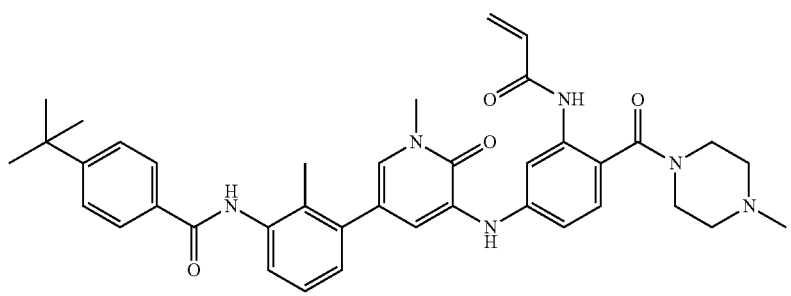

-continued
Compound 4
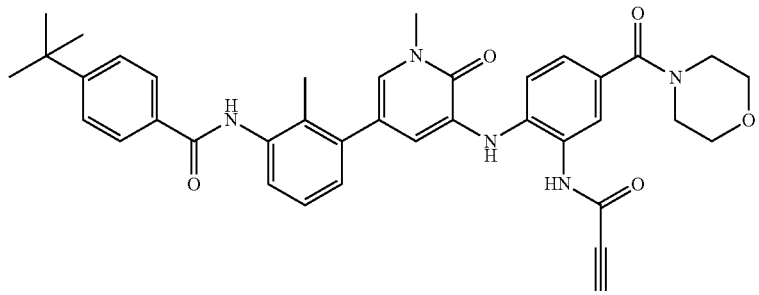
Compound 5
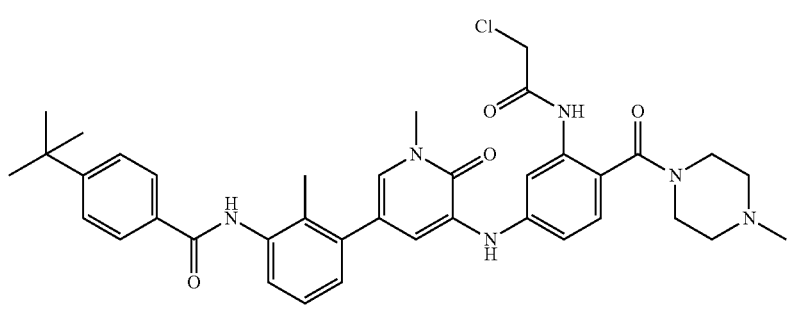
Compound 6
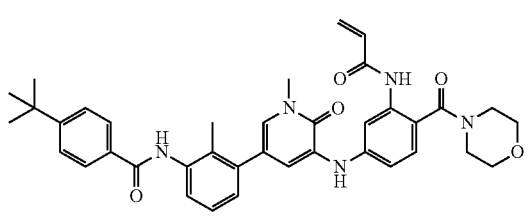
Compound 9
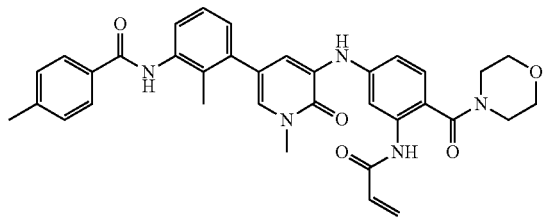
Compound 10
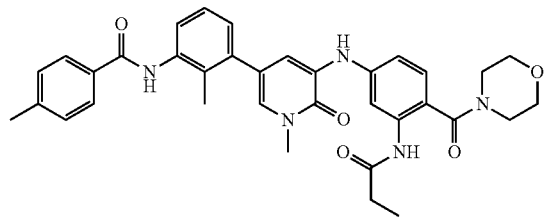
Compound 11
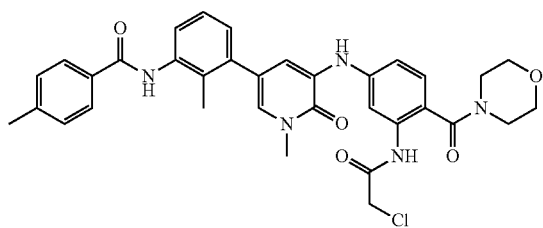
Compound 12
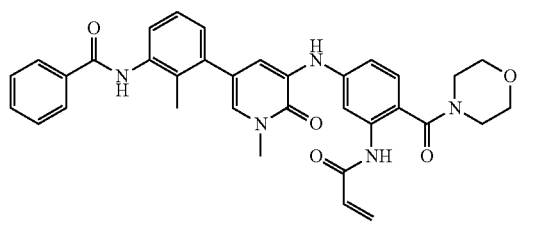
Compound 13
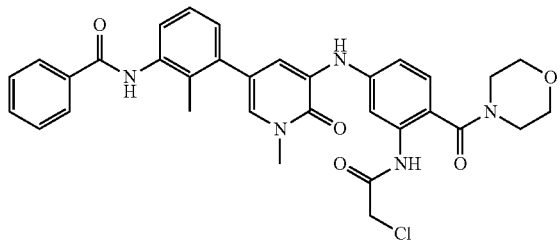
Compound 14
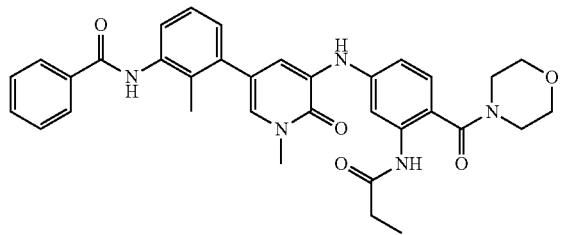

Compound 15
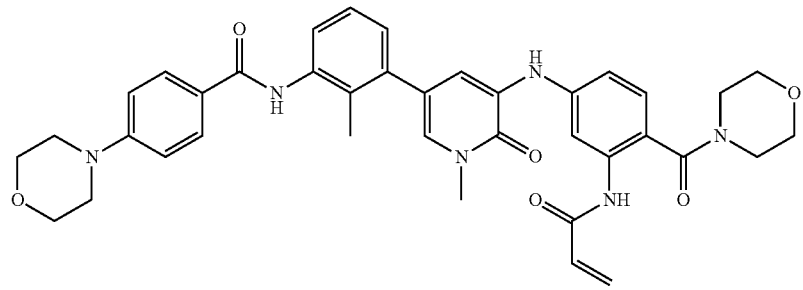
Compound 16
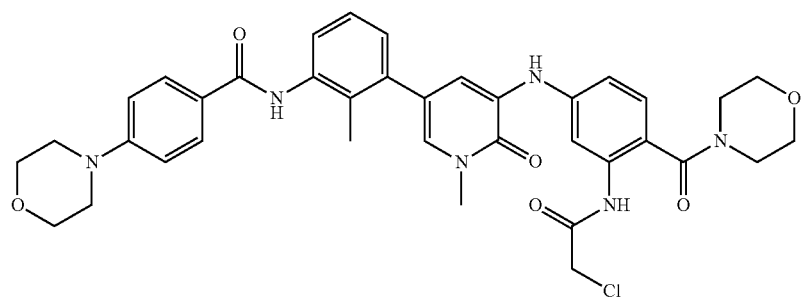
Compound 17
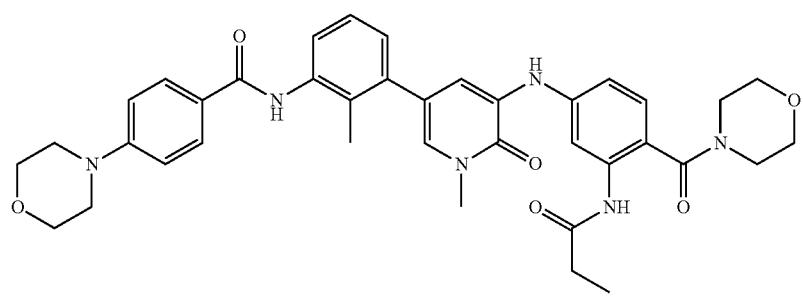
Compound 18
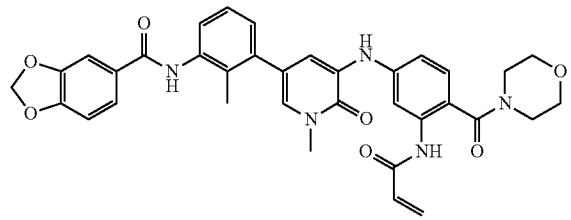
Compound 19
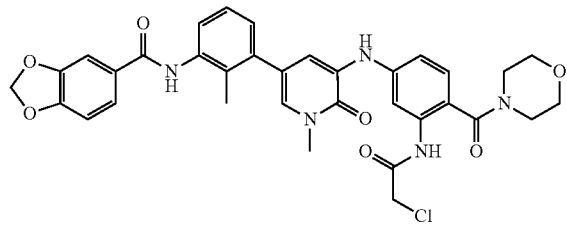
Compound 20
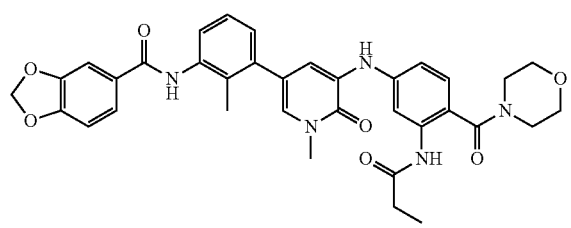
Compound 21
Compound 22
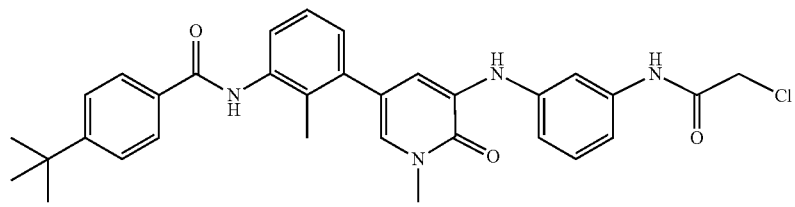

-continued
Compound 23
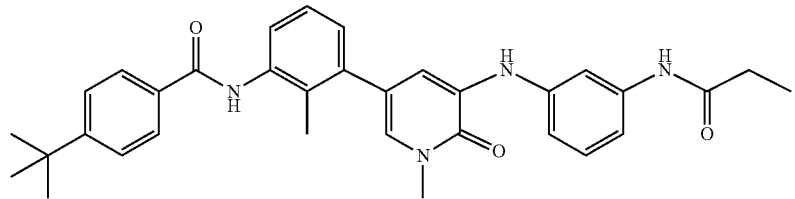
Compound 25
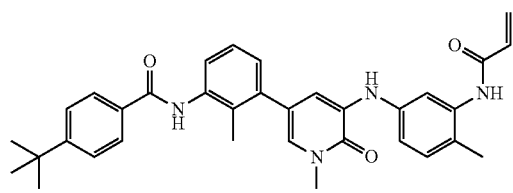
Compound 26
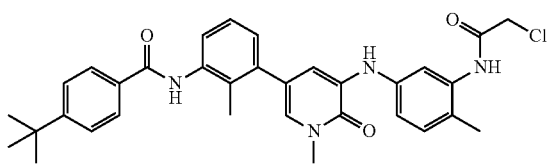
Compound 27
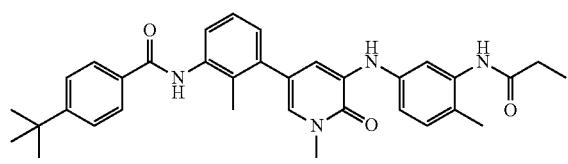
Compound 28
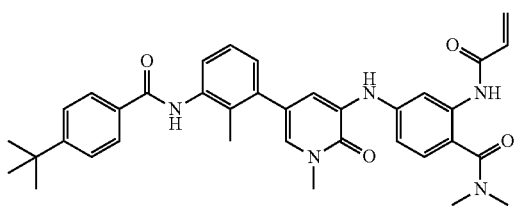
Compound 29
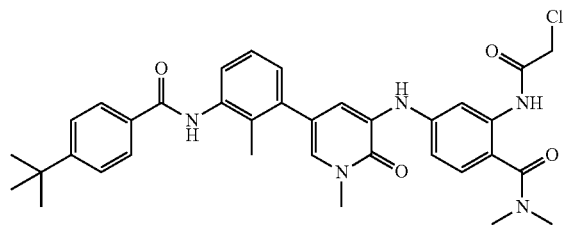
Compound 30
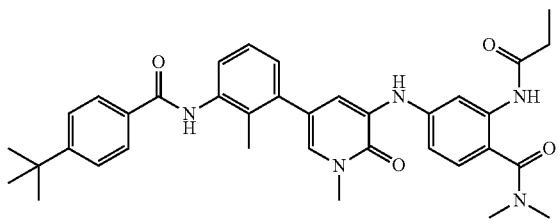
Compound 31
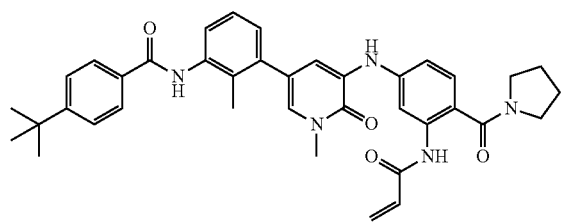
Compound 32
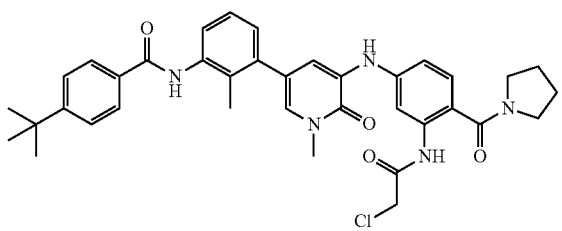
Compound 33
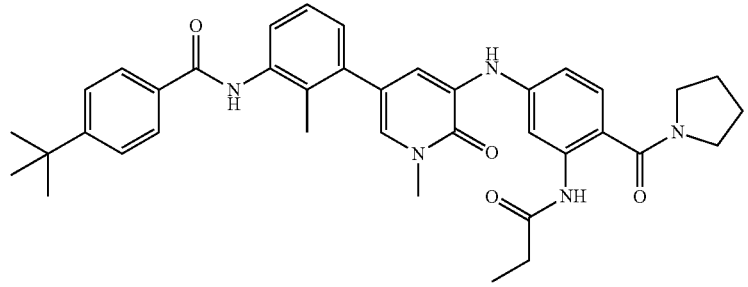

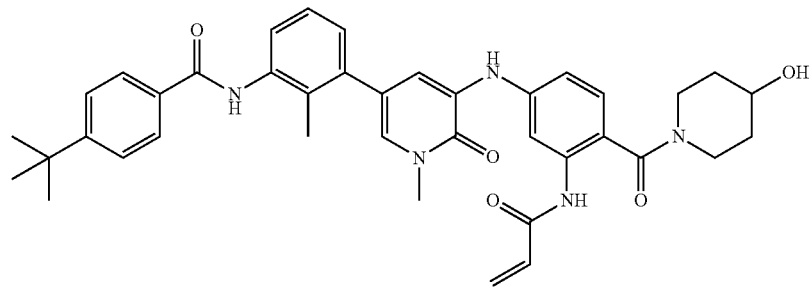
Compound 34
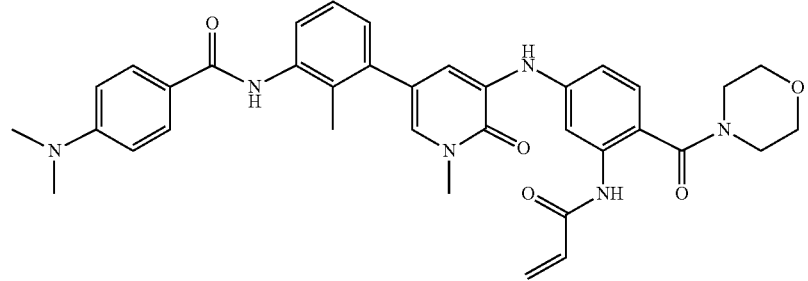
Compound 35
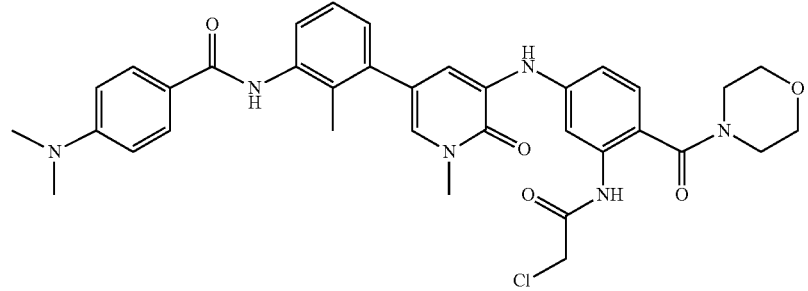
Compound 36
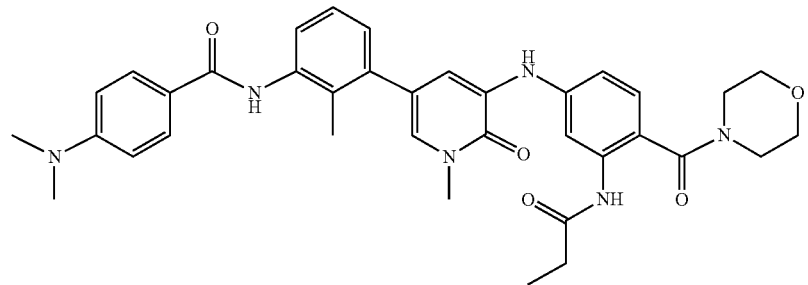
Compound 37
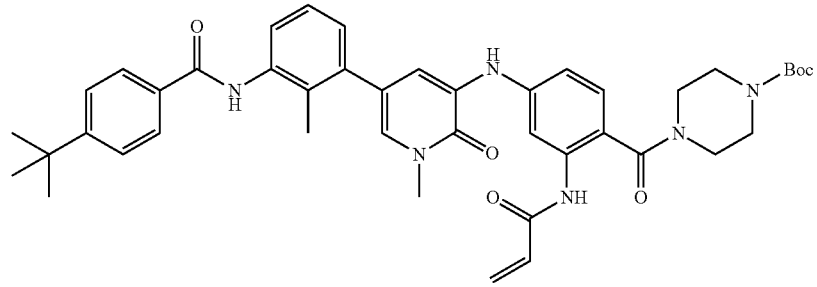
Compound 38

Compound 39
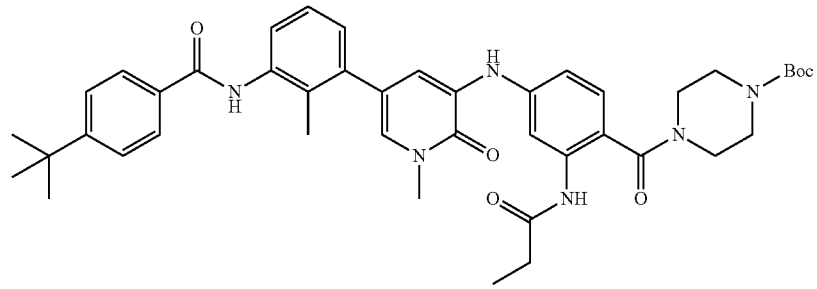
Compound 40
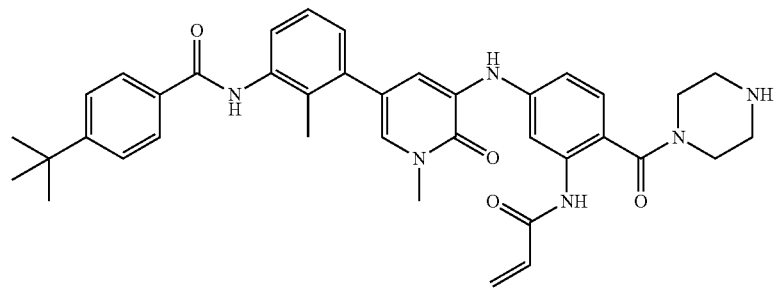
Compound 41
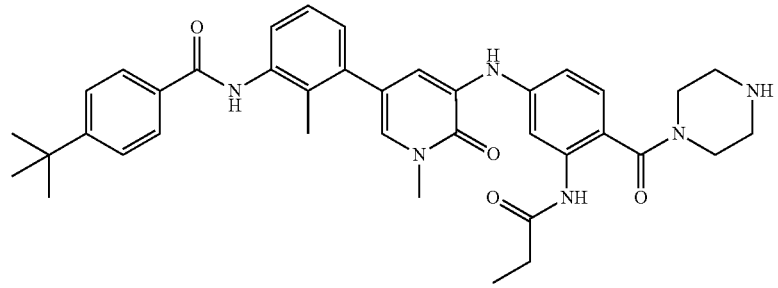
Compound 42
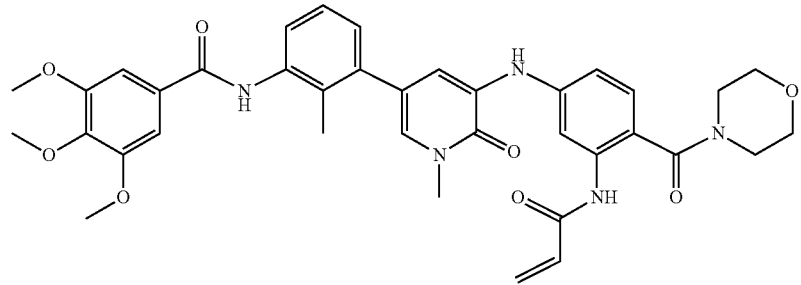
Compound 43
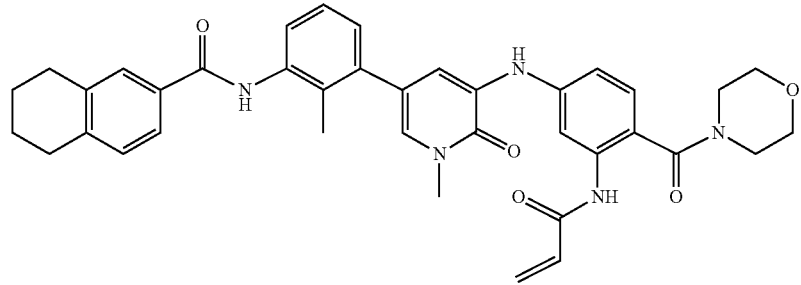

-continued
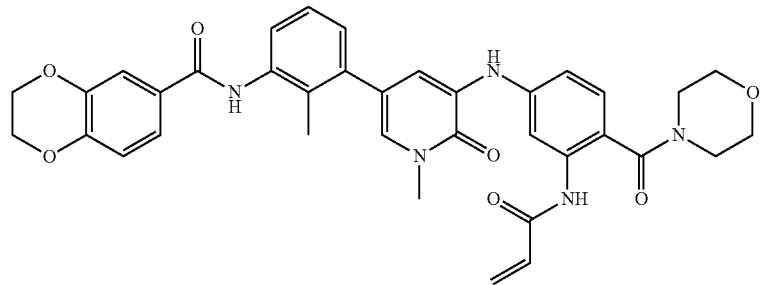
Compound 44
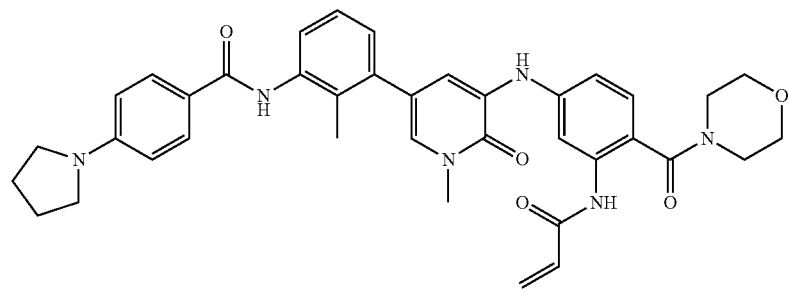
Compound 45
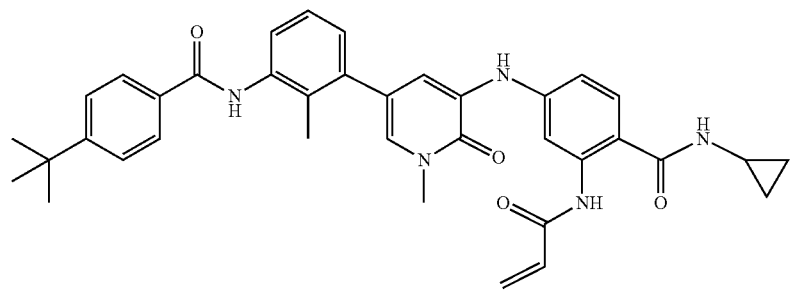
Compound 46
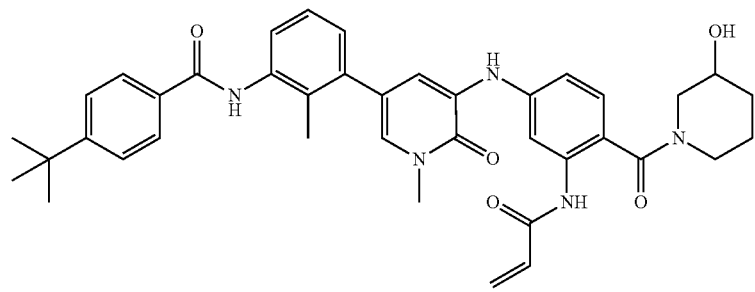
Compound 47
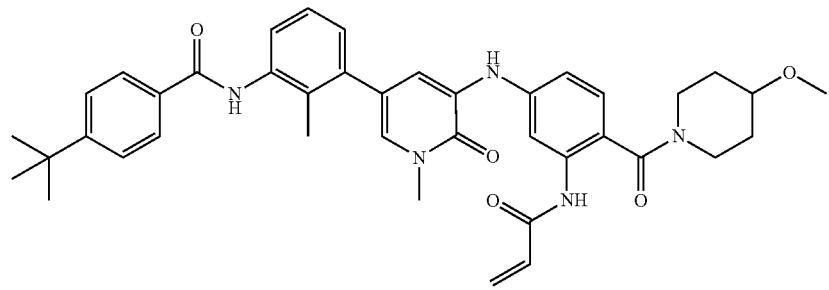
Compound 48

-continued
Compound 49
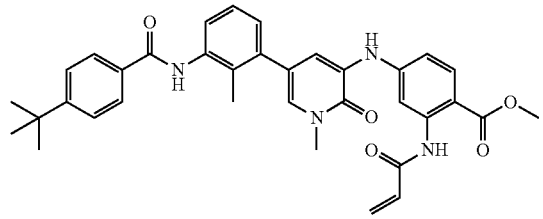
Compound 50
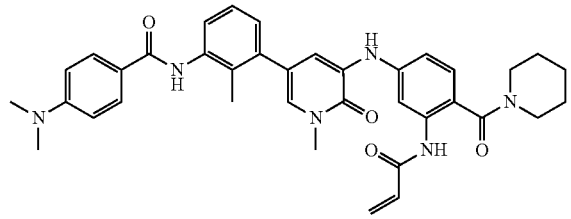
Compound 51
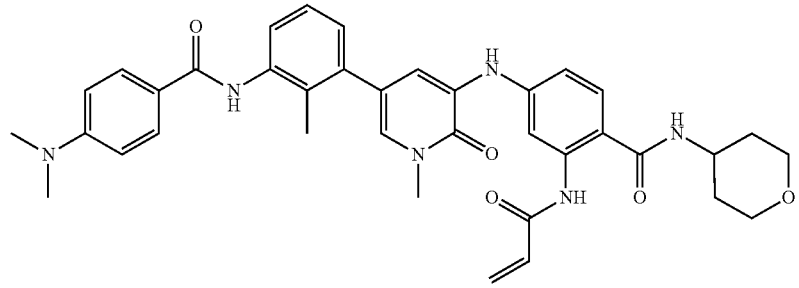
Compound 52
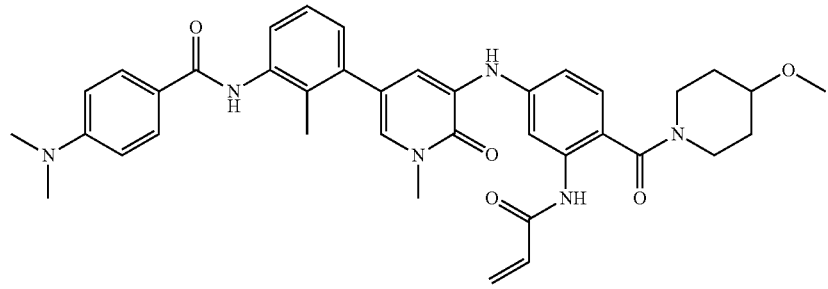
Compound 53
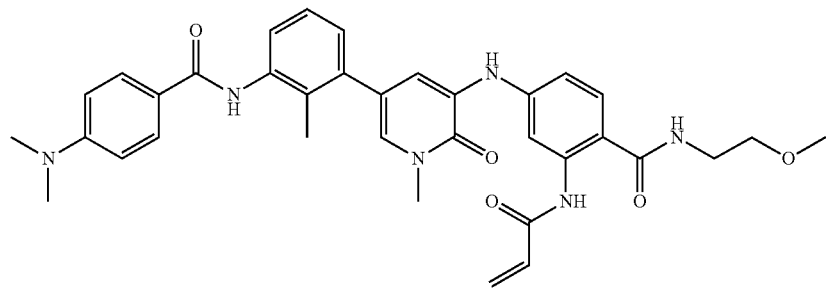
Compound 54
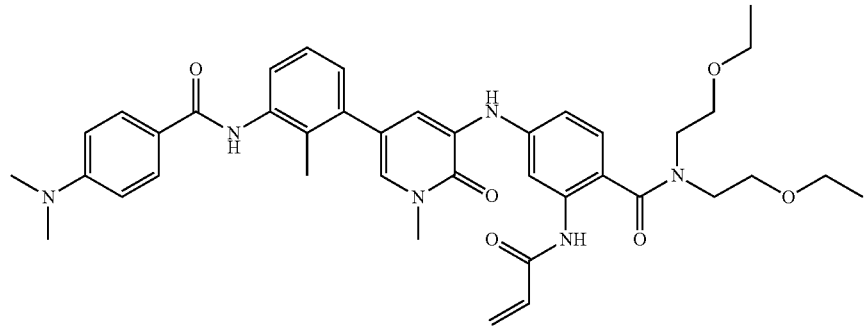

Compound 55
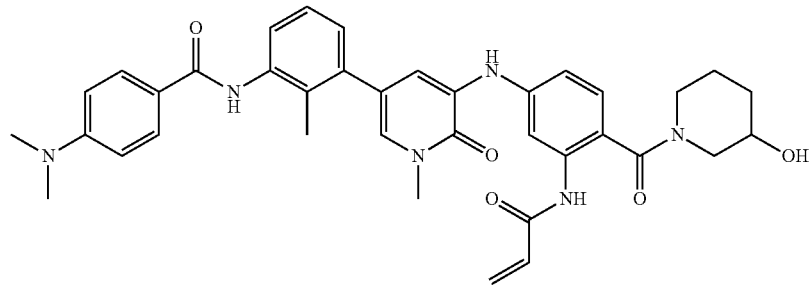
Compound 56
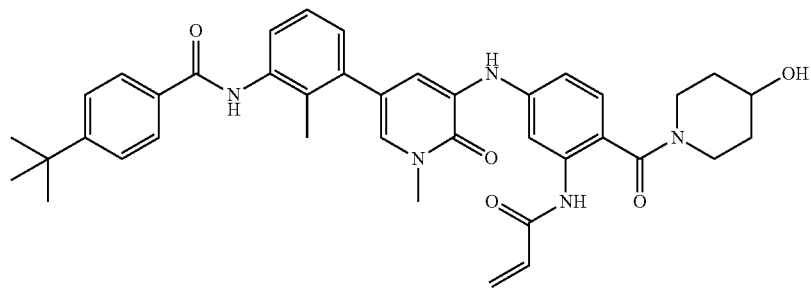
Compound 57
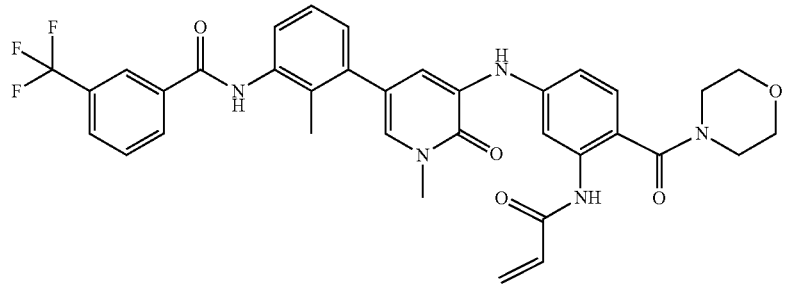
Compound 58
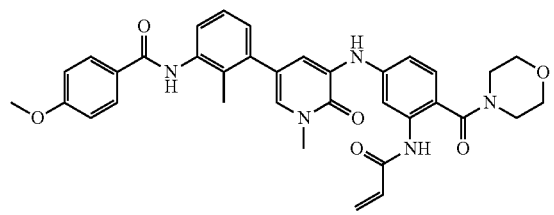
Compound 59
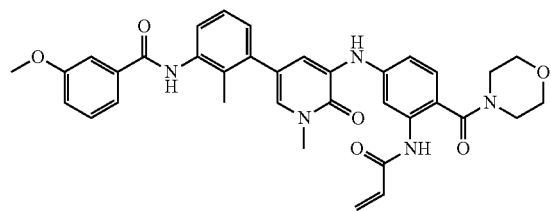
Compound 60
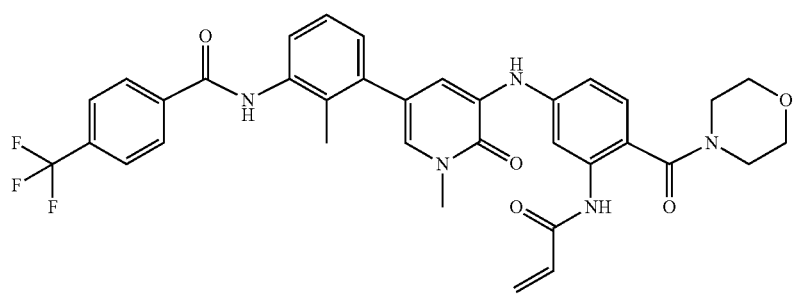

-continued
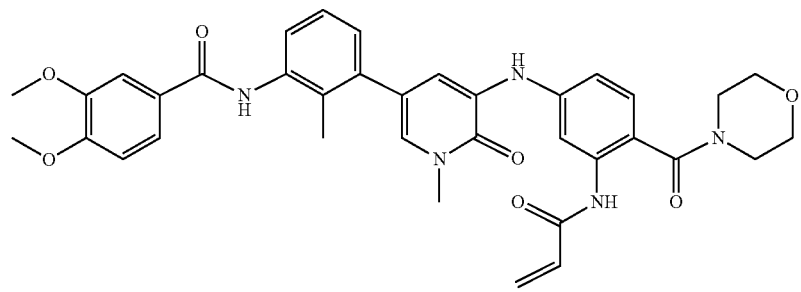
Compound 61
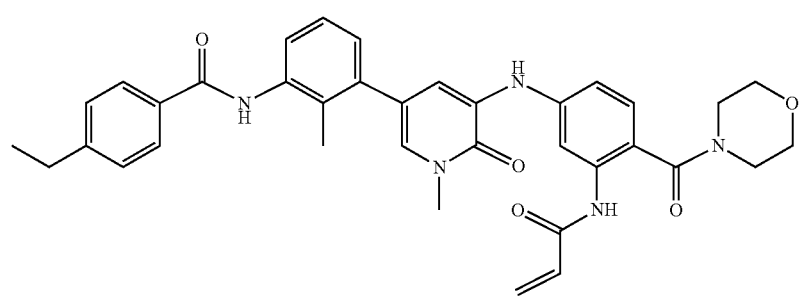
Compound 62
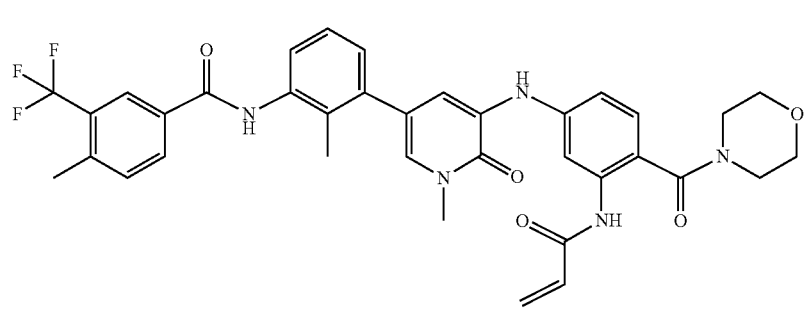
Compound 63
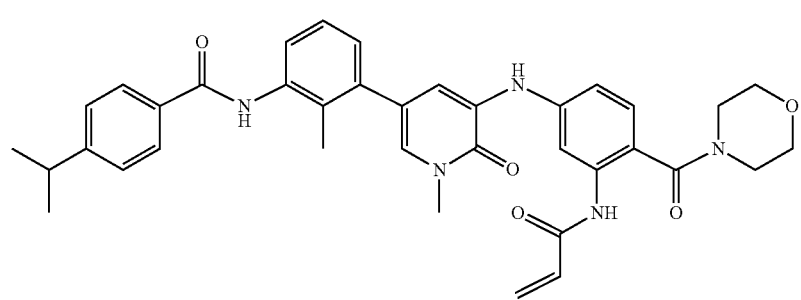
Compound 64
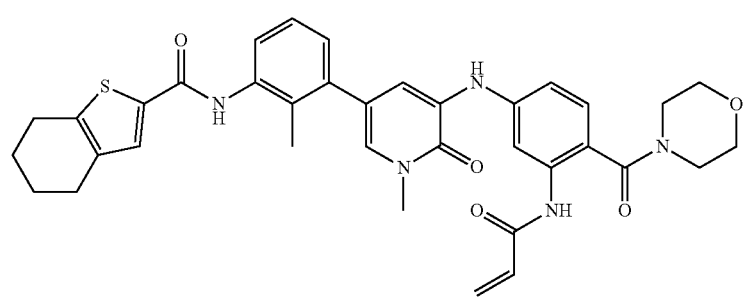
Compound 65

Compound 66
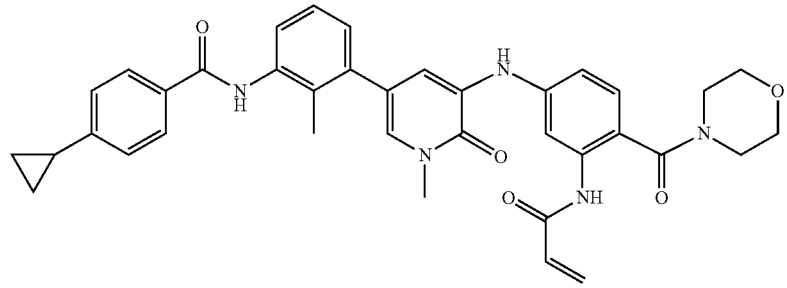
Compound 67
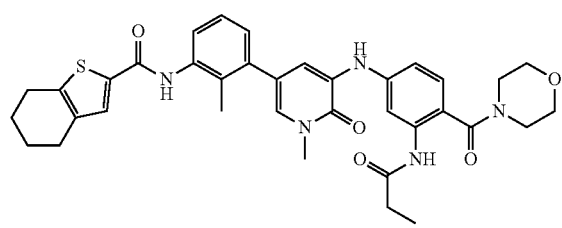
Compound 68
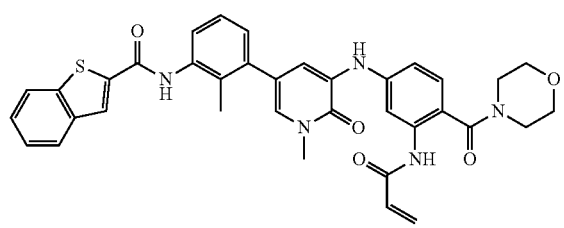
Compound 69
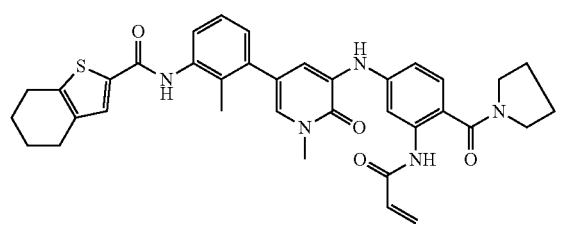
Compound 70
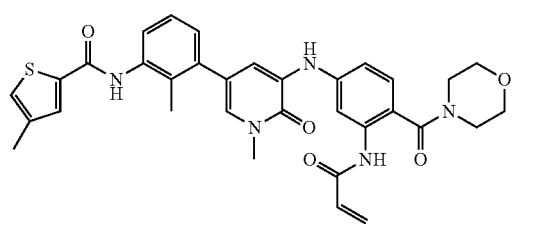
Compound 71
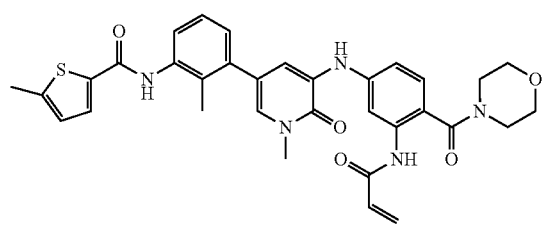
Compound 72
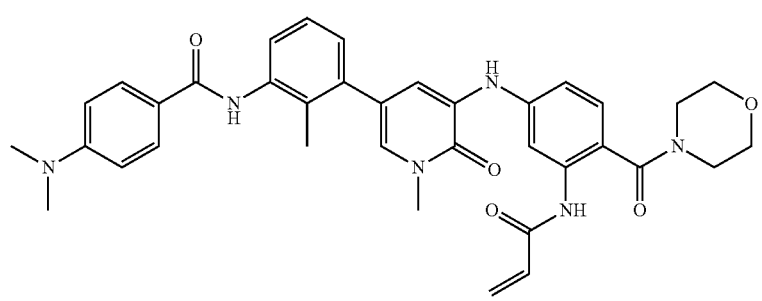
Compound 73
Compound 74
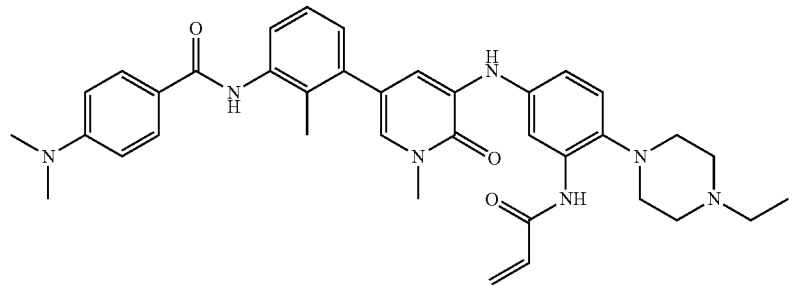

Compound 75
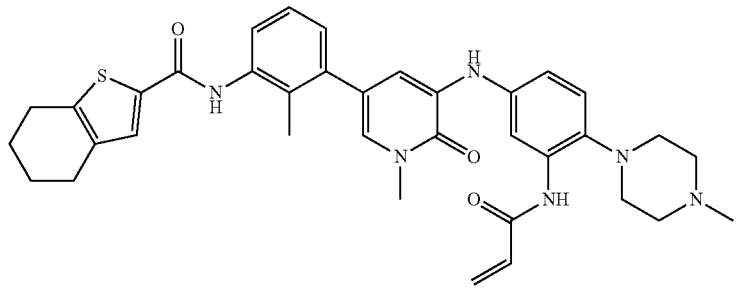
Compound 76
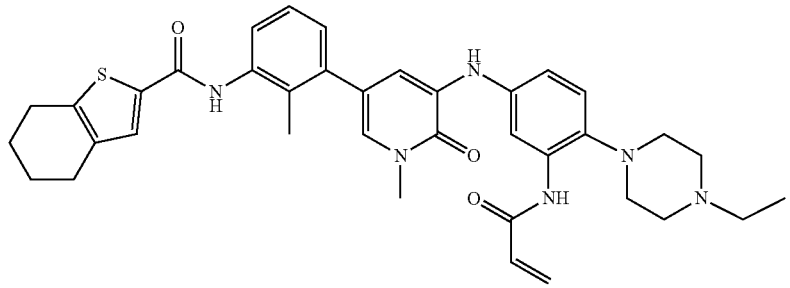
Compound 77
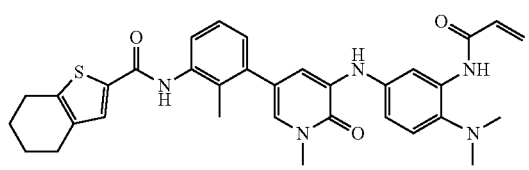
Compound 78
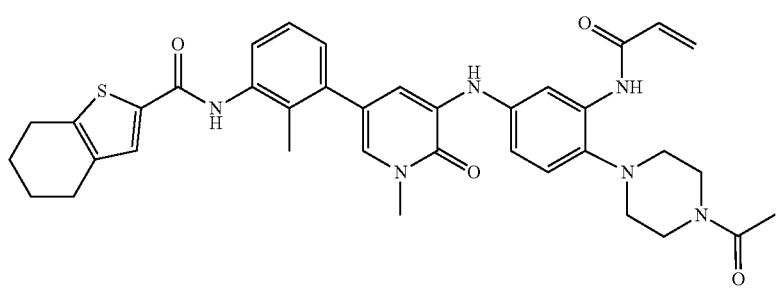
Compound 80
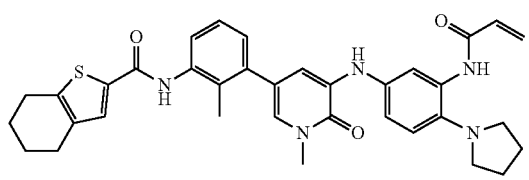
Compound 81
Compound 82
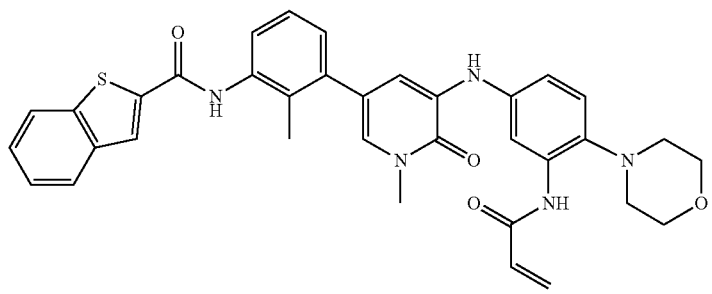

-continued
Compound 83
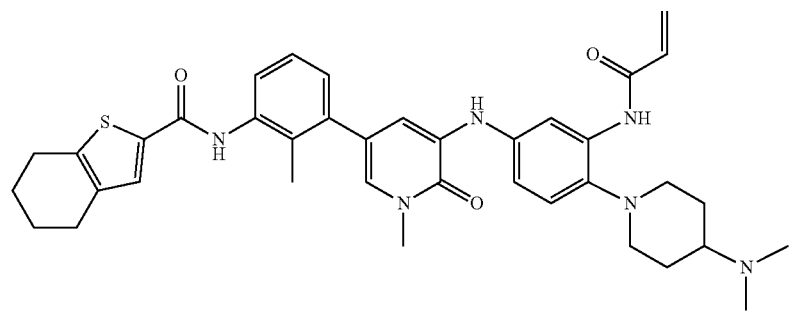
Compound 84
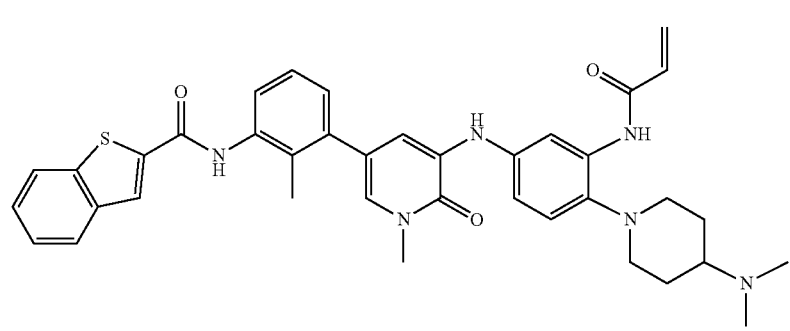
Compound 85
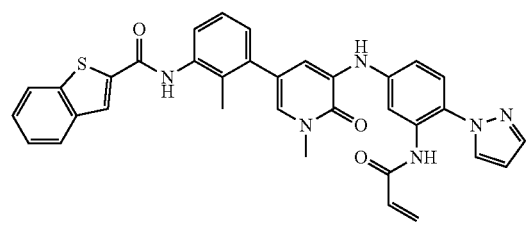
Compound 86
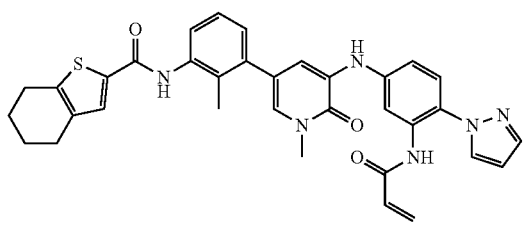
Compound 87
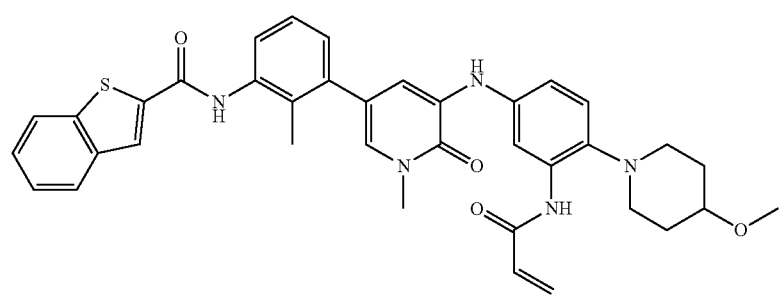
Compound 88
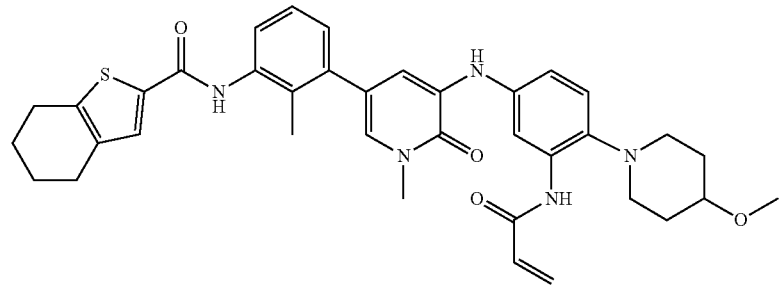

-continued
Compound 89
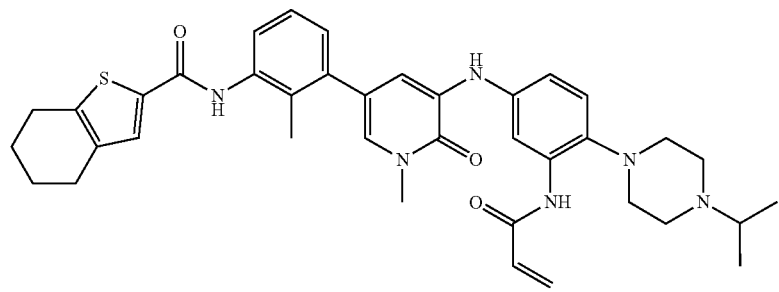
Compound 90
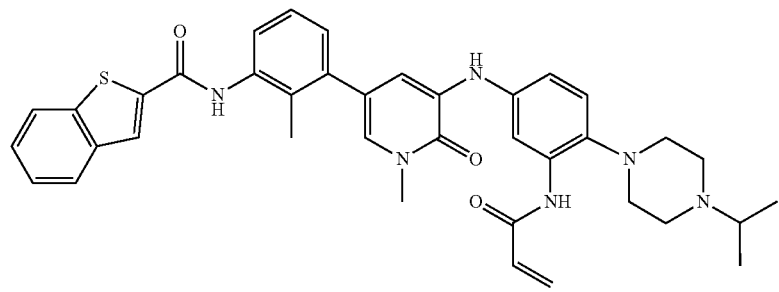
Compound 91
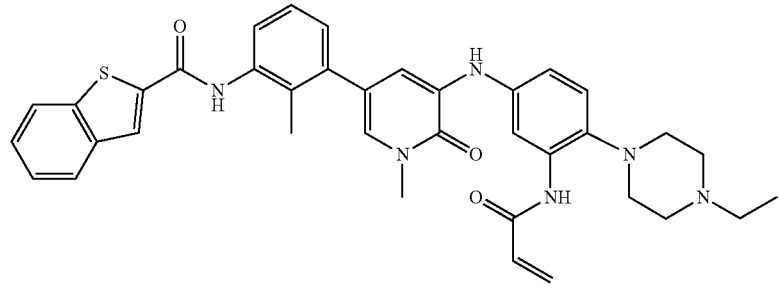
Compound 92
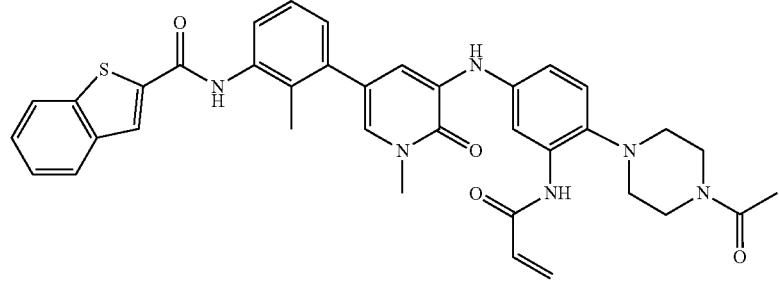
Compound 93
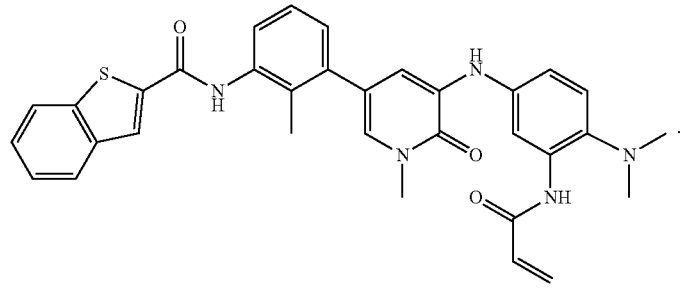

17. A pharmaceutical composition, which comprises the compound or a pharmaceutically acceptable salt, solvate, ester, acid, or prodrug thereof of claim 1, and a pharmaceutically acceptable carrier or excipient.

18. A method of treating or improving a disease or condition in a subject, wherein the disease or condition is modulated by or otherwise affected by Bruton's tyrosine kinase activity or in which Bruton's tyrosine kinase activity is implicated, comprising administering to the subject the compound or a pharmaceutically acceptable salt, solvate, ester, acid, or prodrug thereof of claim 1.

19. The method of claim 18, wherein the disease or condition is cancer.

20. The method of claim 19, wherein the disease or condition is diffuse large B-cell lymphoma.

21. The method of claim 18, wherein the compound or a pharmaceutically acceptable salt, solvate, ester, acid, or prodrug thereof is provided in a pharmaceutically acceptable carrier or excipient.

* * * * *

SEQUENCE LISTING

<160> NUMBER OF SEQ ID NOS: 14

<210> SEQ ID NO 1
<211> LENGTH: 15
<212> TYPE: PRT
<213> ORGANISM: Artificial Sequence
<220> FEATURE:
<223> OTHER INFORMATION: peptide

<400> SEQUENCE: 1

Ala Val Leu Glu Ser Glu Glu Glu Leu Tyr Ser Ser Ala Arg Gln
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: peptide

<400> SEQUENCE: 2

Ile Thr Glu Tyr Met Ala Asn Gly Cys Leu Leu
1               5                   10

```
<210> SEQ ID NO 3
<211> LENGTH: 11
<212> TYPE: PRT
<213> ORGANISM: Artificial Sequence
<220> FEATURE:
<223> OTHER INFORMATION: peptide

<400> SEQUENCE: 3

Val Thr Glu Tyr Met Ala Arg Gly Cys Leu Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: peptide

<400> SEQUENCE: 4

Val Thr Glu Phe Met Glu Arg Gly Cys Leu Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: peptide

<400> SEQUENCE: 5

Val Thr Glu Phe Met Glu Asn Gly Cys Leu Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: peptide

<400> SEQUENCE: 6

Val Phe Glu Phe Met Glu His Gly Cys Leu Ser
1               5                   10

<210> SEQ ID NO 7
<211> LENGTH: 11
<212> TYPE: PRT
<213> ORGANISM: Artificial Sequence
<220> FEATURE:
<223> OTHER INFORMATION: peptide

<400> SEQUENCE: 7

Ile Thr Gln Leu Met Pro Phe Gly Cys Leu Leu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: peptide

<400> SEQUENCE: 8

Val Thr Gln Leu Met Pro Tyr Gly Cys Leu Leu
1               5                   10
```

```
<210> SEQ ID NO 9
<211> LENGTH: 11
<212> TYPE: PRT
<213> ORGANISM: Artificial Sequence
<220> FEATURE:
<223> OTHER INFORMATION: peptide

<400> SEQUENCE: 9

Val Thr Gln Leu Met Pro His Gly Cys Leu Leu
1               5                   10

<210> SEQ ID NO 10
<211> LENGTH: 11
<212> TYPE: PRT
<213> ORGANISM: Artificial Sequence
<220> FEATURE:
<223> OTHER INFORMATION: peptide

<400> SEQUENCE: 10

Val Met Glu Tyr Leu Pro Ser Gly Cys Leu Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: peptide

<400> SEQUENCE: 11

Val Thr Glu Tyr Leu Pro Ser Gly Cys Leu Leu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: peptide

<400> SEQUENCE: 12

Ile Thr Glu Tyr Met Glu Asn Gly Ser Leu Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: peptide

<400> SEQUENCE: 13

Ile Thr Glu Tyr Met Ala Lys Gly Ser Leu Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: peptide

<400> SEQUENCE: 14

Val Met Glu Met Ala Glu Leu Gly Pro Leu Asn
1               5                   10
```